US005891692A

United States Patent [19]
Bloom et al.

[11] Patent Number: 5,891,692
[45] Date of Patent: *Apr. 6, 1999

[54] METHOD FOR INCREASING THE VIABILITY AND TRANSFORMATION ABILITY OF BACTERIA DURING OR AFTER STORAGE AT LOW TEMPERATURES

[75] Inventors: Fredric R. Bloom; Jonathan Kuo, both of Germantown; Jhy-Jhu Lin, Potomac; Jin Ma, Brookville, all of Md.

[73] Assignee: Life Technologies, Inc., Rockville, Md.

[*] Notice: This patent issued on a continued prosecution application filed under 37 CFR 1.53(d), and is subject to the twenty year patent term provisions of 35 U.S.C. 154(a)(2).

[21] Appl. No.: 826,426

[22] Filed: Mar. 27, 1997

Related U.S. Application Data

[60] Provisional application No. 60/

[51] Int. Cl.$^6$ .............................. C12N 5/10; C12N 15/63; C12N 15/87
[52] U.S. Cl. .................................. 435/172.3; 435/252.3; 435/252.33
[58] Field of Search ............................. 435/172.3, 252.3, 435/252.33

[56] References Cited

PUBLICATIONS

DeMendoza, et al, Thermal Regulation of Membrane Lipid Fludity In Bacteria, *Trends Biochem Sci.* 8:49–52 (Feb. 1983).
Wada, et al., Contribution of Membrane Lipids to the Ability of the Photosynthetic Machinery to Tolerate Temperature Stress. *Proc. Natl. Acad Sci.*, vol. 91 No. 10, pp. 4273–4277 (May 1994).
Gombos et al., Unsaturation Of Fatty Acids In Membrane Lipids Enhances Tolerance Of The Cyanobacterium Synechocystis PCC6803 To Low–Temperature Photoinhibition, *Proc. Natl. Acad. Sci.*, vol. 89, No. 20, pp. 9959–9963 (Oct. 1992).
Cronan, J.E. Jr. Thermal Regulation of the Membrane Lipid Composition of *Escherichia coli. J. Biol. Chem.*, vol. 250. No. 17, pp. 7074–7077 (Sep. 1975).
Reusch et al. Poly–B–Hydroxybutyrate Membrane Structure and Its Relationship to Genetic Transformability in *Escherichia coli J. Bact.*, vol. 168, No. 2, pp. 553–562 (Nov. 1986).
De Mendoza et al., *Journal of Bacteriology*, Overproduction of cis–Vaccenic Acid and Altered Temperature Control of Fatty Acid Synthesis in a Mutant of *Escherichia Coli., J. Bact.* vol. 151 No. 3 pp. 1608–1611 (Sep. 1982).
Pope, B. et al., *High Efficiency 5 Min Transformation of Escherichia Coli*, Nucleic Acids Research, V. 24, No. 3, pp. 536–537 (1996).
Adamczky, J. J., Jr., *Treatment of PCR Products with Shrimp Alkaline Phosphatase and Exonuclease I:* , Editorial Comments, V.22, No. 2, pp. 36, 49 (1995).

Lin et al, *AFLP™: A Novel PCR–Based Assay for Plant and Bacterial DNA Fingerprinting*, Focus, V. 17, pp. 66–70 (1995).
Old & Primrose, *Principles of Gene Manipulation: An Introduction to Genetic Engineering*, Chapter 2, Basic Techniques, Blackwell, Science pp. 6–21 (1995).
Trinh et al., STBL2™: An *Escherichia Coli* Strain for the Stable Propagation of Retroviral Clone and Direct Repeat Sequences, Focus, V. 16, pp. 78–80 (1994).
Hanahan et al., *Plasmid Transformation of Escherichia Coli and Other Bacteria*, Methods in Enzymology, V. 204, pp. 63–113 (1991).
Liu et al., *Comparison of Various Competent Cell Preparaton Methods for High Efficiency DNA Transformation*, BioTechniques, V. 8, No. 1, pp. 21, 24–25 (1990).
Murray, V., *Improved Double–Stranded DNA Sequencing Using the Linear Polymerase Chain Reaction*, Nucleic Acids Research, vol. 17, p. 8889 (1989).
Dower et al., *High Efficiency Transformation of E. Coli by High Voltage Electroporation*, Nucleic Acids Research, V. 16, No. 13, pp. 6127–6145 (1988).
Potter, H., *Electroporation in Biology: Methods, Applications, and Instrumentation*, Analytical Biochemisty, V. 174, No. 2, pp. 361–373 (1988).
de Mendoza D. et al., *Thermal Regulation of Membrane Fluidity in Escherichia Coli*, The Journal of Biological Chemistry, V. 258, No. 4, pp. 2098–2101 (1983).
Hanahan, D., *Studies on Transformation of Escherichia Coli with Plasmids*, Journal of Molecular Biology, V. 166, No. 4, pp. 557–580 (1983).
Ulrich, A.K. et al., *Genetic and Biochemical Analyses of Escherichia Coli Mutants Altered in the Temperature–Dependent Regulation of Membrane Lipid Composition*, Journal of Bacteriology, V. 154, No. 1, pp. 221–230 (1983).
Newman, T. et al., *Cloning and Expression of the ilvB Gene of Escherichia coli K–12*, , Molecular & General Genetics Journal, V. 186, No. 3, pp. 378–384 (1982).
Zimmermann, U. et al., *Electric Field–Induced Cell–to–Cell Fusion*, The Journal of Membrance Biology, V. 67, No. 3, pp. 165–182 (1982).
Danilevskaya, O. No. et al, *Curing of Escherichia coil K12 Plasmids by Coumermycin*, Molecular & General Genetics, V. 178, pp. 233–235 (1980).

(List continued on next page.)

*Primary Examiner*—Johnny F. Railey, II
*Attorney, Agent, or Firm*—Howrey & Simon; Jeffrey Auerbach; Kevin McCabe

[57] ABSTRACT

The invention relates to improved *E. coli* bacteria with enhanced viability at low temperatures, methods for producing improved bacterial strains capable of enhanced viability at low temperatures, and the isolation and use of genetic material capable of enhancing the viability of bacteria at low temperatures. In addition to the enhanced viability at low temperatures, the bacteria may exhibit enhanced transformation efficiencies after storage at low temperatures. As such, the invention may be used for the insertion of exogenous DNA sequences into the bacteria of the invention.

16 Claims, 32 Drawing Sheets

OTHER PUBLICATIONS

Dagert M. et al., *Prolonged Incubation in Calcium Chloride Improves the Competence of Escherichia Coli Cells,* Gene, V. 6, No. 1, pp. 23–28 (1979).

Boyer, H.W. et al., *An Improved Method for Transformation of Escherichia Coli with ColEl Derived Plasmids,* Proceedings of the International Symposium on Genetic Engineering: Scienctific Developements and Practical Applications held in Milan, Italy, Genetic Engineering, pp. 17–23 (1978).

Norgard, M. et al., *Factors Affecting the Transformation of Escherichi aColi Strain $_x1776$ By pBB322 Plasmid DNA,* Gene, V. 3, No. 4, pp. 279–292 (1978).

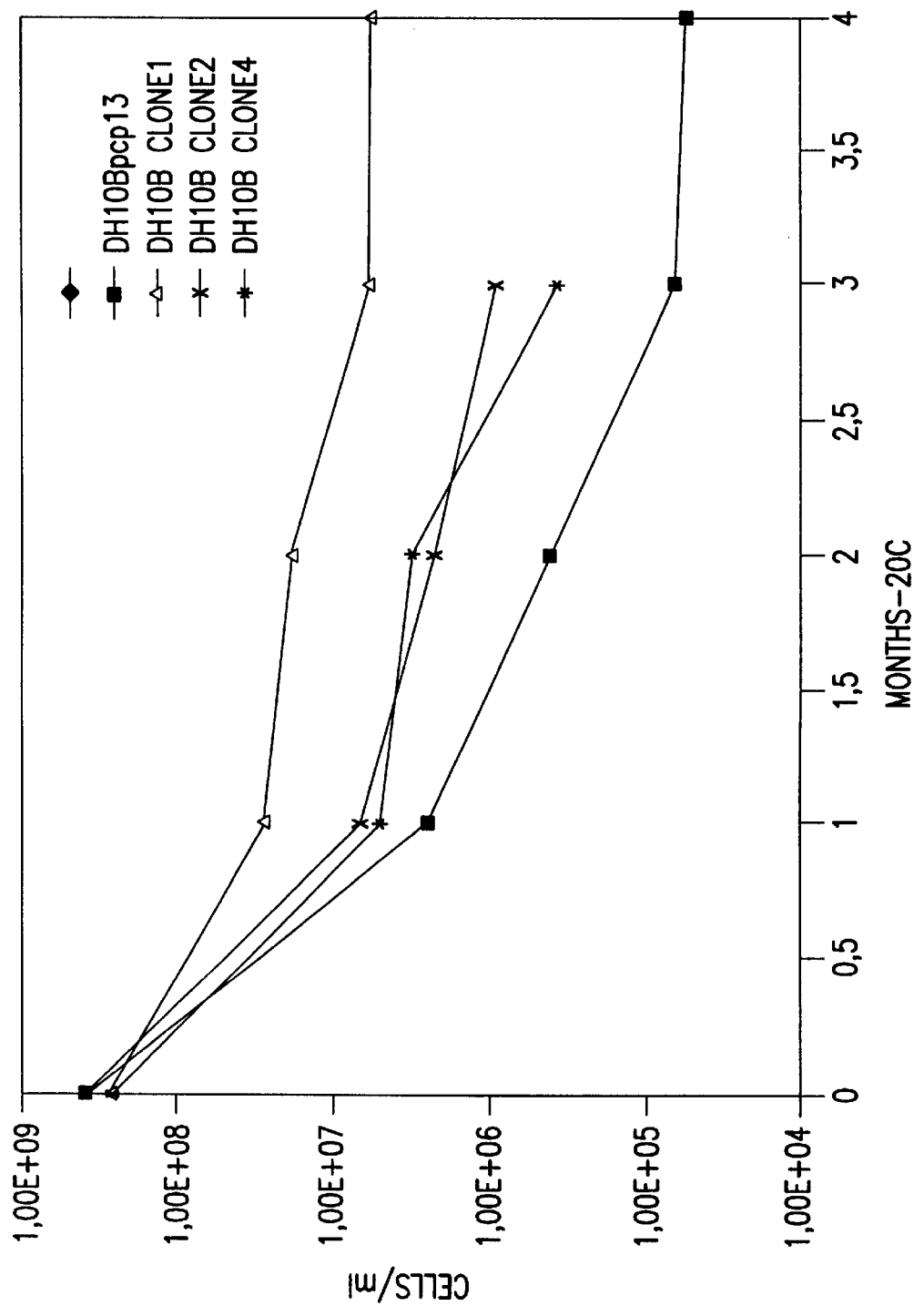

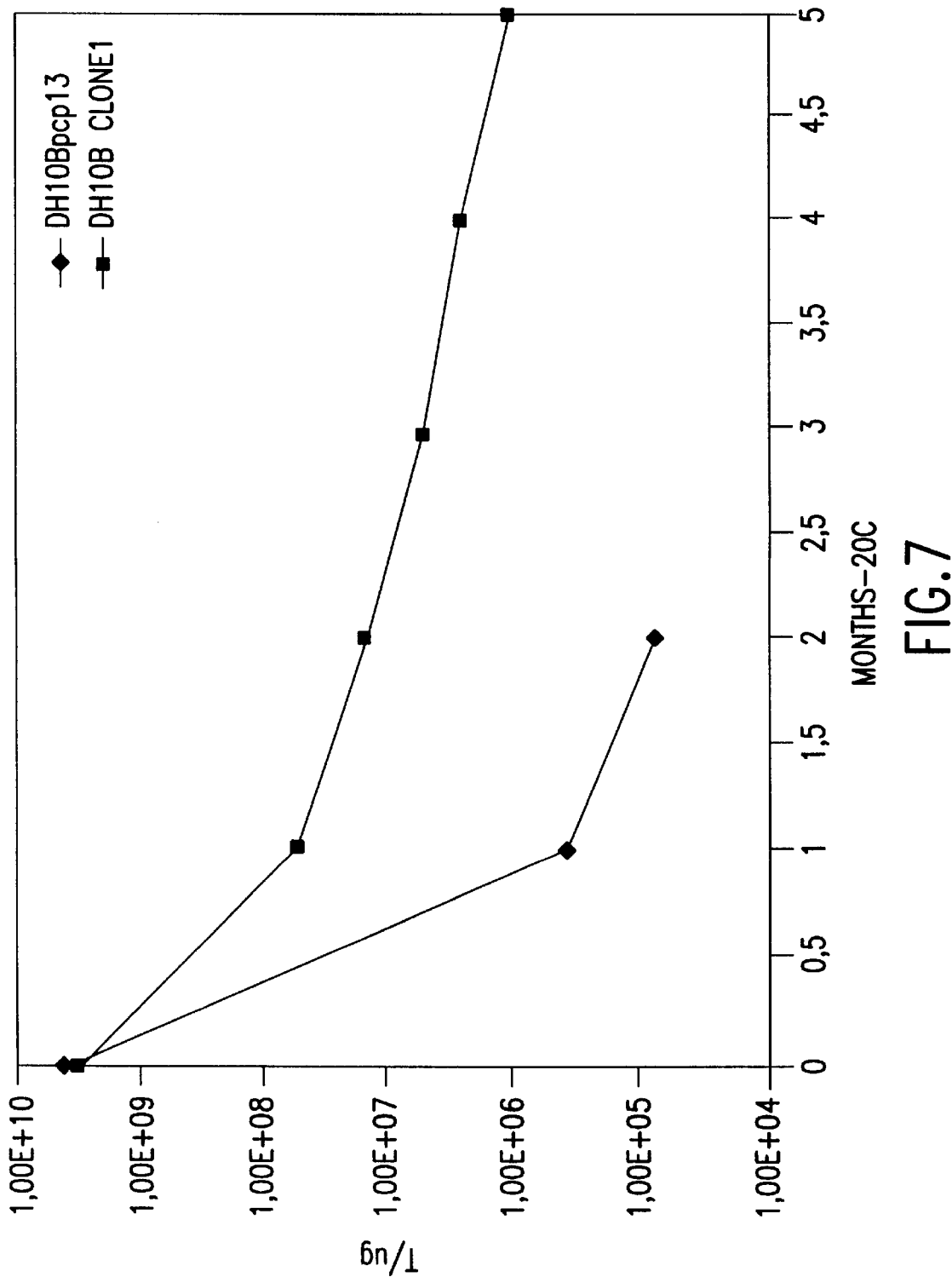

| Sequence | Position |
|---|---|
| CGTAGNTTTCGTTNCATTGGCCCTCAAACCCCTAATAGCGCCAGCGACAA | 50 |
| CAACGCGCTGGCAATACCACCGCCGATAATCGCCGCTTCCCGTTTGCTGC | 100 |
| TGCCCGTGCGGTTAAACCACGGCGCGGAGCAGGGGAGCGGTAATGTCTGT | 150 |
| TCCATCACCCCGCAAAGCATTTCCCGTTTGCGCCCAAAGCCCTTACGTTT | 200 |
| TTGCATCGTGAATCCGGCGTCCTGCAAACCGCGGCGGACAAAACCGGCAG | 250 |
| ACGTAAATGTCGCCAGCGTGCCGCCCGGACGCGCCAACCTTGCCATGGCG | 300 |
| TTAAACAGATTTTGCGTCCACATATCCGGGTTTTTCGCTGGCGCAAAGCC | 350 |
| GTCCAGAAACCAGGCATCTACTTTTTGATTTAGCGAATCGTCCAGTTGGC | 400 |
| TGGTCAGTTCGTTAATATCGCCAAACCATAAATCCAGCGTCACGCGGCCT | 450 |
| TCATCGAGCAATAAACGATGGCAACCGGGCAAGGGCATTGGCCACTGCGC | 500 |
| CTGAAGTTGTTCTGCCCACGGAGCCAGTTCCGGCCAGTGTTGATGCGCTA | 550 |
| AGGCTAAATCCGCACGGGTGAGGGGAAATTTCTCAAAACTAATGAAATGT | 600 |
| AAGCGTTGTAATTGCGCTTGCGGATGCGCTTCGCGAAACTGATCAAATGC | 650 |
| CTGCCATAGCGTCAGGAAGTTTAATCCGGTGCCGAAGCCGCTCTCTGCTA | 700 |
| CCACAAACAGAGGATGTGGATGCTCAGGAAAGCGTACCTCTAATTGGTTG | 750 |
| CCTCCCAGAAAAACATAACGCGTCTCTTCCAGCCCGTTATCGTTGGAAAA | 800 |
| ATAGACATCGTCAAAATCTCGGGAAACAGGTGTACCCTCAGCATTAAATT | 850 |
| CGAGGTTGGCAGGTTGTATGGAGTAGTGTTTCACGTAAGTTACTCGTCTT | 900 |
| ACAGGCGGTGGCTCGATCTTAGCGATGTGTGTAAGGCTGCGCAAATTTCT | 950 |
| CTATTAAATGGCTGATCGGACTTGTTCGGCGTACAAGTGTACGCTATTGT | 1000 |
| GCATTCGAAACTTACTCTATGTGCGACTTACAGAGGTATTGAATGAAACG | 1050 |
| TGCAGTGATTACTGGCCTGGGCATTGTTTCCAGCATCGGTAATAACCAGC | 1100 |
| AGGAAGTCCTGGCATCTCTGCGTGAAGGACGTTCAGGGATCACTTTCTCT | 1150 |
| CAGGAGCTGAAGGATTCCGGCATGCGTAGCCACGTCTGGGGCAACGTAAA | 1200 |
| ACTGGATACCACTGGCCTCATTGACCGCAAAGTTGTGCGCTTTATGAGCG | 1250 |

FIG.13A

| | |
|---|---|
| ACGCATCCATTTATGCATTCCTTTCTATGGAGCAGGCAATCGCTGATGCG | 1300 |
| GGCCTCTCTCCGGAAGCTTACCAGAATAACCCGCGCGTTGGCCTGATTGC | 1350 |
| AGGTTCCGGCGGCGGCTCCCCGCGTTTCCAGGTGTTCGGCGCTGACGCAA | 1400 |
| TGCGCGGCCCGCGCGGCCTGAAAGCGGTTGGCCCGTATGTGGTCACCAAA | 1450 |
| GCGATGGCATCCGGCGTTTCTGCCTGCCTCGCCACCCCGTTTAAAATTCA | 1500 |
| TGGCGTTAACTACTCCATCAGCTCCGCGTGTGCGACTTCCGCACACTGTA | 1550 |
| TCGGTAACGCAGTAGAGCAGATCCAACTGGGCAAACAGGACATCGTGTTT | 1600 |
| GCTGGCGGCGGCGAAGAGCTGTGCTGGGAAATGGCTTGCGAATTCGACGC | 1650 |
| AATGGGTGCGCTGTCTACTAAATACAACGACACCCCGGAAAAAGCCTCCC | 1700 |
| GTACTTACGACGCTCACCGTGACGGTTTCGTTATCGCTGGCGGCGGCGGT | 1750 |
| ATGGTAGTGGTTGAAGAGCTGGAACACGCGCTGGCGCGTGGTGCTCACAT | 1800 |
| CTATGCTGAAATCGTTGGCTACGGCGCAACCTCTGATGGTGCAGACATGG | 1850 |
| TTGCTCCGTCTGGCGAAGGCGCAGTACGCTGCATGAAGATGGCGATGCAT | 1900 |
| GGCGTTGATACCCCAATCGATTACCTGAACTCCCACGGTACTTCGACTCC | 1950 |
| GGTTGGCGACGTGAAAGAGCTGGCAGCTATCCGTGAAGTGTTCGGCGATA | 2000 |
| AGAGCCCGGCGATTTCTGCAACCAAAGCCATGACCGGTCACTCTCTGGGC | 2050 |
| GCTGCTGGCGTACAGGAAGCTATCTACTCTCTGCTGATGCTGGAACACGG | 2100 |
| CTTTATCGCCCCGAGCATCAACATTGAAGAGCTGGACGAGCAGGCTGCGG | 2150 |
| GTCTGAACATCGTGACCGAAACGACCGATCGCGAACTGACCACCGTTATG | 2200 |
| TCTAACAGCTTCGGCTTCGGCGGCACCAACGCCACGCTGGTAATGCGCAA | 2250 |
| GCTGAAAGATTAATTCGCAGTAGGTCGGAGTAGACGCGCCAGCCTCGCAT | 2300 |
| CCGACGTTACGCGCCAATGCGGCCTCCGGCACTAACGCAAAAGGGAACCT | 2350 |
| GATGGTTCCCTTTTTCACATCATTGACAATCGCCGCCAGTTCCAGGCAAA | 2400 |
| CTTCCCGCTTTGTCGATTTCCTTCTGAAAAGACGTACGCGTTAAATCCTG | 2450 |
| CCAACGCACCGTAACCCTGAAACCAGAGAGATGAGACGGGGATACTCCTC | 2500 |

FIG. 13B

```
GCCTTGCGCTGCATTCTGGAGTAATGCATGACTGCTGTAAGCCAAACCGA    2550

AACACGATCTTTCTGCCAATTTTTCGCTYTTTCCGCATCGCTTTTTGCGG    2600

TTTTTCTTCACCTACATGACCCGTAGGGTTGCCGTTGCCGGTTATCCCGC    2650

TGTTTGTT                                              2658
```

FIG.13C

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CGACTCACTA TAGGGAACTG ATCCT                          2 5

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GATTTAGGTG ACACTATAGA GATCC                          2 5

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CCACATATCC GGGTTTTTCG CTG                            2 3

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GAGGTTGGCA GGTTGTATGG AGT    23

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TATGGAGCAG GCAATCGCTG ATG    23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CGTGAAGTGT TCGGCGATAA GAG    23

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AATGCGGCCT CCGGCACTAA CAC    23

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GGTTACGGTG CGTTGGCAGG ATT    23

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TATCAACGCC ATGCATCGCC ATC    23

( 2 ) INFORMATION FOR SEQ ID NO:10:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

```
ACTCCATACA ACCTGCCAAC CTC                                                  23
```

( 2 ) INFORMATION FOR SEQ ID NO:11:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

```
CTGGCGGCGG CGAAGAG                                                         17
```

( 2 ) INFORMATION FOR SEQ ID NO:12:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

```
AAATGGCTGA TCGGACTTGT T                                                    21
```

( 2 ) INFORMATION FOR SEQ ID NO:13:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

```
TCCGGGGTGT CGTTGTATT                                                       19
```

( 2 ) INFORMATION FOR SEQ ID NO:14:

( i ) SEQUENCE CHARACTERISTICS:
    ( A ) LENGTH: 2658 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

```
CGTAGNTTTC GTTNCATTGG CCCTCAAACC CCTAATAGCG CCAGCGACAA CAACGCGCTG          60
GCAATACCAC CGCCGATAAT CGCCGCTTCC CGTTTGCTGC TGCCCGTGCG GTTAAACCAC         120
GGCGCGGAGC AGGGGAGCGG TAATGTCTGT TCCATCACCC CGCAAAGCAT TTCCCGTTTG         180
CGCCCAAAGC CCTTACGTTT TTGCATCGTG AATCCGGCGT CCTGCAAACC GCGGCGGACA         240
AAACCGGCAG ACGTAAATGT CGCCAGCGTG CCGCCCGGAC GCGCCAACCT TGCCATGGCG         300
TTAAACAGAT TTTGCGTCCA CATATCCGGG TTTTTCGCTG GCGCAAAGCC GTCCAGAAAC         360
CAGGCATCTA CTTTTTGATT TAGCGAATCG TCCAGTTGGC TGGTCAGTTC GTTAATATCG         420
CCAAACCATA AATCCAGCGT CACGCGGCCT TCATCGAGCA ATAAACGATG GCAACCGGGC         480
AAGGGCATTG GCCACTGCGC CTGAAGTTGT TCTGCCCACG GAGCCAGTTC CGGCCAGTGT         540
```

```
TGATGCGCTA AGGCTAAATC CGCACGGGTG AGGGGAAATT TCTCAAAACT AATGAAATGT      600
AAGCGTTGTA ATTGCGCTTG CGGATGCGCT TCGCGAAACT GATCAAATGC CTGCCATAGC      660
GTCAGGAAGT TTAATCCGGT GCCGAAGCCG CTCTCTGCTA CCACAAACAG AGGATGTGGA      720
TGCTCAGGAA AGCGTACCTC TAATTGGTTG CCTCCCAGAA AAACATAACG CGTCTCTTCC      780
AGCCCGTTAT CGTTGGAAAA ATAGACATCG TCAAAATCTC GGGAAACAGG TGTACCCTCA      840
GCATTAAATT CGAGGTTGGC AGGTTGTATG GAGTAGTGTT TCACGTAAGT TACTCGTCTT      900
ACAGGCGGTG GCTCGATCTT AGCGATGTGT GTAAGGCTGC GCAAATTTCT CTATTAAATG      960
GCTGATCGGA CTTGTTCGGC GTACAAGTGT ACGCTATTGT GCATTCGAAA CTTACTCTAT     1020
GTGCGACTTA CAGAGGTATT GAATGAAACG TGCAGTGATT ACTGGCCTGG GCATTGTTTC     1080
CAGCATCGGT AATAACCAGC AGGAAGTCCT GGCATCTCTG CGTGAAGGAC GTTCAGGGAT     1140
CACTTTCTCT CAGGAGCTGA AGGATTCCGG CATGCGTAGC CACGTCTGGG CAACGTAAA      1200
ACTGGATACC ACTGGCCTCA TTGACCGCAA AGTTGTGCGC TTTATGAGCG ACGCATCCAT     1260
TTATGCATTC CTTTCTATGG AGCAGGCAAT CGCTGATGCG GGCCTCTCTC CGGAAGCTTA     1320
CCAGAATAAC CCGCGCGTTG GCCTGATTGC AGGTTCCGGC GGCGGCTCCC CGCGTTTCCA     1380
GGTGTTCGGC GCTGACGCAA TGCGCGGCCC GCGCGGCCTG AAAGCGGTTG GCCCGTATGT     1440
GGTCACCAAA GCGATGGCAT CCGGCGTTTC TGCCTGCCTC GCCACCCCGT TTAAAATTCA     1500
TGGCGTTAAC TACTCCATCA GCTCCGCGTG TGCGACTTCC GCACACTGTA TCGGTAACGC     1560
AGTAGAGCAG ATCCAACTGG GCAAACAGGA CATCGTGTTT GCTGGCGGCG GCGAAGAGCT     1620
GTGCTGGGAA ATGGCTTGCG AATTCGACGC AATGGGTGCG CTGTCTACTA AATACAACGA     1680
CACCCCGGAA AAAGCCTCCC GTACTTACGA CGCTCACCGT GACGGTTTCG TTATCGCTGG     1740
CGGCGGCGGT ATGGTAGTGG TTGAAGAGCT GGAACACGCG CTGGCGCGTG GTGCTCACAT     1800
CTATGCTGAA ATCGTTGGCT ACGGCGCAAC CTCTGATGGT GCAGACATGG TTGCTCCGTC     1860
TGGCGAAGGC GCAGTACGCT GCATGAAGAT GGCGATGCAT GGCGTTGATA CCCCAATCGA     1920
TTACCTGAAC TCCCACGGTA CTTCGACTCC GGTTGGCGAC GTGAAAGAGC TGGCAGCTAT     1980
CCGTGAAGTG TTCGGCGATA AGAGCCCGGC GATTTCTGCA ACCAAAGCCA TGACCGGTCA     2040
CTCTCTGGGC GCTGCTGGCG TACAGGAAGC TATCTACTCT CTGCTGATGC TGGAACACGG     2100
CTTTATCGCC CCGAGCATCA ACATTGAAGA GCTGGACGAG CAGGCTGCGG GTCTGAACAT     2160
CGTGACCGAA ACGACCGATC GCGAACTGAC CACCGTTATG TCTAACAGCT TCGGCTTCGG     2220
CGGCACCAAC GCCACGCTGG TAATGCGCAA GCTGAAAGAT TAATTCGCAG TAGGTCGGAG     2280
TAGACGCGCC AGCCTCGCAT CCGACGTTAC GCGCCAATGC GGCCTCCGGC ACTAACGCAA     2340
AAGGGAACCT GATGGTTCCC TTTTTCACAT CATTGACAAT CGCCGCCAGT TCCAGGCAAA     2400
CTTCCCGCTT TGTCGATTTC CTTCTGAAAA GACGTACGCG TTAAATCCTG CCAACGCACC     2460
GTAACCCTGA AACCAGAGAG ATGAGACGGG GATACTCCTC GCCTTGCGCT GCATTCTGGA     2520
GTAATGCATG ACTGCTGTAA GCCAAACCGA AACACGATCT TTCTGCCAAT TTTTCGCTYT     2580
TTCCGCATCG CTTTTTGCGG TTTTTCTTCA CCTACATGAC CCGTAGGGTT GCCGTTGCCG     2640
GTTATCCCGC TGTTTGTT                                                   2658
```

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (x i) SEQUENCE DESCRIPTION: SEQ ID NO:15:

TAAATTCGAG GTTGGCAGGT T                                                                          21

(2) INFORMATION FOR SEQ ID NO:16:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (x i) SEQUENCE DESCRIPTION: SEQ ID NO:16:

AATCGACAAA GCGGGAAGTT                                                                            20

(2) INFORMATION FOR SEQ ID NO:17:

(i) SEQUENCE CHARACTERISTICS:
      (A) LENGTH: 129 base pairs
      (B) TYPE: nucleic acid
      (C) STRANDEDNESS: single
      (D) TOPOLOGY: linear (i i) MOLECULE TYPE: cDNA (x i) SEQUENCE DESCRIPTION: SEQ ID NO:17:

CTCTCTGGGC GCTGCTGGCG TACAGGAAGC TATCTACTCT CTGCTGATGC TGGAACACGG    60

CTTTATCGCC CCGAGCATCA ACATTGAAGA GCTGGACGAG CAGGCTGCGG GTCTGAACAT   120

CGTGACCGA                                                                                       129

METHOD FOR INCREASING THE VIABILITY AND TRANSFORMATION ABILITY OF BACTERIA DURING OR AFTER STORAGE AT LOW TEMPERATURES

CROSS REFERENCES TO RELATED APPLICATIONS

This application is a continuation-in-part of U.S. Provisional Application No. 60/014,330, filed Mar. 29, 1996, and U.S. Provisional Application No. 60/025,838, filed Sep. 5, 1996. Both applications are herein incorporated by reference.

FIELD OF THE INVENTION

The invention relates to stable storage of bacteria at low temperatures (e.g., about 4° C. to about −20° C.). Specifically, the invention relates to improved bacteria having enhanced viability or enhanced transformation efficiency during storage at low temperatures, methods for producing such bacteria, and the genetic material involved in such enhancement. The invention further relates to such cells made competent for transformation, to methods for making such competant cells, and to methods of transforming such competent cells.

BACKGROUND OF THE INVENTION

Extended storage of bacteria is typically accomplished at very low temperatures (−80° C. and below). Not only have such very low temperatures been used to store bacteria, but they have also been used to store bacteria made competent for transformation (U.S. Pat. No. 4,981,797). However, problems are associated with the storage of bacteria and competent bacterial cells at higher temperatures (e.g., about −20° C. to about 4° C.). At these higher temperatures, bacteria and competent bacterial cells rapidly lose viability and transformation efficiency. Over a period of several months, the viable cell count and the transformation efficiency of such cells decreases by several orders of magnitude. Bacteria which are competent for transformation can only be stored at 4° C. for several days (Dagent et al., Gene 6:23–28 (1979)) or for a period of up to 16 days (Pope et al., Nucl. Acids Res. 24(3):536–537 (1996)). Thus, in order to maintain viability and competency, bacteria and competent bacterial cells have typically been stored at −80° C.

Stable storage of bacteria, and particularly competent cells, at temperatures higher than −80° C. is highly desirable, since many research laboratories may not have access to very low temperature storage. Moreover, the cost of storing bacteria at −80° C. is greater than at higher temperatures, and it is both difficult and expensive to transport bacterial cells at temperatures lower than −20° C.

SUMMARY OF THE INVENTION

The present invention provides a method which allows bacterial cells and competent cells to be stored for extended periods of time at temperatures greater than −80° C. (e.g., about −20° C. to about 4° C.) without appreciably losing transformation efficiency or viability. Thus, the method of the invention provides bacterial cells and competent cells which do not require specialized storage conditions (e.g., extremely low temperatures) to maintain the viability and/or transformation efficiency of such cells.

The method of the invention specifically comprises altering the fatty acid content of the bacteria. Preferably, the unsaturated fatty acid content of the bacteria is altered in accordance with the invention. Preferably, one or more of the fatty acids is increased in the bacteria, and most preferably the fatty acid content is in the bacterial membrane. Preferred methods of altering the fatty acid content includes genetic alteration of the bacteria (e.g. by enhancing expression of one or more genes involved in production (synthesis or catabolism) of one or more fatty acids). Bacteria used according to the invention include both gram positive and gram negative bacteria, although gram negative bacteria such as *Escherichia* are preferred. Particularly preferred bacteria include *Escherichia coli*.

The invention also relates to bacteria having enhanced viability and/or enhanced transformation efficiency after periods of storage at low temperatures (e.g., greater than −80° C., preferably about −20° C. to about 4° C.). Such storage stable cells comprise an altered fatty acid content. Preferably, the storage stable bacterial cells or competent cells have an increased level or amount of one or more fatty acids, preferably unsaturated fatty acids. Such increased amount of fatty acid content may be caused by genetic alterations, preferably by enhancing expression of one or more genes involved in changing the fatty acid content of the bacteria.

The invention also relates to methods of making the bacteria of the invention competent, to methods of transforming such competent bacterial strains of the invention, and to the bacterial cells of the invention transformed with exogenous DNA. According to the invention, exogenous DNA sequences (e.g., plasmids, cosmids, DNA libraries, cDNA libraries, expression vectors, eukaryotic (particularly mammalian, and most particularly human) DNA, phage DNA, etc.) may be transformed into the novel bacteria of the invention by any of a variety of techniques, including, but not limited to, chemical-mediated transformation, electroporation, and liposome-mediated transformation.

The invention further provides a DNA molecule comprising a sequence capable of enhancing the viability or the transformation efficiency of a bacterium at low temperatures (e.g., greater than −80° C., preferably about −20° C. to about 4° C.). Such DNA molecule preferably comprises one or more genes involved in the production of one or more fatty acids in the bacteria. Most preferably, the nucleic acid molecule of the invention allows enhanced production of fatty acids in the bacteria.

BRIEF DESCRIPTION OF THE DRAWINGS

FIG. 4A shows the viable cell counts of DH10B cells containing vector pCP13 and cosmids 1, 2 and 4 over a period of 4 months during which the cells are stored at −20° C.

FIG. 7 shows the transformation efficiencies of the DH10B strain containing cosmid clone 1, and the DH10B strain containing vector pCP13, both stored at −20° C. for 5 months.

FIG. 13 shows DNA sequence (SEQ ID NO: 14) of the essential region of cosmid clone 1 (2658 bp).

DETAILED DESCRIPTION OF THE INVENTION

Definitions

Figure 1:
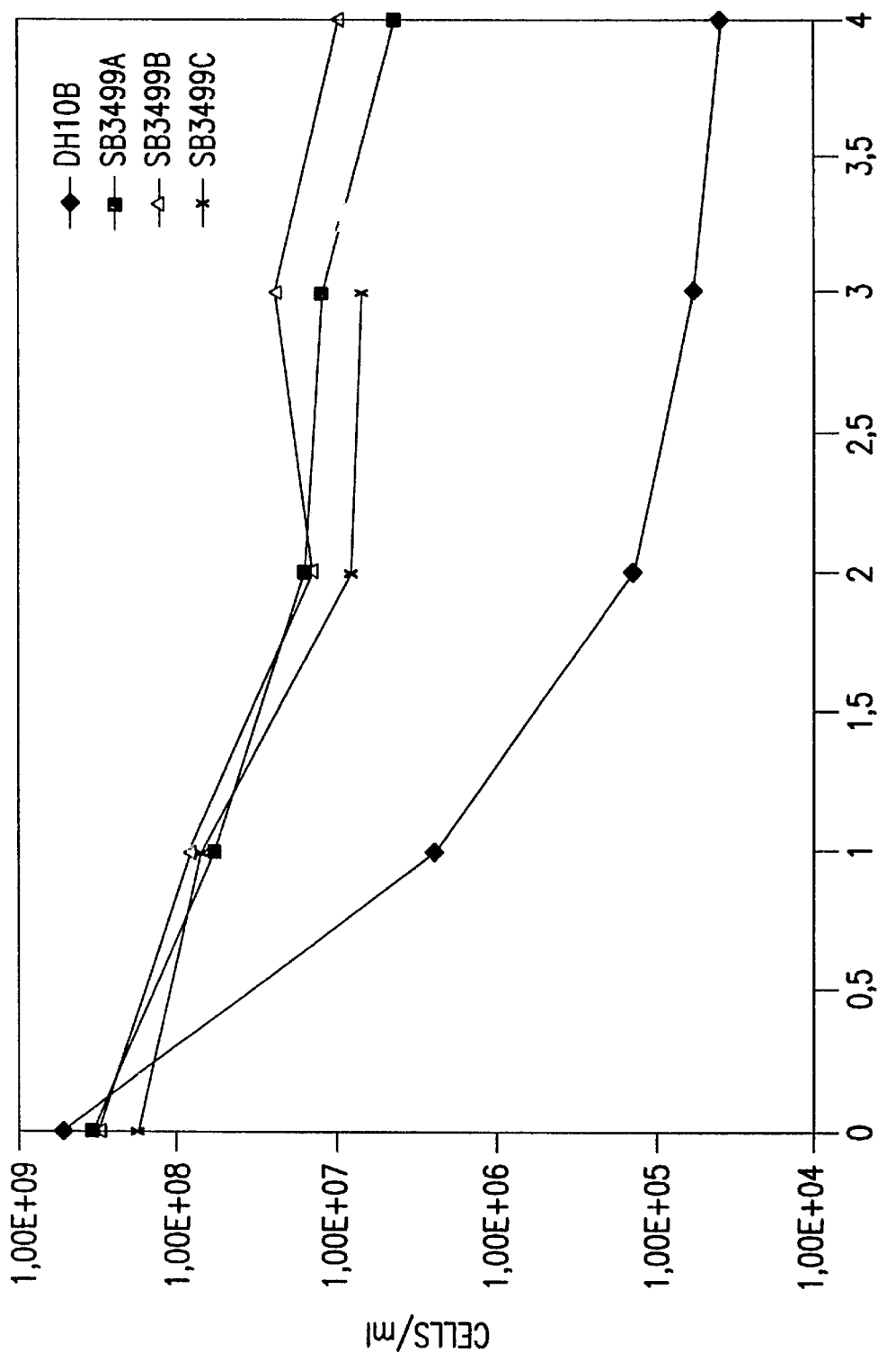
FIG. 1 shows the viability of *E. coli* DH10B, SB3499A, SB3499B, and SB3499C expressed in terms of cells/ml and after storage of the cells at 20° C.

In the description that follows, a number of terms used in recombinant DNA technology are utilized extensively. In order to provide a clear and consistent understanding of the specification and claims, including the scope to be given such terms, the following definitions are provided.

DNA Molecule. Any DNA molecule, of any size, from any source, including DNA from viral, prokaryotic, and eukaryotic organisms. The DNA molecule may be in any form, including, but not limited to, linear or circular, and single or double stranded. Non-limiting examples of DNA molecules include plasmids, vectors, and expression vectors.

Cloning vector. A plasmid, phage DNA, a cosmid, or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of expressing a gene which has been cloned into it, after transformation into a host. The cloned gene is usually placed under the control of (i.e., operably linked to) certain control sequences such as promoter sequences.

Storage Stable. Within the meaning of the present invention, bacterial cells and/or competent bacterial cells which are "storage stable" are able to withstand storage for extended periods of time at a suitable temperature, without appreciably losing their transformation efficiency and/or viability. By the term "without appreciably losing their transformation efficiency and/or viability" is meant that the cells maintain about 40% to 100%, preferably 60% to 100%, more preferably 70% to 100%, and most preferably about 80% to 100% of their original transformation efficiency and/or viability during a storage period of 30 days, preferably 60 days, more preferably 90 days, and most preferably 120 days, at a temperature of −20° C. Suitable storage temperatures for the bacterial cells or competent bacterial cells of the invention vary from about room temperature to about −180° C. Preferably, the storage temperature ranges from about 4° C. to about −80° C., more preferably from about −20° C. to about 4° C. In a preferred aspect of the invention, the cells are stored at about −20° C. The storage period or time may range from about 0 days to about 180 days (e.g., 6 months), preferably from about 0 days to about 120 days (e.g., 4 months), and more preferably from about 0 days to about 90 days (e.g., 3 months), although longer storage times may be used at temperatures of about −20° C. and below.

Fatty Acids. Any fatty acid which is saturated or unsaturated. Unsaturated fatty acids including monoenic acids, dienoic acids and higher unsaturated fatty acids (e.g., tri, tetra, penta and hexaenoic acids etc.). Examples of unsaturated fatty acids include but are not limited to oleic acid, linoleic acid, linolenic acid, cis vaccenic acid, arachidonic acid, palmitoleic acid etc. Examples of saturated fatty acids include butyric acid, lauric acid, palmitic acid and stearic acid. Preferred fatty acids in accordance with the invention are unsaturated fatty acid, most preferably cis vaccenic acid and palmitoleic acid.

Competent cells. Cells having the ability to take up and establish an exogenous DNA molecule.

The present invention relates to a method for enhancing viability or transformation efficiency of a bacterium by altering the fatty acid content (preferably the unsaturated fatty acid content). The invention also relates to a method for obtaining a bacterium having such an altered fatty acid content. The method involves modifying or mutating a bacterium such that the fatty acid content of said bacterium is altered relative to an unmodified or unmutated bacterium. The modified or mutated bacterium having enhanced viability or enhanced transformation efficiency may then be isolated. Selection of such a modified bacterium may be selected by assaying for such enhanced characteristics relative to the unmodified bacterium (see Examples). Preferably, the amount of fatty acid is increased in the bacterium. This increase may be accomplished by various techniques, for example, by adding one or more fatty acids to the bacterium or by genetically modifying the bacterium. Any type of genetic modification may be used in accordance with the invention, including natural selection, artificial mutation and genetic engineering. Such techniques are well known in the art. Common genetic engineering techniques include cloning one or more fatty acid genes in a vector to increase copy number, or enhancing translation or transcription of such genes by, for example, overexpression (e.g., using an expression vector).

The method of the invention provides for the production of cells which have enhanced viability and/or enhanced transformation efficiency upon storage at low temperatures (e.g., greater than −80° C., preferably about −20° C. to about 4° C.). Such storage stable strains may be stored for extended periods at various temperatures. According to the invention, alteration of the content of one or more fatty acids results in enhanced viability or enhanced transformation efficiency. Alteration of the fatty acid content can be accomplished in any bacteria to provide bacteria having these beneficial characteristics. Preferably, such bacteria are modified genetically.

Both gram negative and gram positive prokaryotic cells (e.g., bacteria) can be used in accordance with the invention. Examples of suitable prokaryotic cells include, but are not limited to, *Escherichia* sp., *Klebsiella* sp., *Salmonella* sp., *Bacillus* sp., *Streptomyces* sp., *Streptococcus* sp., *Shigella* sp., *Staphylococcus* sp., and *Pseudomonas* sp. Non-limiting examples of species within each aforementioned genus that can be used in accordance with the invention include *Escherichia coli, Klebsiella pneumoniae, Bacillus subtilis, Salmonella typhimurium, Streptomyces aureus, Streptococcus mutans, Streptococcus pneumoniae,* and *Pseudomonas syringae.*

In a preferred embodiment, the cells which can be used in the invention are *Escherichia*, most preferably *E. coli*. Non-limiting examples of *E. coli* strains include DH5, DH5a, DH10, DH10B, HB101, RR1, JV30, DH11S, DM1, DH10B/p3, DH5αMCR, DH5αF'IQ, DH5αF', SCS1, Stb1-2, DH12S, DH5α-E, DH10BAC, XL1-Blue MRF, XL2-Blue MRF, XL1-Blue MR, SURE Strain, SURE 2 Strain, XL1-Blue, XL2-Blue, AG1, JM101, JM109, JM110/SCS110, NM522, TOPP Strains, ABLE Strains, XL1-Red, BL21 Strains, BJS183 TK B1 Strain, and derivatives thereof.

As used herein, a "derivative" of a specified bacterium is a progeny or other recipient bacterium that contains genetic material obtained directly or indirectly from the specified bacterium. Such derivative bacterium may, for example, be formed by removing genetic material from a specified bacterium and subsequently introducing it into another bacterium (i.e., the progeny or other recipient bacterium) (e.g., via transformation, conjugation, electroporation transduction, etc.). Alternatively, such derivative bacterium may possess genetic material (produced synthetically, via cloning, via in vitro amplification, etc.) having the effective sequence of genetic material of the specified bacterium.

The bacteria of the invention having altered fatty acid content may be made competent for transformation using well known techniques. Such competent bacterial cells have, according to the invention, enhanced transformation efficiency upon or after storage at low temperatures (e.g., greater than −80° C., preferably about −20° C. to about 4° C.). Transformation, in the context of the current invention, is the process by which exogenous DNA is inserted into a bacterium, causing the bacterium to change its genotype and/or phenotype. Such a change in genotype or phenotype may be transient or otherwise. Exogenous DNA is any DNA, whether naturally occurring or otherwise, from any source that is capable of being inserted into any organism. Preferably, exogenous DNA is any DNA, whether naturally occurring or otherwise, from any source that is capable of being inserted into bacteria. Such exogenous DNA includes, without limitation, plasmid DNA, cosmid DNA, eukaryotic (particularly mammalian, and most particularly human) DNA, DNA libraries, cDNA libraries, expression vectors and phage DNA (such as bacteriophage lambda DNA).

A number of procedures exist for the preparation of competent bacteria and the introduction of DNA into those bacteria. A very simple, moderately efficient transformation procedure for use with *E. coli* involves re-suspending log-phase bacteria in ice-cold 50 mM calcium chloride at about $10^{10}$ bacteria/ml and keeping them ice-cold for about 30 min. Plasmid DNA (0.1 mg) is then added to a small aliquot (0.2 ml) of these now competent bacteria, and the incubation on ice continued for a further 30 minutes, followed by a heat shock of 2 minutes at 42° C. The bacteria are then usually transferred to nutrient medium and incubated for some time (30 minutes to 1 hour) to allow phenotypic properties conferred by the plasmid to be expressed, e.g., antibiotic resistance commonly used as a selectable marker for plasmid-containing cells. Protocols for the production of competent bacteria have been described (Hanahan (*J. Mol. Biol.* 166: 557–580 (1983); Liu et al., *Bio Techniques* 8:21–25 (1990); Kushner, In: *Genetic Engineering: Proceedings of the International Symposium on Genetic Engineering*, Elsevier, Amsterdam, pp. 17–23 (1978); Norgard et al., Gene 3:279–292 (1978); Jessee et al., U.S. Pat. No. 4,981,797); Maniatis et al., *Molecular Cloning, A Laboratory Manual*, Cold Spring Harbor Press, Cold Spring Harbor, N.Y. (1982).

Another rapid and simple method for introducing genetic material into bacteria is electoporation (Potter, *Anal. Biochem.* 174: 361–73 (1988)). This technique is based upon the original observation by Zimmerman et al., *J. Membr. Biol.* 67: 165–82 (1983), that high-voltage electric pulses can induce cell plasma membranes to fuse. Subsequently, it was found that when subjected to electric shock (typically a brief exposure to a voltage gradient of 4000–16000 V/cm), the bacteria take up exogenous DNA from the suspending solution, apparently through holes momentarily created in the plasma membrane. A proportion of these bacteria become stably transformed and can be selected if a suitable marker gene is carried on the transforming DNA (Newman et al., *Mol. Gen. Genetics* 197: 195–204 (1982)). With *E. coli*, electoporation has been found to give plasmid transformation efficiencies of $10^9$–$10^{10}$ T/$\mu$g DNA (Dower et al., *Nucleic Acids Res.* 16: 6127–6145 (1988)).

Bacterial cells are also susceptible to transformation by liposomes (Old and Primrose, In: *Principles of Gene Manipulation: An Introduction to Gene Manipulation*, Blackwell Science (1995)). A simple transformation system has been developed which makes use of liposomes prepared from cationic lipid (Old and Primrose, In: *Principles of Gene Manipulation: An Introduction to Gene Manipulation*, Blackwell Science (1995)). Small unilamellar (single bilayer) vesicles are produced. DNA in solution spontaneously and efficiently complexes with these liposomes (in contrast to previously employed liposome encapsidation procedures involving non-ionic lipids). The positively-charged liposomes not only complex with DNA, but also bind to bacteria and are efficient in transforming them, probably by fusion with the cells. The use of liposomes as a transformation or transfection system is called lipofection.

The present invention also concerns genetic material capable of enhancing the viability and/or transformation efficiency of said bacterium at low temperatures. In particular, the invention concerns isolated nucleic acid molecules which allow alteration of fatty acid content when introduced into a bacterium. Preferably, the nucleic acid molecule comprises one or more genes involved in changing fatty acid content of said bacterium. Such genetic material is preferably contained in a cloning or expression vector. In one aspect of the invention, the nucleic acid molecule comprises one or more genes which enhance the level of one or more fatty acids. Preferably, the genes enhance unsaturated fatty acid levels. Such unsaturated fatty acids include, but are not limited to, oleic acid, linoleic acid, linolenic acid, cis vaccenic acid, and palmitoleic acid. Such genes include but are not limited to fabB, fabF, fabD, fabG, fabA, fabH, fabI, fabZ, fadA, fadB, fadE, fadL, fadR, farR, fatA, etc.

The viable cell count of cells produced by the method of the invention will remain at greater than about $1\times10^6$ cells/ml, preferably greater than about $1\times10^7$ cells/ml, more preferably greater than about $1\times10^8$ cells/ml and most preferably greater than $1\times10^9$ cells/ml when stored at $-20°$ C. for any time period from about 0 days to about 1 month, preferably from about 0 days to about 3 months, and more preferably from about 0 days to about 6 months. These cells will retain a transformation efficiency of at least about $1\times10^5$, preferably at least about $1\times10^6$, more preferably at least about $1\times10^7$, still more preferably at least about $1\times10^8$ and most preferably at least about $1\times10^9$ transformants per microgram of DNA (T/$\mu$g). Suitable storage temperatures vary from about room temperature to about $-180°$ C. Preferably, the storage temperature ranges from about $4°$ C. to about $-80°$ C., more preferably from about $-20°$ C. to about $4°$ C. In a preferred aspect of the invention, the cells are stored at about $-20°$ C. The storage period or time may range from about 0 days to about 1 month, preferably from about 0 days to about 3 months, still more preferably from about 0 days to about 6 months, and still more preferably from about 0 days to about 1 year, although longer storage times may be used at temperatures of about $-20°$ C. and below. Competent cells produced by the method of the invention may be stored at $-20°$ C. for at least 3 months while retaining substantially their transformation efficiency. Substantial retention of transformation efficiency means that the cells will have a transformation efficiency after storage that is about 40% to 100%, preferably at about 60% to 100%, more preferably about 70% to 100% and most preferably about 80% to 100% of the transformation efficiency of the competent cells tested prior to storage.

The invention also pertains to transforming the competent bacterial cell produced according to the method of invention. Transforming said competent cells comprises obtaining a competent bacterial cell of the invention, mixing said cell with a DNA molecule, and incubating said mixture under conditions sufficient to transform said cell with said DNA molecule. According to this aspect of the invention, the competent cell may be any gram positive or gram negative bacteria including, but not limited to, *Escherichia, Klebsiella, Salmonella, Bacillus, Streptomyces, Streptococcus,* and *Pseudomonas*. Preferably, gram negative prokaryotic cells are transformed according to the method of the invention, more preferably *Escherichia*, and most preferably *E. coli*. According to the invention, any DNA molecule (e.g., vectors, plasmids, phagemids, expression vectors, etc.) may be used.

After the cells have been transformed with the DNA molecule of interest, the transformed cells may be grown in a growth conducive medium. Typically, such a growth conducive medium contains an antibiotic to assist in selection of transformed cells. That is, the DNA molecule to be transformed may contain a selective marker (e.g., an antibiotic resistance gene), allowing selection of transformed cells when the corresponding antibiotic is used in the medium.

The invention also concerns a method of producing a desired protein by transforming a competent cell of the invention with a DNA molecule encoding said desired protein. Thus, the invention concerns a method of producing a desired protein comprising obtaining a competent cell produced according to the invention, transforming said cell with a DNA molecule capable of expressing said desired protein, and culturing said transformed cell under conditions sufficient to produce said desired protein. Cells which can be used according to this aspect of the invention including both gram negative and gram positive bacteria, preferably *Escherichia*, and most preferably *E. coli*. In this aspect of the invention, the cells are transformed by mixing the cells with a DNA molecule and incubating the mixture under conditions sufficient to transform said cell with said DNA molecule. Transformed cells may be selected according to techniques well known in the art including, for example, selection for marker genes on the DNA molecule (e.g., antibiotic resistance genes). After the transformed cell has been selected, the cell may then be cultured according to well known techniques in a growth conducive medium. Upon culturing the cell under appropriate conditions, the cell is capable of producing the desired protein. The desired protein may then be isolated, and a substantially pure protein obtained by well known protein purification techniques.

Having now generally described the invention, the same will be more readily understood through reference to the following examples which are provided by way of illustration, and are not intended to be limiting of the present invention unless specified. All patents, patent applications and publications mentioned herein are incorporated by reference in their entirety.

EXAMPLE 1

Generation of Mutant Strains by Cycling

A common technique in microbial genetics is the generation of mutant strains of bacteria utilizing recycling. This technique is dependent on a rapid rate of bacterial killing under some unfavorable condition. In this particular case, the storage of E. coli strain DH10B in CCMB80 buffer at −20° C. results in the rapid killing of the strain and the subsequent decrease in the viable cell count over a period of 6 months. The survivors which remain after 6 months storage at −20° C. are again regrown and stored at 20° C. in CCMB80 buffer. After 4 cycles under these particular conditions single colonies are tested for survival at −20° C. The isolated strain was designated SB3499.

EXAMPLE 2

Preparation of Competent Cells

A single colony isolate of E. coli strain DH10B and three single colony isolates of E. coli SB3499 (Example 1) (designated SB3499A (NRRL B-21606), SB3499B (NRRL B-21607), and SB3499C (NRRL B-21608) respectively, each deposited on Aug. 1, 1996, under the terms of the Budapest Treaty governing Microbiological Deposits) were selected. Competent cells of these isolates were made according to the method of Jessee, J. and Bloom, F. R., U.S. Pat. No. 4,981,797, herein incorporated by reference. Essentially the process is as follows: The single colony isolates of DH10B, SB3499A, SB3499B, and SB3499C were each inoculated into 2 ml of 15/10 medium (1.0% Bacto tryptone, 1.5% Bacto yeast extract, 10 mM NaCl, 2 mM KCl, 10 mM $MgCl_2$, 10 mM $MgSO_4$, 0.001% polypropylene glycol (PPG)) and shaken overnight at 275 rpm at a temperature of 30° C. A 0.3 ml aliquot of each overnight culture was used to inoculate a 500 ml baffled flask containing 60 ml 15/10 medium. The resulting cultures were grown by shaking them at 275 rpm at a temperature of 30° C. until the $O.D._{550}$ of the cultures was approximately 0.3. A 50 ml aliquot of the culture was harvested by centrifugation of that aliquot at 2,000 rpm and 4° C., for a sufficient time to pellet the bacterial cells. The bacterial cell pellets were then resuspended in 4 ml of ice cold CCMB80 buffer (10 mM potassium acetate pH 7.0, 80 mM $CaCl_2$, 20 mM $MnCl_2$, 10 mM $MgCl_2$, 10% glycerol adjusted to pH 6.4 with 0.1N HCl, as described in Hanahan, et al., Methods in Enzymology, 204:63–113 (1991), herein incorporated by reference. The resuspended bacterial cells were then kept on ice for 20 minutes. The resuspended bacterial cells were then divided into 250 µl aliquots and frozen in a dry ice/ethanol bath for at least 5 minutes. All but one aliquot of each isolate was stored at −20° C. for a specified period of time prior to a determination of its viability and its transformation efficiency.

EXAMPLE 3

Viability and Transformation Assays

Aliquots containing competent cells prepared according to Example 2 were tested after a specified period of storage at −20° C. to determine the viability and transformation efficiency of that aliquot. Aliquots were either tested immediately or at monthly intervals after storage at −20° C.

To determine the viability of an aliquot, the aliquot was removed from −20° C. and placed on ice for approximately 15 minutes. The aliquot was serially diluted using 0.85% NaCl. Dilutions were then plated on LB agar plates (Gibco/BRL) to determine viable cell counts. FIG. 1 shows the viability of E. coli DH10B, SB3499A, SB3499B, and SB3499C. The viable cell counts of SB3499A, SB3499B and SB3499C were over 100 fold higher than DH10B after these cells were stored for between 2–4 months at −20° C.

Figure 2:
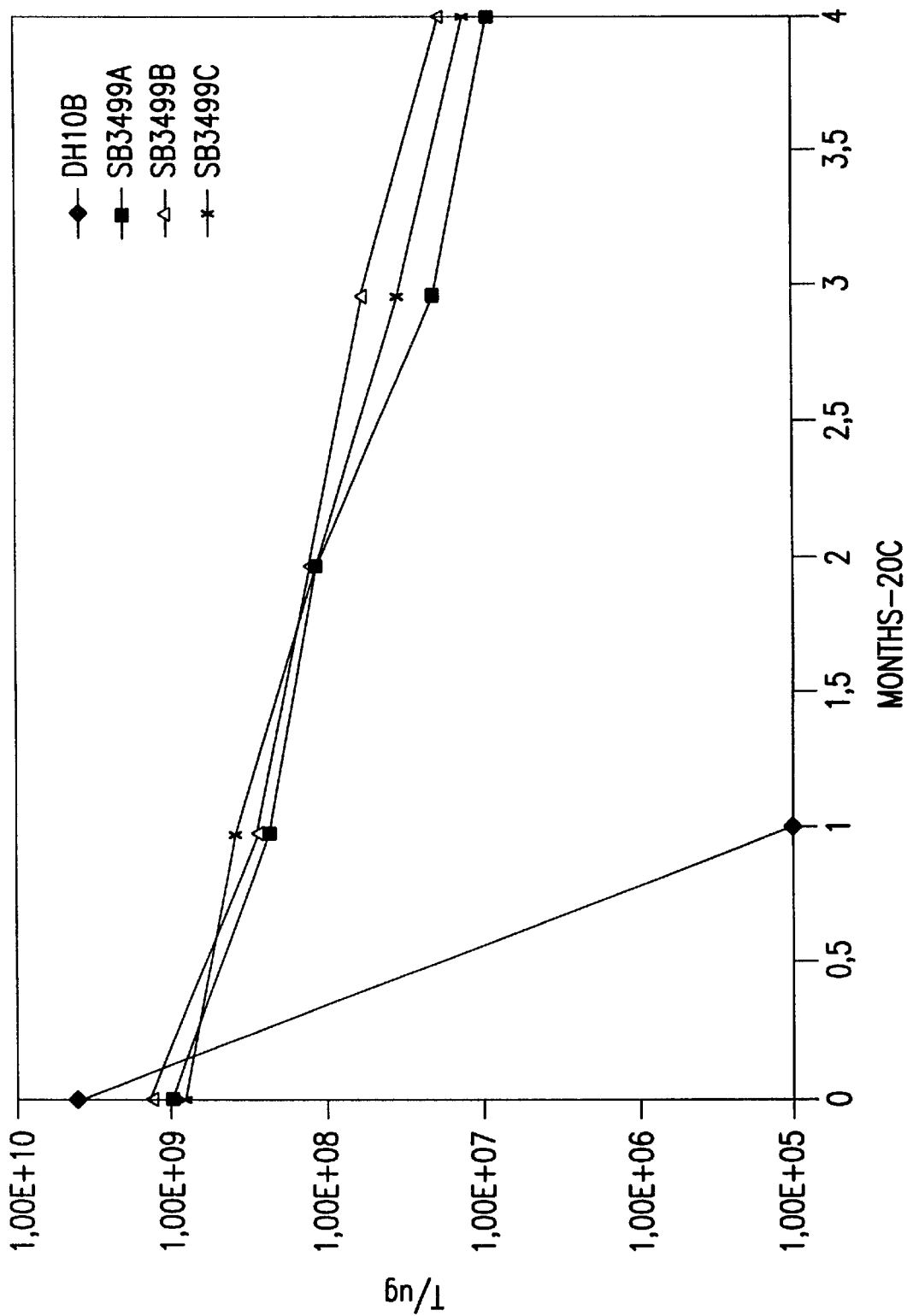
FIG. 2 shows the transformation efficiency of *E. coli* DH10B, SB3499A, SB3499B, and SB3499C expressed in terms of transformants per μg DNA after storage of the cells at −20° C.

To determine the transformation efficiency of an aliquot, the aliquot was removed from −20° C. and placed on ice for approximately 15 minutes. The cells were assayed for transformation efficiency using plasmid pUC19, according to the method of Hanahan, J. Mol. Biol. 166: 577 (1983), herein incorporated by reference. FIG. 2 shows the transformation efficiency of E coli DH10B, SB3499A, SB3499B, and SB3499C expressed in terms of transformants per µg DNA. The transformation efficiency of DH10B cells decreased to less than $1.0 \times 10^5$ transformants/µg DNA after one month of storage at −20° C. The transformation efficiencies of SB3499A, SB3499B, and SB3499C were greater than $3.0 \times 10^6$ transformants/µg DNA after four months of storage at −20° C. Therefore isolates SB3499A, SB3499B and SB3499C exhibit substantially higher viable cell counts and transformation efficiencies than DH10B after prolonged storage at −20° C.

EXAMPLE 4

Genetic Characterization of E coli DH10B, SB3499A, SB3499B, and SB3499C

The SB3499A, SB3499B and SB3499C isolates were evaluated for genetic markers that are characteristic of E. coli DH10B. Table 1 shows the characteristic genetic markers for the SB3499A, SB3499B, and SB3499C isolates of the E. coli strain DH10B. The genetic markers which were evaluated for strains SB3499A, SB3499B and SB3499C are identical to the genetic markers of DH10B. MacConkey galactose plates are made using Difco MacConkey agar containing 1% galactose. X-gal IPTG plates were made using LB agar containing 50 µg/ml X-gal and 1 mM IPTG. Minimal agar plates were made by adding 100 ml of stock I (20 g ammonium chloride, 60 g potassium phosphate (monobasic), and 120 g sodium phosphate (dibasic), diluted to 1 liter with distilled water), 60 ml of stock H (60 g glucose, and 1.3 g magnesium sulfate heptahydrate diluted to 600 ml with distilled water), 20 ml of stock III (0.735 g calcium chloride dehydrate diluted to 200 ml with distilled water) and 1 ml 0.1% thiamine to 12 g of Bacto agar and adjusting the final volume to 600 ml. For plates containing leucine, 100 µl of a 1.5% solution of leucine was spread on the plates.

TABLE 1

Analysis of Genetic Markers

| Culture Medium | Bacterial Strain | | | |
|---|---|---|---|---|
| | DH10B | SB3499A | SB3499B | SB3499C |
| Minimal | No Growth | No Growth | No Growth | No Growth |
| Minimal + Leucine | Growth | Growth | Growth | Growth |
| MacConkey Galactose | White Colonies | White Colonies | White Colonies | White Colonies |
| LB + Nitrofurantoin 8 µg/ml | No Growth | No Growth | No Growth | No Growth |
| LB + Ampicillin 100 µg/ml | No Growth | No Growth | No Growth | No Growth |
| LB + X gal-IPTG | White Colonies | White Colonies | White Colonies | White Colonies |
| LB + Naladixic Acid | No Growth | No Growth | No Growth | No Growth |
| LB + Kanamycin 50 µg/ml | No Growth | No Growth | No Growth | No Growth |
| LB + Chlorampheni- col 10 µg/ml | No Growth | No Growth | No Growth | No Growth |
| LB + Tetracycline 15 µg/ml | No Growth | No Growth | No Growth | No Growth |

EXAMPLE 5

Genomic DNA Isolation

Genomic DNA isolation is described by Lin and Kuo, *Focus* 17: 66–70 (1995), herein incorporated by reference. *E. coli* strain BRL 3433 (Life Technologies, Inc.) was streaked on LB plates and incubated overnight at 37° C. A single bacterial colony was isolated and resuspended in 5 ml LB broth (10 grams tryptone, 5 grams yeast extract, 5 grams NaCl per liter) and then further incubated at 37° C./275 rpm in a shaking incubator overnight. A 1.0 ml aliquot of the cultured cells was transferred into a microcentrifuge tube and the cell pellets are collected by centrifuging at 11,000×g for 5 minutes at room temperature. The pellets were resuspended in 1 ml TES-sucrose buffer [8% sucrose, 50 mM NaCl, 20 mM Tris-HCl (pH 8.0), and 1 mM EDTA] and incubated at 25° C. for 5 minutes with 1 mg/ml lysozyme. A volume of 100 µl of 10% SDS was added to the tube and the tube was briefly vortexed. The DNA was extracted with phenol-chloroform and precipitated with 0.3M sodium acetate and 1 volume of isopropanol. The solution was centrifuged at 11,000×g for 10 minutes at 4° C. The pellet was washed with 70% ethanol and centrifuged at 11,000×g for 10 minutes at 4° C. To eliminate RNA contamination, the DNA pellet was resuspended with 200 µl TE buffer and then treated with 1 µg/ml RNase A at 37° C. for 10 minutes. The sample was then extracted with phenol-chloroform and the DNA was precipitated with 0.3M sodium acetate and 2.5 volumes of 100% ethanol. The solution was then centrifuged at 11,000×g for 15 minutes at 4° C. The DNA pellet was washed with 70% ethanol and centrifuged at 11,000×g for 10 minutes at room temperature. After washing the DNA pellet, it was dissolved in 100 µl TE buffer.

EXAMPLE 6

Construction of Cosmid Genomic Library of *E. coli* Strain

100 µg DNA of genomic DNA isolated from BRL 3433 (Example 5) was mixed with 10×React 2 (Life Technologies, Inc.) and sterilized distilled water in order to obtain a final concentration of 100 µg/ml DNA in 1×React 2 buffer and in a final reaction volume of 1000 µl. The genomic DNA sample was aliquoted into 9 microtubes with the first tube containing 200 µl of genomic DNA and the other 8 tubes containing 100 µl of the genomic DNA. A 5 µl aliquot was removed from the last tube (tube 9) and was saved as an un-treated control.

10 units of the restriction endonuclease PstI (Life Technologies, Inc.) was added to tube one. A two fold serial dilution was set up as follows: 100 µl of the sample (including enzyme) was transferred from tube one to the second tube, and so on, in order to obtain a series of 2 fold dilutions of PstI concentrations in tubes containing equal concentrations of genomic DNA (10 µg DNA per tube). Finally, 100 µl from the tube 9 was transferred into an additional tube (numbered 10). All 10 tubes were incubated at 37° C. for exactly 1 hour, and immediately stored at −20° C. until use.

All ten tubes were thawed on ice and a 5 µl aliquot from each tube in the serial dilution series was compared to the 5 µl un-cut control by agarose gel electrophoresis (0.9% agarose gel) in order to elucidate the extent to which the genomic DNA was digested. The serial dilution sample or samples, which contained the highest percentage of DNA fragments in the range of 25 to 45 kb estimated by agarose gel electrophoresis according to the method set out in Maniatis et al., *Molecular Cloning, A Laboratory Manual*, Cold Spring Harbor Press, Cold Spring Harbor, N.Y. (1982), was chosen to construct the cosmid library. These chosen aliquot or aliquots were extracted twice with phenol and then ethanol precipitated with 2.5 volumes of 100% ethanol and centrifuged at 11,000 g for 30 minutes. The DNA pellet was washed with 200 µl 70% ethanol and centrifuged at 11,000×g for 10 minutes. The resulting partially digested genomic DNA pellet (termed "genomic digest DNA") was resuspended in 15 µl 1×T4 DNA ligase buffer (Life Technologies, Inc.).

5 µg of BJS80 (pCP13) cosmid vector was incubated for 4 hours at 37° C. with 30 units of PstI (Life Technologies, Inc.) in 1×React 2 (Life Technologies, Inc.) in a final volume of 50 µl. The reaction mix containing the cosmid vector was then ethanol precipitated with 2.5 volumes of 100% ethanol and centrifuged at 11,000×g for 30 minutes. The resulting DNA pellet was washed with 200 µl 70% ethanol and then centrifuged at 11,000×g for 10 minutes. The washed pellet was finally resuspended in 50 µl of 1×React 2 buffer (Life Technologies, Inc.). A 1 µl aliquot of calf intestinal alkaline phosphatase ((1 unit/µl) (Life Technologies, Inc.)) was mixed with the pre-cut cosmid vector and incubated at 37° C. for more than 30 minutes to remove the 5' phosphate. A 5 µl aliquot of the sample was electrophoresed on a 0.9% agarose gel to confirm that the sample was linear according to the method of Maniatis et al., *Molecular Cloning, a Laboratory Manual*, Cold Spring Harbor Press, Cold Spring Harbor, N.Y. (1982). The remainder of the sample was then phenol extracted twice and ethanol precipitated with 2.5 volumes of 100% ethanol and centrifuged at 11,000×g for 30 minutes. The resulting DNA pellet was washed with 200 µl of 70% ethanol and then centrifuged at 11,000×g for 10 minutes. The washed pCP13 cosmid vector was then resuspended in 15 µl 1×T4 DNA ligase buffer (Life Technologies, Inc.) and stored at −20° C. until needed.

The stored cosmid vector was thawed on ice. 15 µl of thawed vector (100 ng/µl) was added to 15 µl of PstI digested "genomic digest DNA" (600 ng/ml) and 1 µl of 1 unit/µl T4 DNA ligase ("ligation reaction mixture") (Life Technologies, Inc.)). The "ligation reaction mixture" was incubated overnight at room temperature and stored at −20° C. until needed.

The ligated DNA was packaged by utilizing the λ packaging kit (the MaxPlax Packaging Extract) from Epicentre Technologies, 1207 Ann Street, Madison, Wis.53713. The packaging procedure was as described in the manufacture's instructions, herein incorporated by reference. The reaction was essentially as follows: from the MaxPlax kit, one tube of freeze thawed sonicate extract, stored at −70° C., was thawed at room temperature. To the thawed extract was immediately added 5 μl of the "ligation reaction mixture" (about 2 μg template DNA). After the sample was centrifuged at 11,000×g for 2 seconds it was incubated at 22° C. for 2 hours. After incubation, 500 μl of phage buffer (10 mM Tris-HCl, 100 mM NaCl, 10 mM $MgCl_2$, and NaOH to pH 8.3) was added to the sample. A 200 μl aliquot was removed from the sample and used to infect DH10B cells ((Life Technologies, Inc.) (Hanahan et al., *Methods in Enzymology*, 204: 63–111 (1991), herein incorporated by reference)) as described below ("retained phage stock"). The remainder of the sample was mixed with 15 μl chloroform and stored at 4° C. as a phage stock for future use.

From an overnight culture, a 200 μl aliquot of a culture of DH10B was used to inoculate 25 ml of LB medium. The cells were grown at 37° C. shaking at 275 rpm. When the cell density reached O.D.$_{590}$ 0.5, the cells were centrifuged at 11,000 g for 2 minutes and then resuspended in 2 ml of 10 mM $MgSO_4$. 200 μl of the "retained phage stock" was mixed with a 150 μl aliquot of DH10B cells. The mixture was incubated at 37° C. for 15 minutes. After the incubation, 700 μl of SOC medium (Life Technologies, Inc.) was added to the sample and the sample was then incubated at 37° C. for an additional hour. 100 μl aliquots of the sample was spread on freshly prepared LB+Tet15 agar plates (LB agar plates containing 15 μg/ml tetracycline). The bacteria were grown overnight at 37° C.

Ten separate colonies were selected. Each colony was placed in a separate tube containing 3 ml of LB medium. These tubes were placed at 37° C. overnight. Cosmid DNA was isolated by the mini-prep method as described in Maniatis et al., *Molecular Cloning, A Laboratory Manual*, Cold Spring Harbor Press, Cold Spring Harbor, N.Y. (1982). Confirmation of the cosmid DNA was carried out by digesting the cosmid DNA with PstI according to manufacturers instructions. The average size of the genomic inserts was 20 kb or larger.

The remaining bacteria from the 10 plates were pooled and suspended in 20 ml CG medium (CIRCLE GROW, Bio101, Inc., Cat # cp-1000C). After pooling of the bacteria, glycerol was mixed with the suspended bacteria to a final glycerol concentration of 10% glycerol (v/v). The mixture was divided into 5 ml aliquots and stored at −70° C. as the cosmid library glycerol stock for future use.

The number of clones in a cosmid library was calculated by removing one of glycerol stocks and then thawing the stock on ice. The number of bacterial cells was determined by removing a 100 μl aliquot from the thawed stock and diluting that aliquot based on the expected number of bacterial cells ($10^{11}$ cells/ml). Based on the expected number of cells, 100 μl of the sample diluted $10^4$, $10^3$, and $10^2$ fold were plated on three LB+Tet15 agar plates (LB agar plates containing 15 μg/ml tetracycline) and grown at 37° C. overnight. From the plated samples, it was possible to calculate that the cosmid library was $10^{11}$ cells/ml in its glycerol stock.

EXAMPLE 7

Selection of Stability Cosmid Clones

A 20 μl aliquot of the BRL 3433 cosmid library (initial viable cell count $1.0 \times 10^5$ cells/ml) was used to inoculate 5 ml of 15/10 medium (1.0% (w/v) Bacto Tryptone, 1.5% (w/v) Bacto Yeast Extract, 10 mM NaCl, 2.5 mM KCl, 10 mM $MgCl_2$, 10 mM $MgSO_4$, 0.001% polyethelene glycol) and 100 μg/ml kanamycin. The bacteria were incubated at 30° C. for 18 hours. The bacteria were harvested by centrifuging the bacteria at 3,000 rpm for 10 minutes at 4° C. The bacteria were then resuspended in 0.5 ml cold CCMB80 buffer (80 mM $CaCl_2$, 20 mM $MnCl_2$, 10 mM $MgCl_2$, 10 mM potassium acetate, and 10% (v/v) re-distilled glycerol), stored on ice for 20 minutes and then frozen in a dry ice ethanol bath. The cells were then thawed prior to storage at 4° C. The viable cell count of the bacterial cells was determined by diluting the cells in 0.85% NaCl and plating those dilutions on LB plates. The plates were then incubated at 37° C. overnight and the colony count was determined.

After storing aliquots of the cells for 36 days at 4° C., the viable cell count of stored cosmid library clones was determined. Viability declines from an initial value of $2.5 \times 10^8$ cells/ml to $1.6 \times 10^5$ cells/ml. Individual colonies that survived 36 days at 4° C. were isolated by diluting the stored cosmid clones. The diluted cosmid clones were plated on LB plates and then incubated overnight at 37° C. Individual colonies were randomly selected. Cosmid DNA was purified from the isolated colonies. The cosmid DNA was analyzed by digesting with PstI, according to the manufacturer's instructions (Life Technologies, Inc.) and three isolates were retained for additional analysis and labeled cosmid clones 1 (NRRL B-21550, deposited Mar. 28, 1996, Agricultural Research Service Culture Collection (NRRL), 1815 North University Street, Peoria, Ill. 61604, USA), 2 (NRRL B-21551, deposited Mar. 28, 1996, Agricultural Research Service Culture Collection (NRRL), 1815 North University Street, Peoria, Ill. 61604, USA), and 4 (NRRL B-21552, deposited Mar. 28, 1996, Agricultural Research Service Culture Collection (NRRL), 1815 North University Street, Peoria, Ill. 61604, USA).

EXAMPLE 8

Characterization of Cosmids Clones 1, 2 and 4

DH10B bacteria containing either cosmid clone 1, 2, 4 or cosmid vector pCP13 were incubated in 2 mls of 15/10 medium for 16 hours at a temperature of 30° C. From these cultures, a 0.3 ml aliquot was used to inoculate 50 ml of 15/10 medium and kanamycin at 10 μg/ml in 500 ml baffled shake flasks. The flasks were incubated at 30° C. in a shaking incubator at 275 rpm until the optical densities of the cultures were between 0.335 and 0.399 (O.D.$_{550}$). The bacterial cultures were harvested by centrifugation. The resultant pellets were resuspended in 4 ml of cold CCMB80 buffer and kept on ice for 20 min. 250 ml aliquots of the resuspended samples were placed in 1.0 ml Nunc cryovials and those tubes were then frozen in a dry ice/ethanol bath. Aliquots of these cells were assayed for transformation efficiency according to the method of Hanahan (*J. Mol. Biol.* 166: 557–580 (1983) and viable cell counts were made. The vials were then placed at −20° C. for the stability study. The remaining aliquots were thawed and retained at 4° C. for additional analysis.

Figure 3:
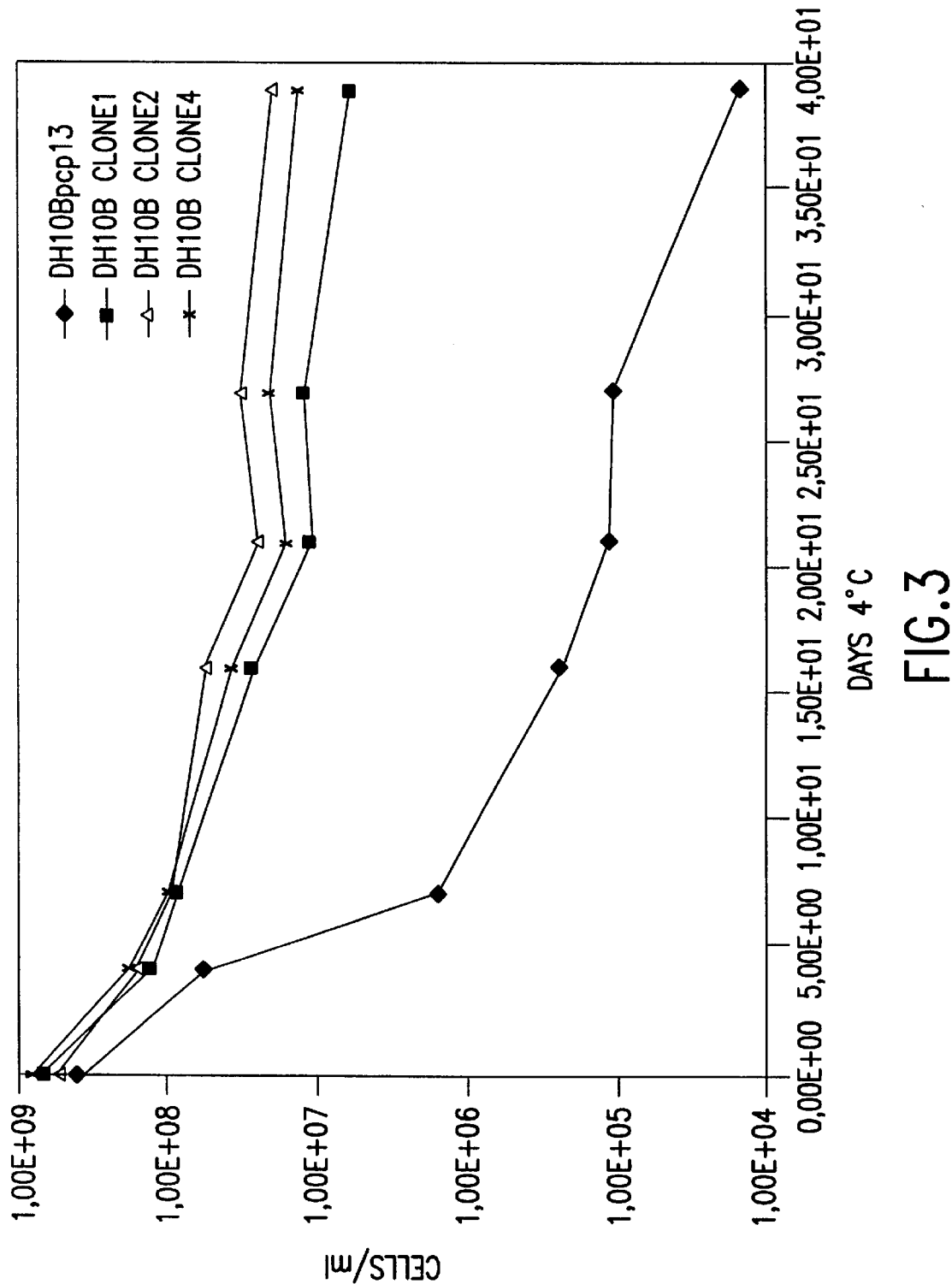
FIG. 3 shows the viable cell counts of DH10B bacteria containing either the cosmid vector pCP13, or cosmid 1 (NRRL B-21550), 2 (NRRL B-21551) or 4 (NRRL B-21552) after those cells are stored at 4° C. for periods of time.

FIG. 3 shows that the viable cell count of DH10B containing the vector pCP13 decreased over time at 4° C.

from approximately $5.0 \times 10^8$ cells/ml to approximately $1.0 \times 10^5$ cells/ml over a period of 40 days. In contrast, DH10B containing cosmid clones 1, 2 or 4 were more stable and only showed a decrease of approximately 50 fold in the viable cell count over the same period of time.

FIG. 4 shows that the viable cell counts of DH10B cells containing vector pCP13 decreased 1000 fold over a period of 4 months when the cells are stored at −20° C. In contrast, DH10B cells containing cosmid clone 1 show a decreased viability of 50 fold over the same period. FIG. 4 also demonstrated that DH10B cells containing cosmid clones 2 or 4 showed a 10 fold improvement in survival compared to DH10B pCP13 cells and that cosmid clone 1 improved the viable cell count 100 fold.

EXAMPLE 9

Loss of Cosmid 1 Results in a Loss of Low Temperature Stability and Retransformation of DH10B with Clone 1 Restores Low Temperature Stability The cosmid clones were cured from the DH10B cells using coumermycin, as described by Danilevskaya and Gragerov, *Mol. Gen. Genet.* 178: 233–235 (1980), herein incorporated by reference. A 20 μl aliquot of DH10B cosmid clone 1, DH10B cosmid clone 2 and DH10B cosmid clone 4 cells stored at 4° C. was inoculated into 1 ml SOB—Mg medium (Life Technologies, Inc.). The cells were grown at 37° C. for 16 hours. The cells were diluted to approximately $1.0 \times 10^4$ cells/ml in SOB—Mg medium. One ml aliquots of the cells were cultured in the presence of 0, 1, 2, 3, and 4 μg/ml coumermycin for 16 hours at 37° C. The cultures which were grown in the presence of 4 μg/ml coumermycin were then streaked on LB plates and the colonies were screened for the ability to grow in the presence and absence of kanamycin. Cells which showed no growth in the presence of kanamycin have lost cosmid clone 1.

One kanamycin sensitive colony from each culture was then grown in 5 ml of 15/10 medium at 30° C. for 4 hours. The bacterial cells were centrifuged at 3,000 rpm for 10 minutes and resuspended in 0.4 ml of cold CCMB80 buffer. The cells were kept on ice for 20 minutes and then frozen in a dry ice ethanol bath. After freezing, the cells were thawed and placed at 4° C. Viable cell counts were taken at day 0, day 5 and day 11.

Figure 4B:
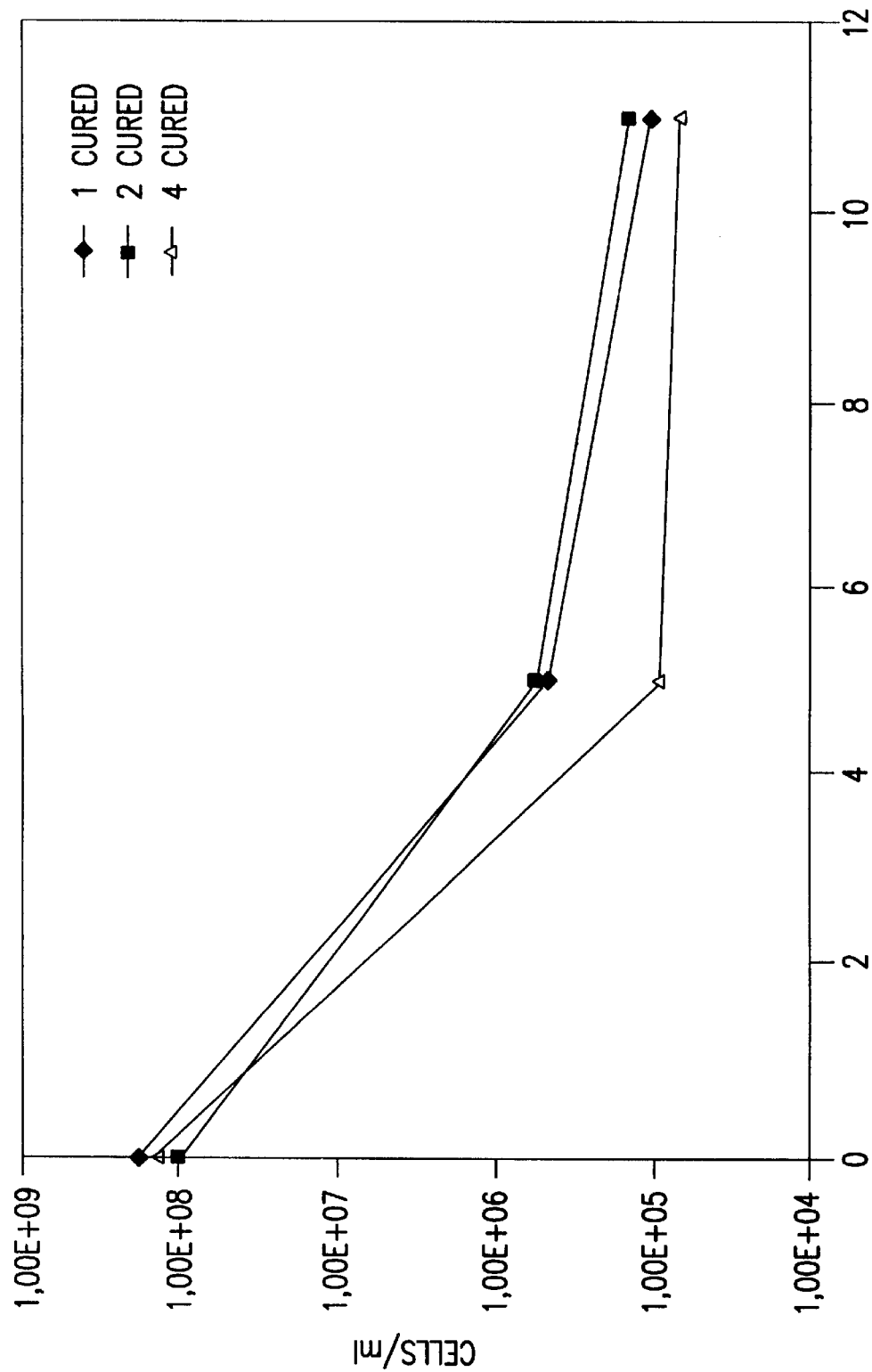
FIG. 4B shows the viable cell counts of DH10B cells cured of clones 1, 2, and 4 after these cells are stored at 4° C. for periods of time.

FIG. 4B shows that the viable cell count of cells cured with respect to cosmid clone 1, clone 2 or clone 4 decreased as rapidly as DH10B cells or DH10B cells containing pCP13 and failed to display the stability at 4° C. seen in the cultures containing cosmid clones 1, 2, or 4. Curing cosmid clone 1 from the DH10B cells resulted in the rapid loss of viability when the cells were placed in CCMB80 buffer at 4° C.

To assess whether the reintroduction of cosmid clone 1 into the cured DH10B cells would restore stability, competent cells of DH10B which had been cured of cosmid clone 1 were prepared.

Cosmid clone 1 as well as cosmid pCP13 were then retransformed into competent cells of the DH10B strain which had been cured of cosmid clone 1 using the method of Hanahan (*J. Mol. Biol.* 166: 557–580 (1983)). Max efficiency DH10B competent cells lot FA4104 (Life Technologies, Inc.) were also transformed with cosmid clone 1 and pCP13. The transformed cultures were plated on LB plates containing 50 μg/ml kanamycin and incubated at 30° C. Competent cells of DH10B containing pCP13 and DH10B containing cosmid clone 1 as well as competent cells of DH10B were prepared as follows: DH10B containing vector pCP13 and DH10B containing cosmid clone 1 were grown in 50 ml of 15/10 medium containing 50 μg/ml kanamycin until the cells were at an $O.D._{550}$ of between 0.244 and 0.258. DH10B cells were grown in 15/10 medium without kanamycin. The cells were harvested by centrifugation and were then resuspended in 4 ml cold CCMB80 buffer. After resuspension, the cells were kept on ice for 20 min. The cells were then frozen in a dry ice ethanol bath, thawed and placed at 4° C.

Figure 5:
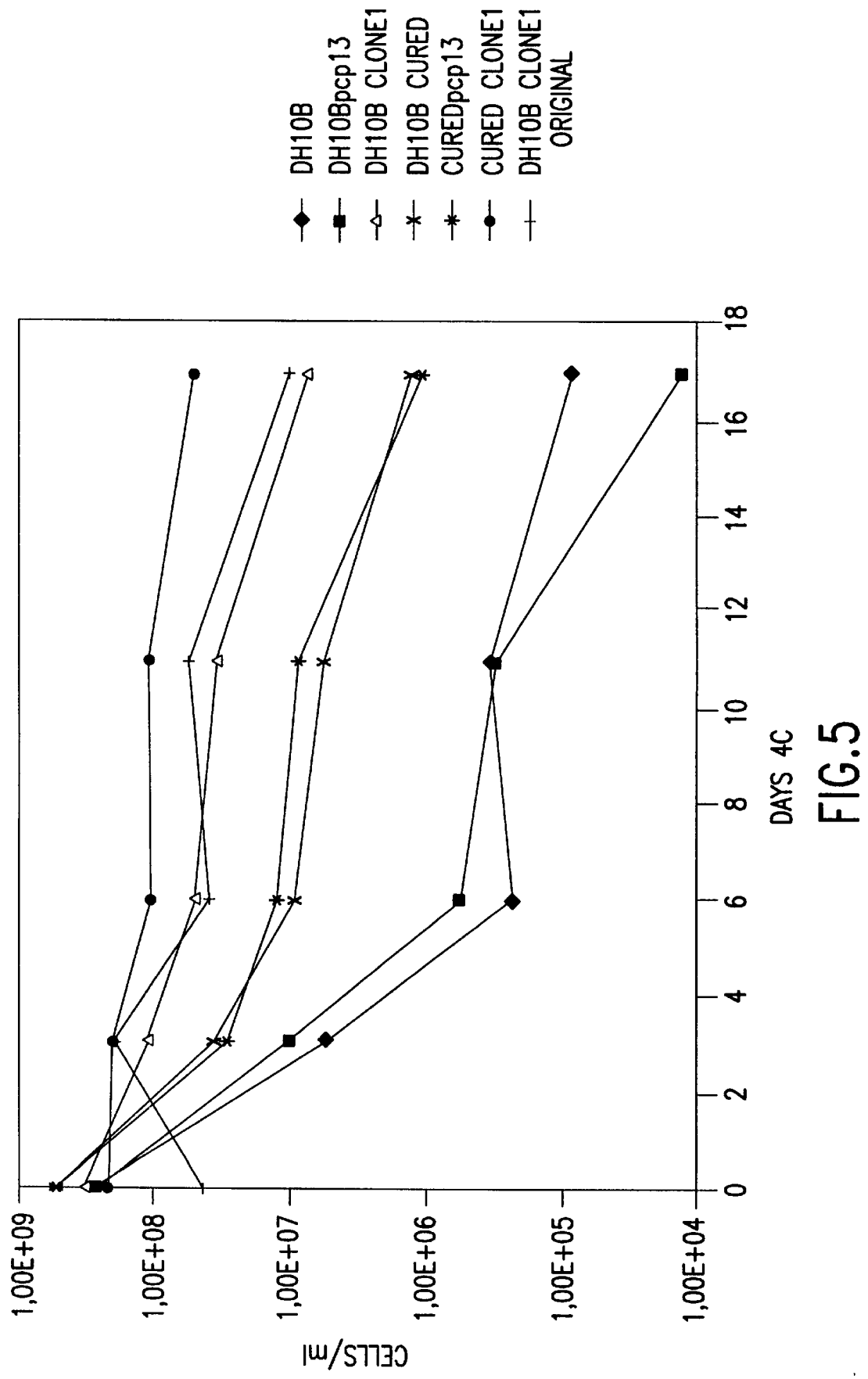
FIG. 5 shows the viable cell counts of DH10B cells, DH10B cells containing vector pCP13 or cosmid 1, DH10B cured of cosmid 1, DH10B cured of cosmid 1 and retransformed with vector pCP13, or cosmid 1 and DH10B cells containing cosmid 1 after those cells are stored at 4° C. for periods of time.
Figure 6A:
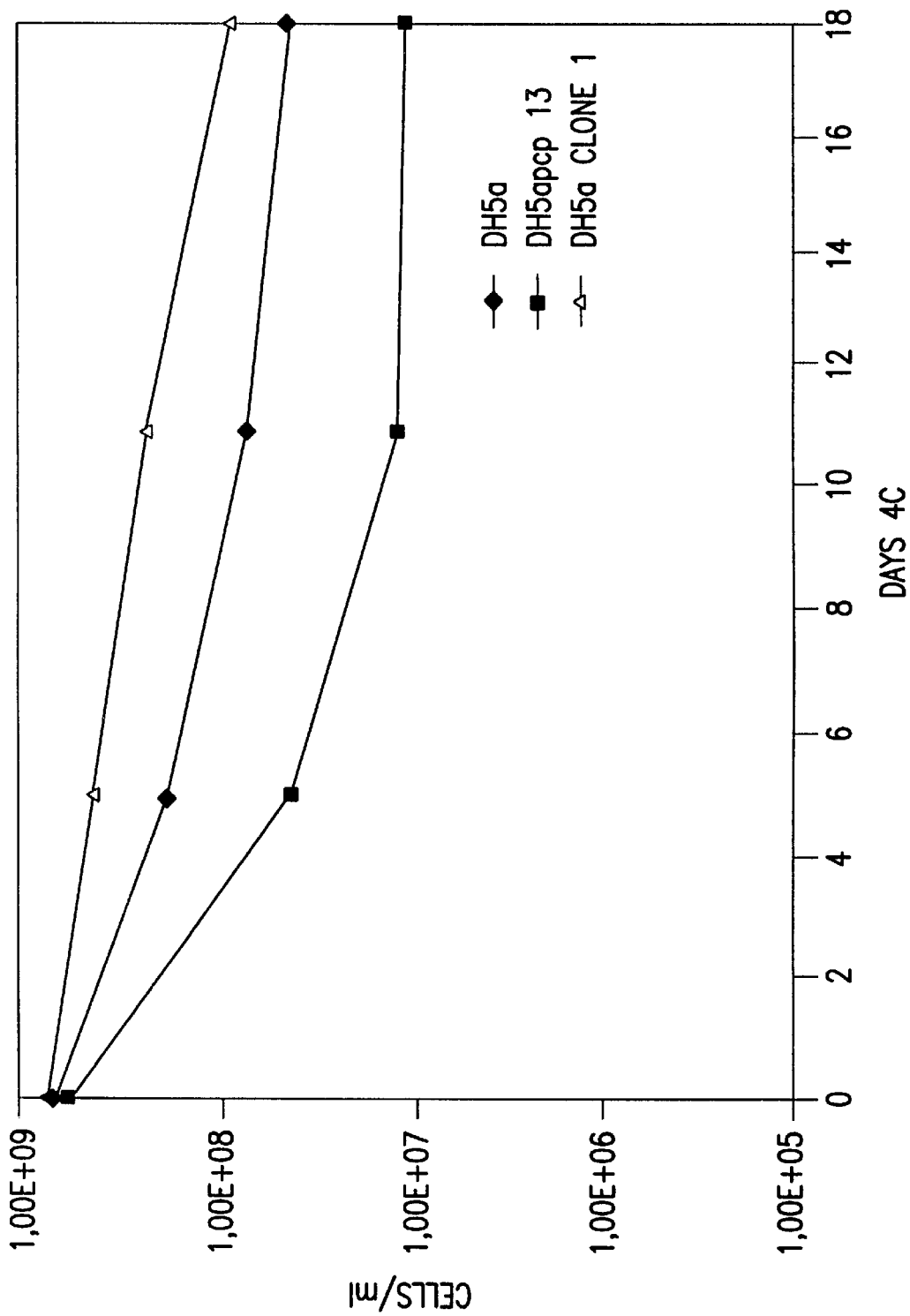
FIGS. 6A and 6B show the viability of the following bacterial strains stored at 4° C.: DH5α, DH5α containing the vector pCP13, DH5α containing cosmid 1, STBL2, STBL2 containing the vector pCP13, and STBL2 containing cosmid 1 after those cells are stored at −20° C. for periods of time.
Figure 6B:
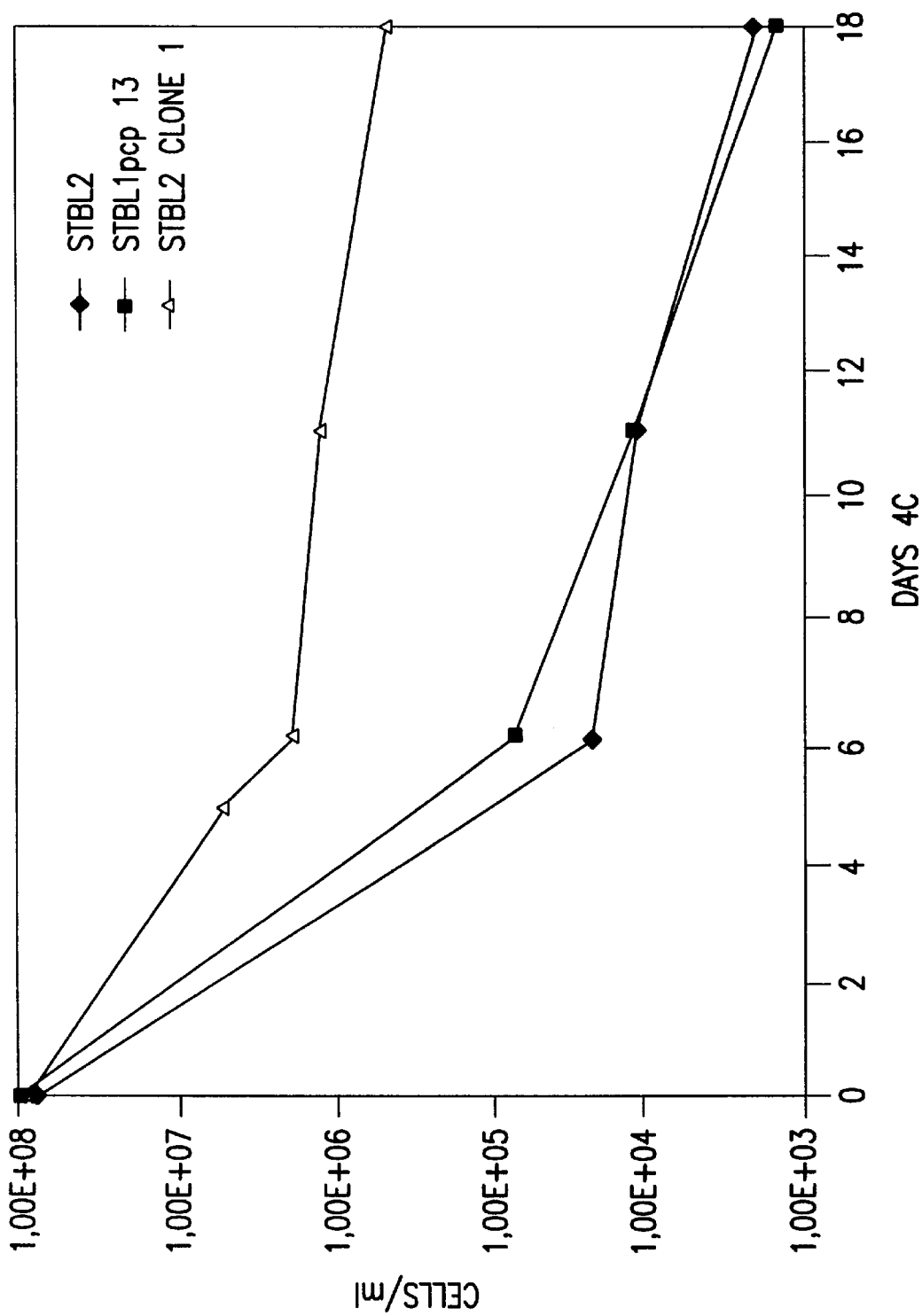

Viable cell counts were determined at intervals for the cells stored in CCMB80 buffer at 4° C. FIG. 5 shows that the viable cell count of DH10B cells or DH10B containing the vector pCP13 cells decreased rapidly from approximately $1.0 \times 10^8$ cells/ml to approximately $1.0 \times 10^5$ to $1.0 \times 10^6$ cells/ml over a period of approximately 16 days. On the other hand the presence of cosmid clone 1 resulted in a 100 fold increase in the number of viable cells/ml. These results also indicate that the reintroduction of cosmid clone 1 into DH10B cells cured of cosmid clone 1 (which are unstable at 4° C.) again improves stability of these cells at 4° C. FIGS. 6A and 6B show that the introduction of cosmid containing stability genes for storage in low temperature into DH5α and STBL2 (Trinh et al., *Focus* 16: 78–80 (1994) cells enhanced viability of those cell lines at 4° C.

EXAMPLE 10

Increases in Transformation Efficiency Due to Presence of Clone 1

FIG. 7 shows that DH10B strain containing cosmid clone 1 stored at −20° C. for three months exhibits an enhanced transformation efficiency (greater than 100 fold) compared with DH10B containing the vector pCP13 similarly stored. After 3 months at −20° C., DH10B containing the vector pCP13 cells exhibited a transformation efficiency of less than $1.0 \times 10^5$ Transformants/μg. In contrast, DH10B cells containing cosmid clone 1 exhibited a transformation efficiency of $>1.0 \times 10^6$ Transformants /μg.

EXAMPLE 11

Isolation of DNA Fragments of Clone 1 Reponsible for Increased Viability and Transformation Efficiency Cosmid Clone 1 contains a 22 Kb insert which was shown to substantially improve low temperature stability in several strains of *E. coli*. The 22 Kb insert in cosmid clone 1 was digested using the restriction endonuclease PstI and 2 fragments of 14 Kb and 8 Kb were isolated. These two fragments were subsequently cloned into the plasmid vector pDELTA2 (the plasmid vector utilized in the generation of nested deletions described below) at its PstI site. The restriction maps of both subclones were deduced by digesting the plasmid DNA with either HindIII or EcoRI. These two subclones were designated pDELTA2 14Kb and pDELTA2 8Kb respectively, based on their size. To distinguish the orientation of pDELTA2 14Kb and pDELTA 8 Kb, the plasmids having the opposite orientations were designated pDELTA2 14Kb+ and pDELTA1 14Kb− and pDELTA2 8Kb+ and pDELTA2 8Kb−.

EXAMPLE 12

Subcloning 14 and 8 Kb Fragments of Clone 1 into pDELTA2

Figure 8:
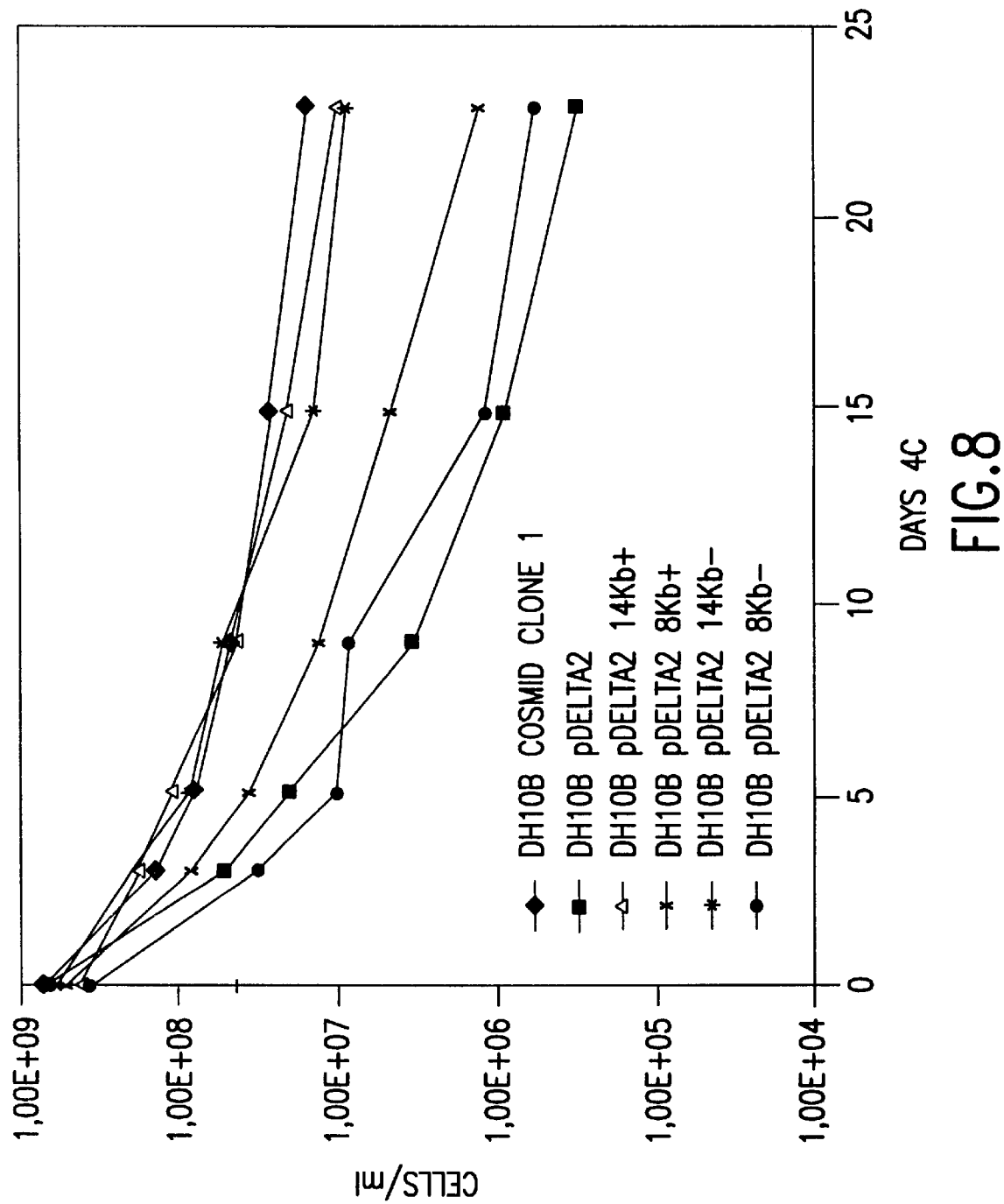
FIG. 8 shows the viability of DH10B cells containing either cosmid clone 1, pDELTA2, pDELTA2 8Kb+, pDELTA2 8Kb−, pDELTA2 14Kb+, or pDELTA2 14Kb− plasmid after storage at 4° C.
Figure 9:
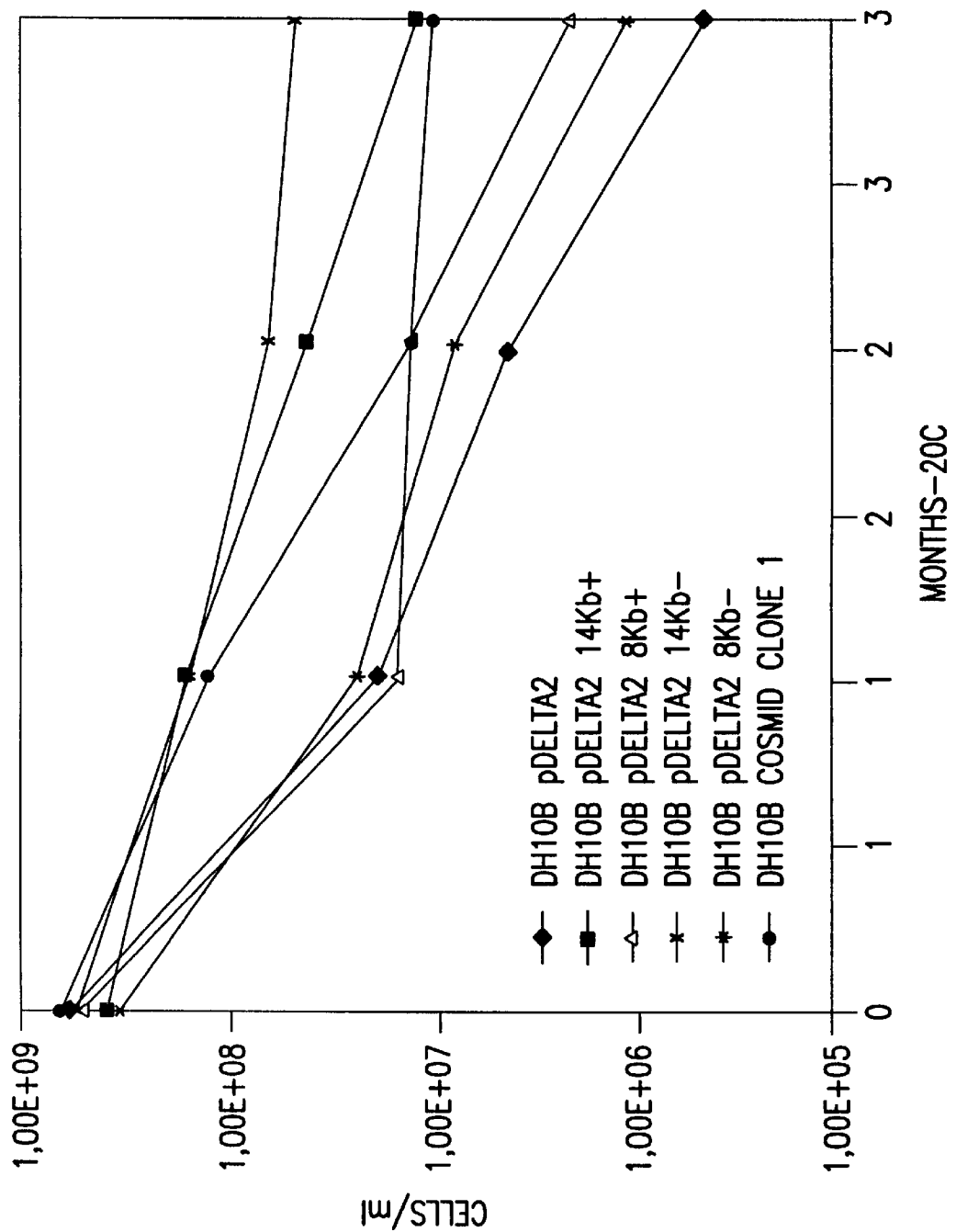
FIG. 9 shows the viability of DH10B cells containing either cosmid clone 1, pDELTA2, pDELTA2 8Kb+, pDELTA2 8Kb−, pDELTA2 14Kb+, or pDELTA2 14Kb− plasmid after storage at −20° C.

To determine which of the subclones is able to stabilize DH10B cells stored at 4° C. or −20° C., the pDELTA2 plasmid containing the 14 Kb subclone in either orientation (pDELTA2 14 Kb+ and pDELTA2 14 Kb-) and the pDELTA2 plasmid containing the 8 Kb subclone in either orientation (pDELTA2 8 Kb+ and pDELTA2 8Kb-) were transformed into competent cells of *E. coli* strain DH10B. Transformants were selected on LB plates containing 50 µg/ml kanamycin at 30° C. Single colonies of DH10B cosmid clone 1, DH10B pDELTA2, DH10B pDELTA2 8Kb+, DH10B pDELTA2 8Kb-, DH10B pDELTA2 14 Kb+, and DH10B pDELTA2 14Kb- were picked from the LB kanamycin plate into 2 ml of 15/10 medium containing 50 µg/ml kanamycin and the cultures were incubated with shaking at 30° C. for 16 hours. 0.3 ml of the overnight cultures were inoculated into 60 ml of the same medium and the cultures were incubated at 30° C. 275 rpm. The optical density was monitored and at an OD 550 nm of approximately 0.3 (0.26 to 0.307), 50 ml of the cell culture was collected by centrifugation for 10 min at 4° C. in an IEC clinical centrifuge. The cell pellets were resuspended in 4 ml of cold CCMB80 buffer and the cells were allowed to remain on ice for 20 min. 250 µl aliquots were vialed in chilled NUNC cryovials and the vials were frozen in a dry ice ethanol bath. The vials were stored at -70° C. until assay and then the vials were shifted to a -20° C. freezer for the stability study. The remainder of the cells (approximately 2 ml) in CCMB80 buffer were frozen in a dry ice ethanol bath, thawed on ice for 10 min and assayed for the viable cell count. The remainder of the cells were then stored at 4° C. for the stability study. At intervals vials were removed from the -20° C. freezer for determination of the viable cell count. In addition, the cells stored at 4° C. were also assayed for viable cell count. The results are presented in FIGS. 8 and 9. The data presented in FIG. 8 indicate that the 14 Kb subclone in either orientation (plasmids pDELTA2 14Kb+ and pDELTA2 14Kb-) substantially improves the stability of the DH10B strain when stored at 4° C. On the other hand the 8 Kb subclone does not improve the stability of the cells. In addition, the 14 Kb subclone in either orientation also improves the stability of the cells stored at -20° C. (FIG. 9). This finding demonstrates that the stability gene found in cosmid clone 1 resides on the 14 Kb subclone.

EXAMPLE 13

Generation of Deletion Factory Derivatives to Localize the DNA Fragments Responsible for Stability To narrow the region in plasmid pDELTA2 14Kb+ which results in greater stability of DH10B cells stored at 4C, the Life Technologies Inc. (Rockville MD) Deletion Factory™ System was utilized. This system generates a series of nested deletions of varying length in the 14 Kb insert in plasmid pDELTA1 14Kb+. The Deletion Factory System was used following the recommendations of the manufacture.

The clones were selected based on their resistance to ampicillin and sucrose or their resistance to kanamycin and streptomycin. thirty-six different clones were selected from each selection and the plasmid DNA was isolated based on the same procedure as for cosmid clone1. The plasmid DNA from all 72 different clones for both selections were digested by PstI. This digestion linearized the plasmid DNA without cutting out the insert from the vector because one of the PstI cloning sites was lost during the generation of the deletion clones. The linearized plasmid DNA was separated on a 1% agarose gel with the 1 kb ladder (Gibco/BRL) as a standard. The size of each clone was calculated based on the 1 kb ladder following Sambrook et al. 1989. A representative sample of the clones, based on the size of the insert DNA, were selected for further analysis of their ability to stabilize DH10B cells stored at 4C.

Eleven deletion derivatives of plasmid pDELTA2 14Kb+ in strain DH10B which had been generated on agar plates containing 5% sucrose and 100 µg/ml ampicillin were picked into 2 ml of 15/10 medium containing 100 µg/ml ampicillin and the cultures were grown for 16 hours at 30° C. DH10B containing plasmid pDELTA2, DH10B containing plasmid pDELTA 14Kb+ and DH10B containing plasmid pDELTA2 14Kb- were also grown in the same medium. 25 µl of the overnight cultures were inoculated into 5 ml of the same medium in a 50 ml Falcon tube and the tubes were shaken at 30° C. 275 rpm for 3 hours. The cells were collected by centrifugation for 10 min 4° C. 2500 rpm in an IEC HN SII centrifuge. The cell pellets were resuspended in 400 µl of cold CCMB80 buffer. The cells were allowed to remain on ice for 20 min. The cells were frozen in a dry ice ethanol bath for 5 minutes and thawed on ice for 15 minutes. The viable cell count was determined by dilution in 0.85% saline. The cells were placed at 4° C. for the stability study. At intervals, the viable cell count was determined and the results are presented in FIG. 10. The data indicate that the plasmids assort into 2 distinct classes: those which stabilize the DH10B cells and those which do not. Among the plasmids which stabilize DH10B cells are plasmids 16, 18, 27 and 32. Among the plasmids which do not stabilize the DH10B cells are plasmids 14, 19, 23, 28, 29, 33 and 34. As controls the plasmid pDELTA2 does not stabilize the DH10B cells whereas plasmids pDELTA2 14Kb+ and plasmids pDELTA2 14Kb- stabilize the DH10B cells. In particular, note plasmid 32 (hereafter referred to as pDELTA2 32). This plasmid is the smallest plasmid derived from pDELTA2 14Kb+ (using the Deletion Factory System) which is capable of stabilizing DH10B cells at 4° C.

To assess which of the plasmids still contained the gene or genes which improves stability of DH10B cells stored at 4° C., 16 deletion derivatives of pDELTA2 14 Kb+ in strain DH10B which had been isolated on agar plates containing 100 µg/ml streptomycin and 50 µg/ml kanamycin were picked into 2 ml 15/10 medium containing 50 µg/ml kanamycin and were grown overnight at 30° C. 25 ul of the overnight cultures were inoculated into 5 ml of the same medium in 50 ml Corning tubes (Fisher cat # 05-539-6) and the tubes were shaken at 30° C. 275 rpm for 3 hours. The cells were collected by centrifugation for 10 min 4° C. 2500 rpm using an IEC HN SII centrifuge and the cell pellets were resuspended in 400 ul of cold CCMB80 buffer. The cells were allowed to remain on ice for 20 min. The cells were frozen in a dry ice ethanol bath for 5 min, thawed on ice, and the viable cell count was determined. The tubes were placed at 4° C. for the stability study. At intervals the viable cell counts were determined and the results are presented in FIG. 11. The data again indicate that the plasmids assort into 2 distinct classes: those plasmids which improve the stability of the DH10B cells and those plasmids which do not. Among the plasmids which stabilize the DH10B cells are plasmids 3, 10, 12, 16, 20, 23, and 31. Among the plasmids which do not stabilize the DH10B cells are plasmids 1, 2, 4, 8, 9, 21, 32, 35, and 36. As above, plasmid pDELTA2 does not stabilize the DH10B cells stored at 4° C. whereas plasmid pDELTA2 14Kb+ does stabilize the cells. In particular note plasmid 16 (hereafter referred to as pDELTA2 16). This plasmid is the smallest plasmid from this screen which is capable of stabilizing DH10B cells at 4° C.

Figure 10:
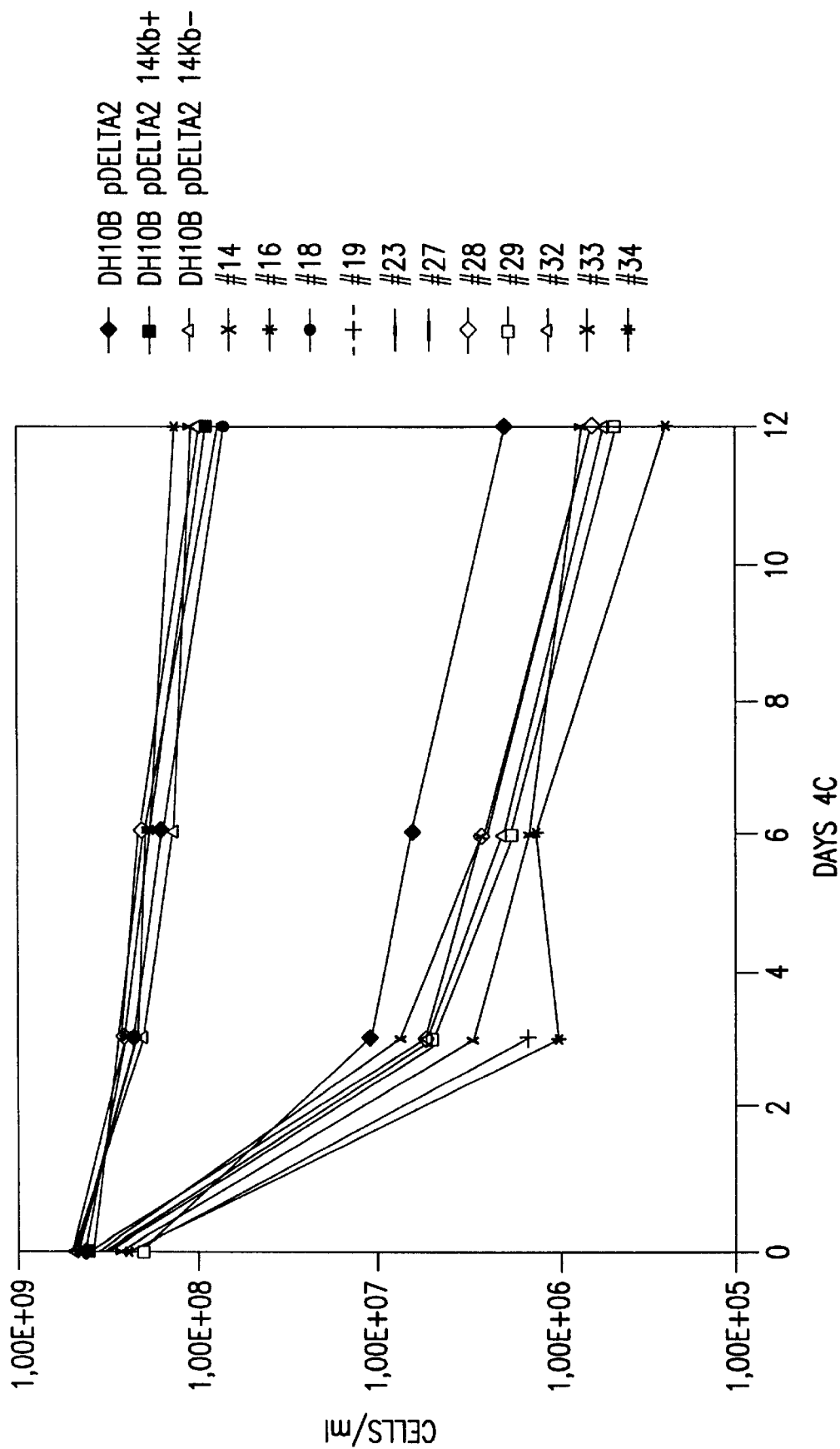
FIG. 10 shows the viability of DH10B cells containing either the pDELTA2, pDELTA2 14Kb+, pDELTA2 14Kb− plasmid, or one of eleven deletion derivatives of the pDELTA2 14Kb+plasmid generated by the Deleletion Factory System under sucrose/ampicillin selection after storage at 4° C. for various intervals.
Figure 11:
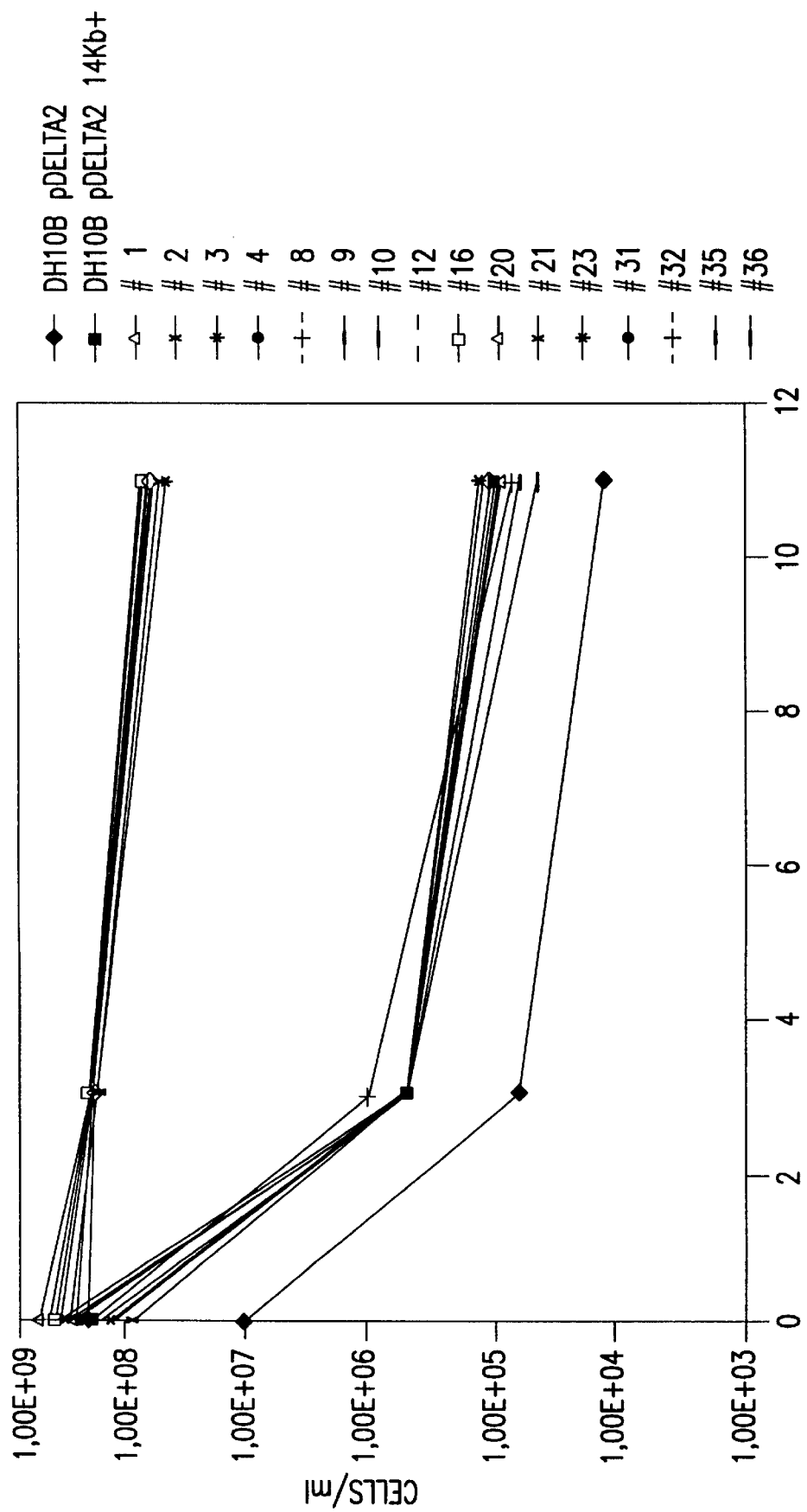
FIG. 11 shows the viability of DH10B cells containing either the pDELTA2, pDELTA2 14Kb+, plasmid, or one of sixteen deletion derivatives of the pDELTA2 14Kb+ generated by the Deleletion Factory System under streptomycin/kanamycin selection after storage at 4° C. for various intervals.
Figure 12:
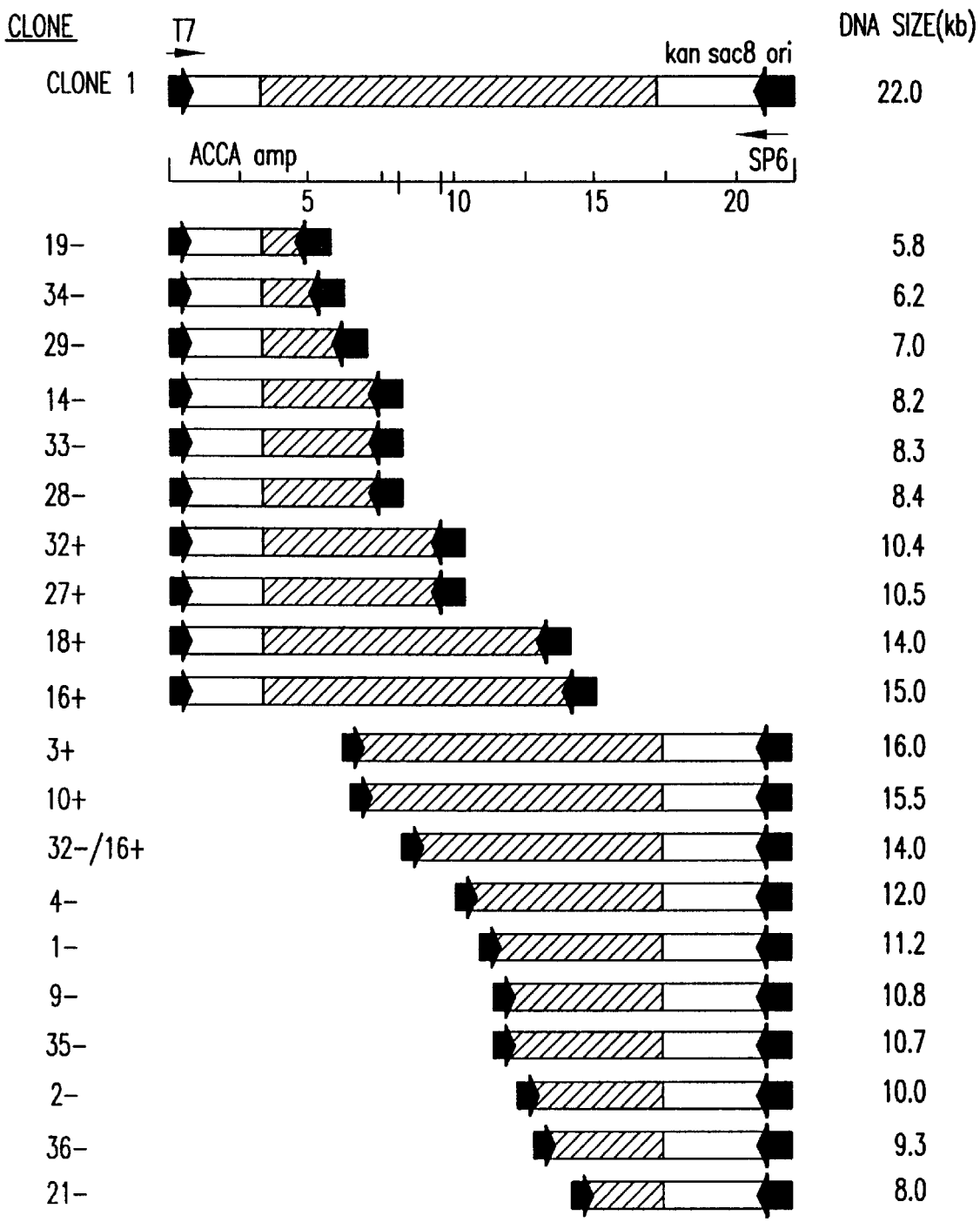
FIG. 12 combines the stability studies outlined in FIGS. 10 and 11 and presents the length of the insert DNA remaining after deletion of a portion of the insert using the Deletion Factory System.

FIG. 12 combines the stability studies outlined in FIGS. 10 and 11 and presents the length of the insert DNA remaining after deletion of a portion of the insert using the Deletion Factory System. FIG. 12 illustrates that use of the Deletion Factory System narrows the region containing the stability gene to an insert size of approximately 2.5 KB.

EXAMPLE 14

Localization and Sequence of Stability/ Transformation Gene on Cosmid Clone 1

Deletion clones 16 and 32 delimited a region of essential sequence approximately 2500 bases long. Primers complementary to the vector and adjacent to the deletion ends of these clones were used to sequence into the essential region. For clone 16 primer T7-25 (CGA CTC ACT ATA GGG AAC TGA TCC T)(SEQ ID NO.: 1) was used and for clone 32 primer SP6-25 (GAT TTA GGT GAC ACT ATA GAG ATC C) (SEQ ID NO.: 2) was used.

DNA sequencing was performed using the method of cycle sequencing with [α-$^{35}$S]dATP (Murray, V. (1989) *Nucleic Acids Res.* 17, 8889, herein incorporated by reference). The sequence obtained from clone 16 was 302 bases long and the sequence obtained from clone 32 was 169 bases long. A BLAST Search was performed using BLASTN with each piece of sequence. A strong match (P(N)=2.8×10$^{-40}$) was found between clone 16 sequence and the region of DNA 141 bases downstream of the *E.coli* gene fabB which encodes for beta-ketoacyl-ACP synthase I (accession number M24427). Clone 32 gave a weak match (P(N)=0.47) with a region of *Haemophilus influenzae* DNA 936 bases upstream of the fabB gene (accession number U32775 L42023). This region in *E. coli* was not yet in the database. From the known *E.coli* DNA sequence in the fabB region, sequencing primers were designed along each strand at roughly 300 base intervals. Dye terminator sequencing was performed using an ABI 373A Stretch Sequencer. Additional primers were designed to extend the sequence from clones 16 and 32 until all sequence data were able to be assembled into one contiguous piece. The additional sequence primers included: "from 32" CCA CAT ATC CGG GTT TTT CGC TG (SEQ ID NO: 3); "fab46" GAG GTT GGC AGG TTG TAT GGA GT (SEQ ID NO: 4); "fab470" TAT GGA GCA GGC AAT CGC TGA TG (SEQ ID NO: 5); "fab1176" CGT GAA GTG TTC GGC GAT AAG AG (SEQ ID NO: 6); "fab1510" AAT GCG GCC TCC GGC ACT AAC AC (SEQ ID NO: 7); "from 16" GGT TAC GGT GCG TTG GCA GGA TT (SEQ ID NO: 8); "fab1104° C." TAT CAA CGC CAT GCA TCG CCA TC (SEQ ID NO: 9); "fab68C" ACT CCA TAC AAC CTG CCA ACC TC (SEQ ID NO: 10); "fab796" CTG GCG GCG GCG AAG AG (SEQ ID NO: 11); "fab150" AAA TGG CTG ATC GGA CTT GTT (SEQ ID NO: 12); "fab865C" TCC GGG GTG TCG TTG TATT (SEQ ID NO: 13). Sequencher 2.0 (Gene Codes Corp.) was used to assemble the data. The sequence of the significant region of clone 1 (SEQ ID NO: 14) is shown in FIG. 13.

The fabB region of *E.coli* strain DH10B was amplified using 1.1×Elongase Supermix (LTI) and primers at positions 39 (TAAATTCGAGGTTGGCAGGTT) (SEQ ID NO: 15) and 1592 (AATCGACAAAGCGGGAAGTT) (SEQ ID NO: 16) in the M24427 sequence. The cycling conditions were 30 cycles of (95° C. for 30 seconds, 55° C. for 75 seconds and 72° C. for 2 minutes) followed by a single incubation at 72° C. for 10 minutes. The PCR product was purified by digesting with Exonuclease I (Adamczky, J. J., Jr. (1995) *Editorial Comments* 22, 36, herein incorporated by reference.) and precipitating with isopropanol (Brow, M. A. D. (1990) in *PCR Protocols: A Guide to Methods and Applications* (Innis, M. A., Gelfand, D. H., Sninsky, J. J., and White, T. J., eds.) p. 194, Academic Press, San Diego. The pellet was redissolved in the initial volume of 10 mM Tris-HCl (pH 7.5), 5 mM NaCl, 0.1 mM EDTA. Again dye terminator sequencing was performed using an ABI 373A Stretch Sequencer and primers from the list above. The sequence alignment program Align Plus (Scientific and Educational Software) was used to compare the sequences derived from clone 16 and DH10B to show that they were identical over the region sequenced.

In the sequence from FIG. 13, the essential region of clone 1 contained several open reading frames in addition to fabB. Deletions were made to confirm that the function was correlated specifically with the fabB gene (see below). Open reading frames greater than 100 amino acids in the essential region of clone 1 are as follows:

| ORF | Bases | Number of Amino Acids |
| --- | --- | --- |
| 1 (fabB) | 1043–2263 | 406 |
| 2 | 1900–1133 | 255 |
| 3 | 488–24 | 154 |

Figure 14:
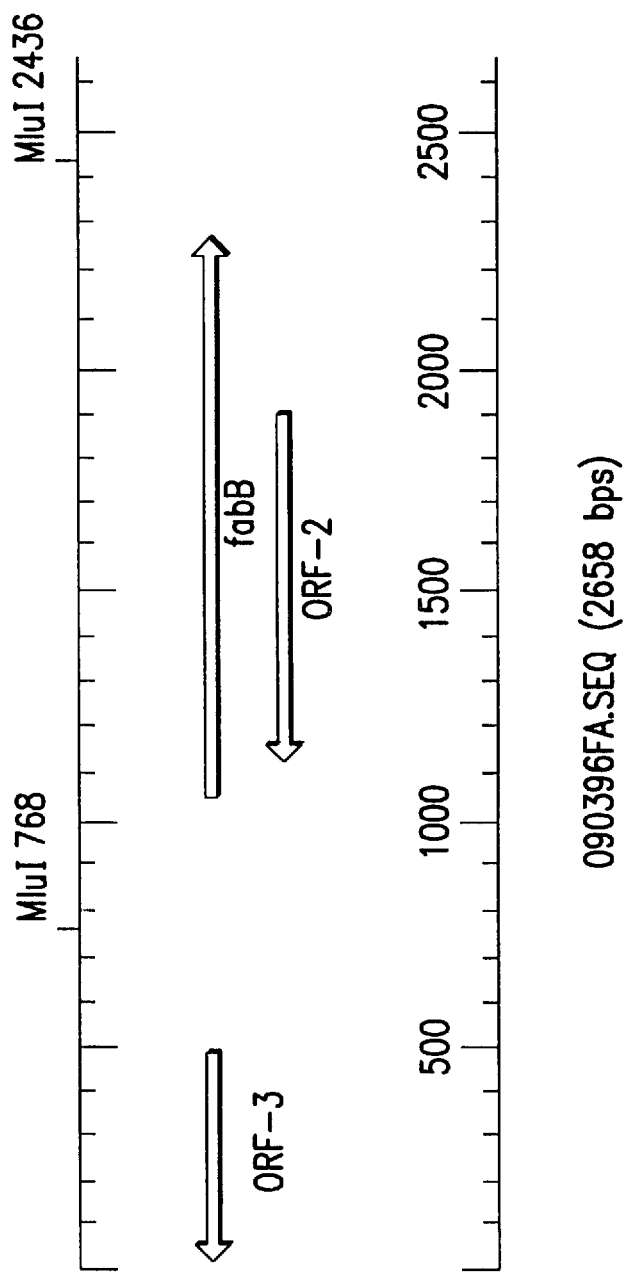
FIG. 14 depicts the open reading frames and location of MluI restriction sites contained within the essential region of cosmid clone 1.

FIG. 14 depicts the open reading frames and the location of the MluI restriction sites on the approximately 2500 bp essential region of cosmid clone 1.

From the sequencing data presented above, the fabB gene can be identified as one potential gene which stabilizes the *E. coli* cells stored in CCMB80 buffer at 4° C. or −20° C.

To further evaluate the ability of the fabB gene to enhance the stability of *E. coli* strains stored at −20° C., the fabB gene from pDELTA2 32 was subcloned into plasmid pDELTA2. Previous data (Tsay J. et al. J. Bact 174: 508–513 1992) indicated that the entire fabB gene could be subcloned as a 1.8 Kb MluI fragment. pDELTA2 32 DNA was digested with MluI at 37° C. for 2 hours. The digestion reaction was electrophoresed on a 1% agarose gel in TAE buffer and the 1.8 Kb fragment was purified using GlassMax (Gibco BRL) following the protocol from the manufacturer. Plasmid pDELTA2 was digested with MluI at 37° C. for 3 hours and treated with alkaline phosphatase at 37° C. for 1 hour. Sodium dodecylsulfate was added to 0.5% followed by proteinase K to 50 μg/ml. The reaction was incubated at 37° C. for 1 hour and then extracted with phenol chloroform. The DNA was precipitated and resuspended in 10 mM Tris (pH 7.5) 1 mM EDTA buffer. The 1.8 Kb MluI fragment was then ligated with the MluI cut alkaline phosphatase treated pDELTA2 vector DNA using T4 DNA Ligase at room temperature for 16 hours. The ligation reaction was then used to transform Max Efficiency DH10B competent cells (Gibco BRL) according to the directions of the manufacturer. Colonies selected on LB plates containing 100 μg/ml ampicillin at 37° C. were then grown for 16 hours 37° C. in LB medium containing 100 μg/ml ampicillin and plasmid DNA was isolated. The plasmid DNA was digested with MluI and screened for the presence of the 1.8 Kb MluI fragment. 4 plasmids (numbered 10, 13, 14 and 15) containing the 1.8 Kb MluI fragment were selected for further study. The plasmid DNA was further screened for the orientation of the MluI fragment by digesting the plasmid DNA with BglI. Gel electrophoresis of the digested fragments indicated that clones 10 and 15 contained the MluI fragment in one orientation and clones 13, 14 contained the MluI fragment in the opposite orientation.

To evaluate the ability of these plasmids containing a cloned MluI insert derived from plasmid pDELTA2 32 to encode the enzymatic function characteristic of fabB gene product, the plasmids designated clones 10, 13, 14 and 15 (as well as plasmids pDELTA2 32 and pDELTA2) were introduced into an E. coli strain which contains a mutation in the fabB gene. Specifically the strain contains the fabB15 (ts) allele which encodes a temperature sensitive fabB gene product. The mutation results in the ability of the strain to grow at 30° C. but not at 42° C. The strain was obtained from the E. coli Genetic Stock Center at Yale University and was given the designation CGSC5641. Competent cells of this strain were prepared as follows: Several colonies of CGSC5641 were picked from an LB plate grown at 30° C. into 50 ml of SOB medium and the flask was shaken at 30° C. 275 rpm.

When the optical density at 550 nm reached 0.308 the cells were collected by centrifugation for 10 min at 4° C. 2500 rpm in an IEC HN SII centrifuge. The cell pellet was resuspended in 4 ml cold CCMB80 buffer and the cells were placed on ice for 20 min. 250 ul of the cells were aliquoted into chilled NUNC tubes and the tubes were frozen in a dry ice ethanol bath. The vials were stored at −80° C. Several tubes of the competent cells were removed from the −80 ° C. freezer and were thawed on ice for approximately 15 min. 100 ul of the competent cells were transformed with 5 ul of plasmid DNA: pDELTA2, pDELTA2 32, clone 10, clone 13, clone 14, clone 15 according to published procedures (Hanahan J. Mol. Biol. 166: 557–580 (1983)). The cells were expressed at 30° C. for 1 hour after addition of SOC. After the expression period, 100 ul of the cells were plated on LB plates containing 100 μg/ml ampicillin and the plates were incubated at either 30° C. or 42° C. If colonies appear on the plates at both 30° C. and 42° C. then the plasmid has provided the enzymatically active fabB gene product which is defective at 42° C. in the E. coli strain CGSC5641. If colonies only appear on the ampicillin plates at 30° C., then the plasmid has failed to provide the active fabB gene product. Table 2 shows the results of the complementation of the fabBts mutation.

TABLE 2

| Strain | Number of Ampicillin Resistant Colonies | | | |
|---|---|---|---|---|
| | 30° C. | | 42° C. | |
| pDELTA2 | 130 | 109 | 0 | 0 |
| Clone 32 | 24 | 22 | 23 | 31 |
| Clone 10 | 162 | 207 | 151 | 160 |
| Clone 13 | 185 | 181 | 179 | 150 |
| Clone 14 | 147 | 152 | 137 | 132 |
| Clone 15 | 205 | 244 | 207 | 213 |

The results in Table 2 indicate that transformation with the pDELTA2 plasmid only results in ampicillin resistant colonies at 30° C. indicating that the pDELTA2 plasmid does not encode an active fabB gene product. Transformation with plasmid pDELTA2 32, clone 10, clone 13, clone 14 and clone 15 results in ampicillin resistant colonies at both 30° C. and 42° C. indicating that these plasmids encode a wild type fabB gene product. Therefore clones 10, 13, 14, and 15 which contain insert DNA of 1.7 Kb (including 1.2 KB of the coding sequence of fabB) express an active fabB gene product. These clones are hereafter referred to as pDELTA2 fabB10, pDELTA2 fabB13, pDELTA2 fabB14 and pDELTA2 fab15.

Figure 15:
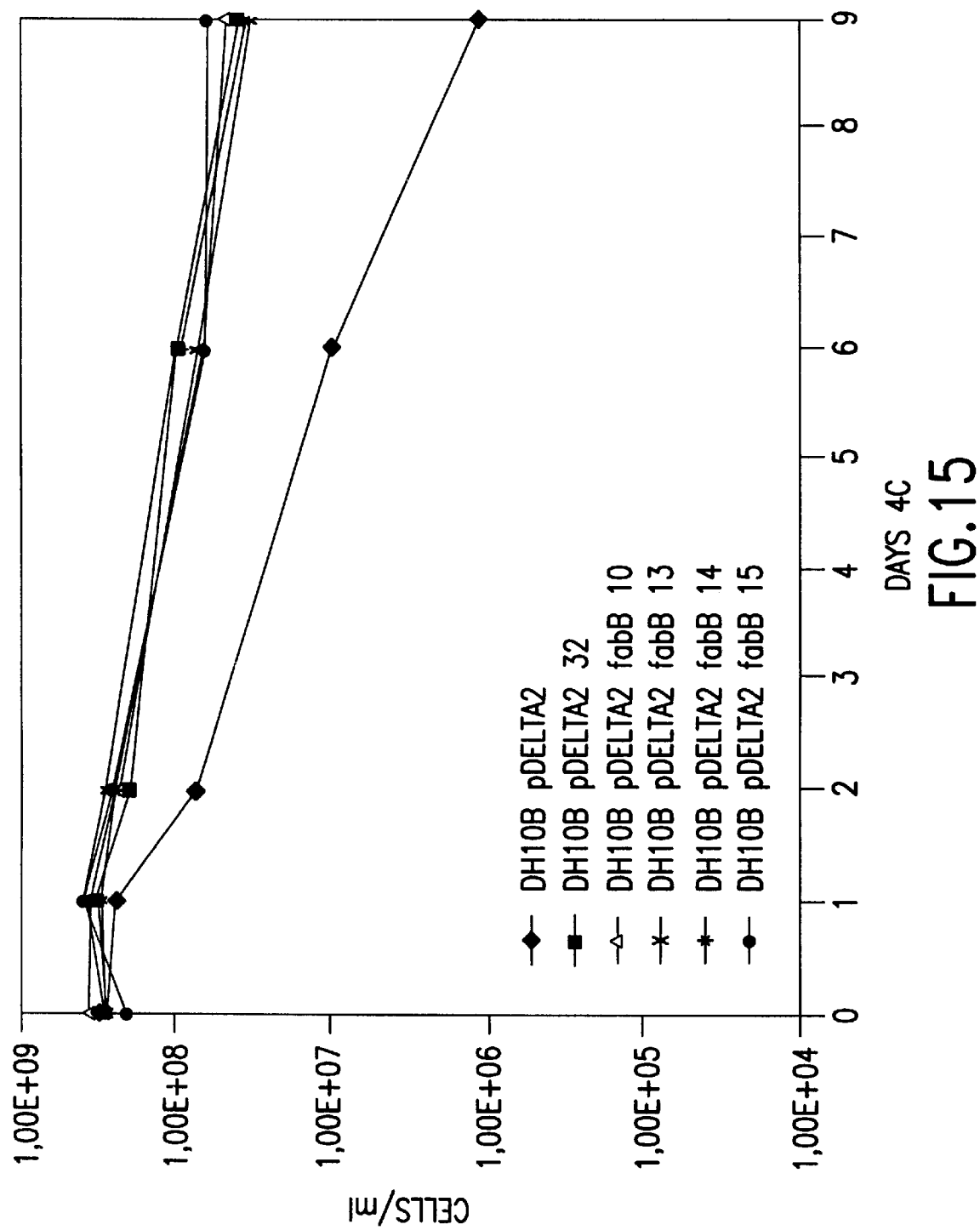
FIG. 15 shows the viability of DH10B cells containing either the pDELTA2, pDELTA2 32, pDELTA2 fab10, pDELTA2 fab13, pDELTA2 fabB14, or pDELTA2 fabB15 plasmid after storage at 4° C. for 9 days.

To evaluate the ability of these plasmids designated pDELTA2 fabB10, pDELTA2 fabB13, pDELTA2 fabB14 and pDELTA2 fabB15 to improve the stability of DH10B cells stored at 4° C. and −20° C., 5 ul of each of the plasmids were transformed into Max Efficiency DH10B competent cells (lot# HFK701) according to directions provided by the Manufacturer. Plasmids pDELTA2 and pDELTA2 32 were also transformed as controls. Transformants were selected on LB agar plates containing 100 μg/ml ampicillin at 30° C. The next day one ampicillin resistant transformant from each transformation was picked into 2 ml of 15/10 medium containing 100 μg/ml ampicillin and the cultures were shaken for 16 hours at 30° C. 0.25 ml of each overnight culture was inoculated into 60 ml of the same medium in a 500 ml baffled shake flask and the cultures were shaken at 30° C. 275 rpm in a New Brunswick floor shaker. The optical density was monitored at 550 nm and the cultures were harvested when the optical density reached 0.26–0.32. 50 ml of the cultures were centrifuged for 10 min at 4° C. in an IEC bench top centrifuge and the pellets were resuspended in 4 ml of cold CCMB80 buffer. The cells were incubated on ice for 20 min. The cells were divided into 2 2 ml portions. One 2 ml portion was frozen in a dry ice ethanol bath for 5 minutes. The cells were then thawed on ice. The viable cell count was determined using serial dilution in 0.85% NaCl. The cells were then placed in a 4° C. refrigerator. The second portion of the cells was processed as follows: 250 ul of the cells were vialed in NUNC cryovials and the vials were frozen in a dry ice ethanol bath. One tube of cells was used to determine the viable cell count and the remainder of the vials were placed in a −20° C. freezer. At intervals the viable cell count was determined from cells stored at 4° C. In addition, tubes were removed from storage at −20° C. for determination of the viable cell count. The results are presented in FIGS. 15 and 16. As seen in FIG. 15 the viable cell count for DH10B cells containing the plasmid pDELTA2 decreased 100 fold after 9 days storage at 4° C. The viable cell count of the DH10B cells containing plasmid pDELTA2 32 (the source of the MluI fragment used in the cloning of the fabB coding sequence) decreased only 8 fold over the same period of time and thus resulted in a 30 fold enhancement in the viable cell count compared to DH10B cells containing the plasmid pDELTA2. DH10B cells containing the pDELTA2 fabB clones 10, 13, 14, and 15 also showed enhanced survival relative to DH10B cells containing vector pDELTA2 by 30–60 fold. Therefore the clones containing the fabB coding sequence resulted in enhanced survival of DH10B cells at 4° C.

Figure 16:
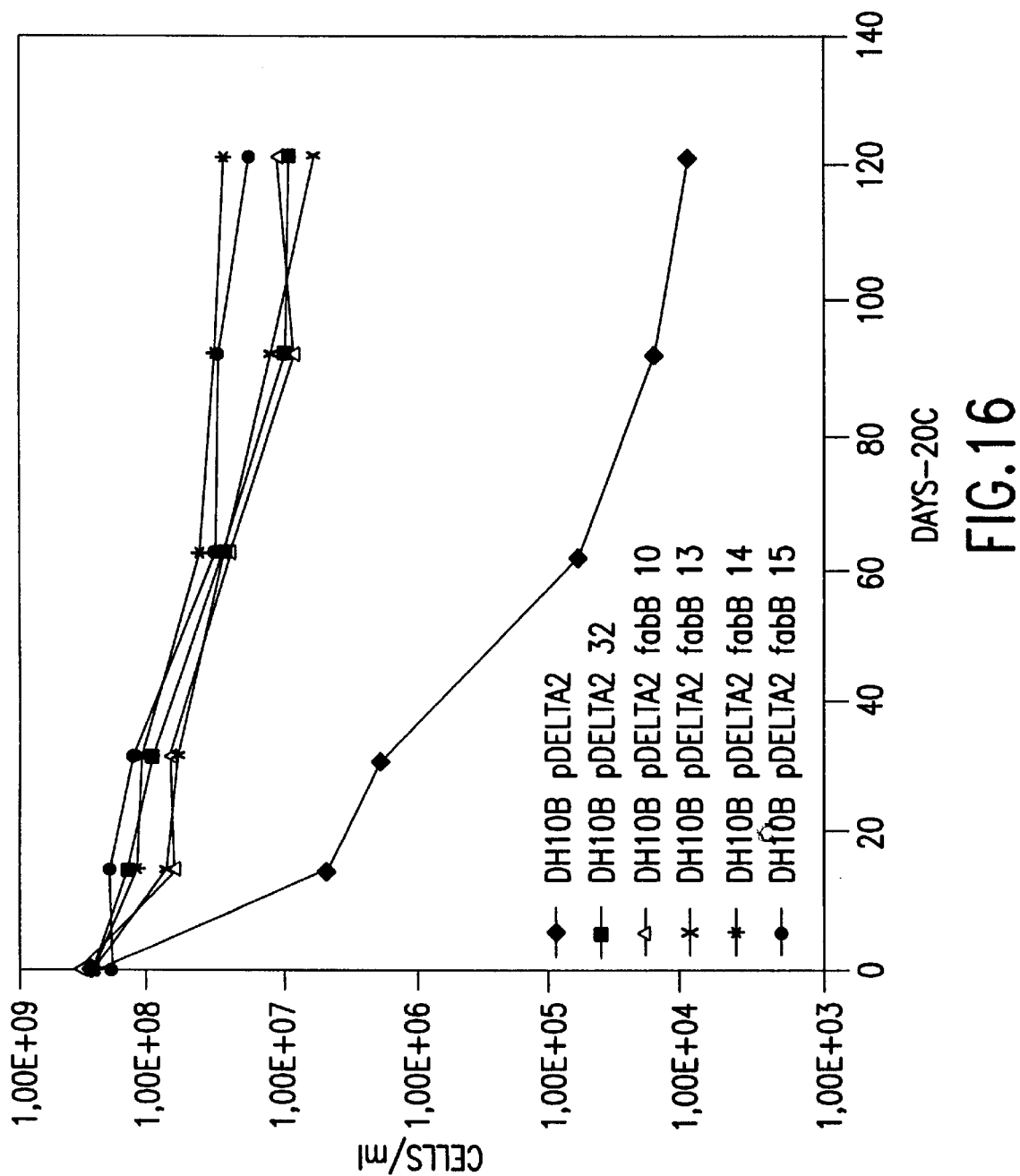
FIG. 16 shows the viability of DH10B cells containing either the pDELTA2, pDELTA2 32, pDELTA2 fab10, pDELTA2 fab13, pDELTA2 fabB14, or pDELTA2 fabB15 after storage at −20° C. (for approximately 120 days).

As seen in FIG. 16, both plasmids pDELTA2 32 and pDELTA2 fabB clones 10, 13, 14, and 15 also result in enhanced survival of DH10B cells when the cells are stored at −20° C. The fabB clones resulted in a 400–700 fold enhancement in the viability of DH10B cells relative to the viability of the DH10B cells containing the plasmid pDELTA2.

In order to provide more evidence that plasmids which express an active fabB gene product enhance stability of DH10B cells stored at 4° C. and −20° C., the coding sequence of fabB on plasmids pDELTA2 fabB 14 and pDELTA2 fabB 15 was interrupted by deletion of an approximately 750 bp fragment. Plasmid DNA from pDELTA2 fabB 14 and pDELTA2 fabB15 (encoding an enzymatically active fabB gene) were digested with Kpn2I at 55° C. for 1 hour. PinAI was then added and the reaction was incubated for a further 1 hour at 37° C. The digestion reaction was electrophoresed on a 1% agarose gel with TAE buffer. A 9 Kb fragment isolated from the gel was purified with GlassMax (Gibco BRL) and the purified DNA was resuspended in TE buffer. The ends of the 9 Kb fragment were ligated with T4 DNA ligase at room temperature for 16 hours. The ligation reaction was used to transform Max Efficiency DH10B competent cells with selection on LB plates containing 100 μg/ml ampicillin at 37° C. Colonies were picked from the plate into LB medium containing 100 μg/ml ampicillin and the cultures were grown for 16 hours at 37° C. Plasmid DNA was isolated, digested with MluI and BglI and analyzed by gel electrophoesis. Two plasmids, designated pDELTA2 14 deletion and pDELTA2 15 deletion, were shown to be lacking the 750 bp fragment.

To determine if deletion of the 700 bp fragment resulted in loss of the fabB gene product, plasmids pDELTA2, pDELTA2 fabB14, pDELTA2 fabB15, pDELTA2 14 deletion and pDELTA2 15 deletion were transformed into competent cells of CGSC5641 (fabB15ts). The results are presented in Table 3.

TABLE 3

| Clone | Number of Ampicillin Resistant Colonies | | Number Screened | Number Temperature Resistant |
| --- | --- | --- | --- | --- |
|  | 42° C. | 30° C. |  |  |
| fabBts | 0 | 0 | — | — |
| +pDELTA2 | 1 | 123 | 20 | 0 |
| +clone 14 | 114 | 123 | 20 | 20 |
| +clone 15 | 288 | 360 | 20 | 20 |
| 14 deletion | 0 | 56 | 20 | 0 |
| 15 deletion | 0 | 221 | 20 | 0 |

Table 3 shows the results of the transformation of CGSC5641 (fab15ts) competent cells with pDELTA2, pDELTA2 fab14, pDELTA2 14 deletion, pDELTA2 fabB15 or pDELTA2 15 deletion plasmid. Transformation of plasmid pDELTA2 into competent cells of CGSC5641 results in ampicillin resistant colonies only at 30° C. indicating that the pDELTA2 plasmid does not encode a functional fabB gene product.

Transformation of plasmids pDELTA2 fabB 14 or pDELTA2 fabB15 into competent cells of CGSC5641 result in ampicillin resistant colonies at both 30° C. and 42° C. indicating that plasmids pDELTA2 fabB14 and pDELTA2 fabB15 encode a functional fabB gene product. Transformation of plasmids pDELTA2 14 deletion or pDELTA2 15 deletion result in ampicillin resistant colonies only at 30° C. indicating that these plasmids do not encode a functional fabB gene product. Therefore, deletion of approximately 750 bp of the fabB coding region results in an inability to complement a fabBts mutation.

MluI sites are at positions 768 and 2436. The deletions in MluI14Δ and MluI15Δ were confirmed by sequencing across the juncture with the fab470 primer (SEQ ID NO: 5). The 3' end of the fab470 primer is positioned at 1298 bases in the our fabB gene sequence. The deletions should remove bases 1310 through 2033. Typically, approximately the first twenty bases of sequence 3' of the primer are not readable, so using this primer the first readable base would be at about 1318 in the fabB sequence if there were no deletion, and at about 2041 if the deletion was present. Since the readable sequence begins at 2041 for both clones the deletions are as expected. The Sequence of clones MluI14Δ and MluI15Δ from primer fab470 (SEQ ID NO.: 17) are as follows:

$^{2041}$CTCTCTGGGCGCTGCTGGCGTACAGGAAGCT-ATCTACTCTCT GCTGATGCTGGAACACGGC-TTTATCGCCCCGAGCATCAACATTGAAGAGCT-GGACGAGCAGGCTGCGGGTCTGAA-CATCGTGACCGA$^{2169}$

To determine whether disruption of the fabBcoding sequence reduces the ability of the plasmids to stabilize DH10B cells, the plasmids pDELTA2, pDELTA2 fab14, pDELTA2 fabB15, pDELTA2 14 deletion, and pDELTA2 15 deletion were transformed into Max Efficiency DH10B lot HFK701. The transformants were plated on LB plates containing ampicillin at 100 μg/ml at 30° C. for 16 hours. Single colonies from each transformation were picked into 2 ml 15/10 medium containing ampicillin at 100 μg/ml and the cultures were shaken at 30° C. for 16 hours. 0.25 ml of the overnight culture were inoculated into 50 ml of the same medium and were grown to an optical density at 550 nm of 0.27 to 0.30. The cells were collected by centrifugation for 10 min 4° C. 2500 rpm in an IEC HN SII centrifuge and the cell pellet was resuspended in 4 ml cold CCMB80 buffer. The cells were placed on ice for 20 min and 250 ul of cells were vialed in chilled NUNC cryovials. The cells were frozen for 5 min in a dry ice ethanol bath and were placed in a −20° C. freezer. The remainder of the cells were frozen in a dry ice ethanol bath, thawed and placed at 4° C. Viable counts were determined by serial dilution in 0.85% saline. At intervals viable counts were determined after various periods at either 4° C. or −20° C.

Figure 17:
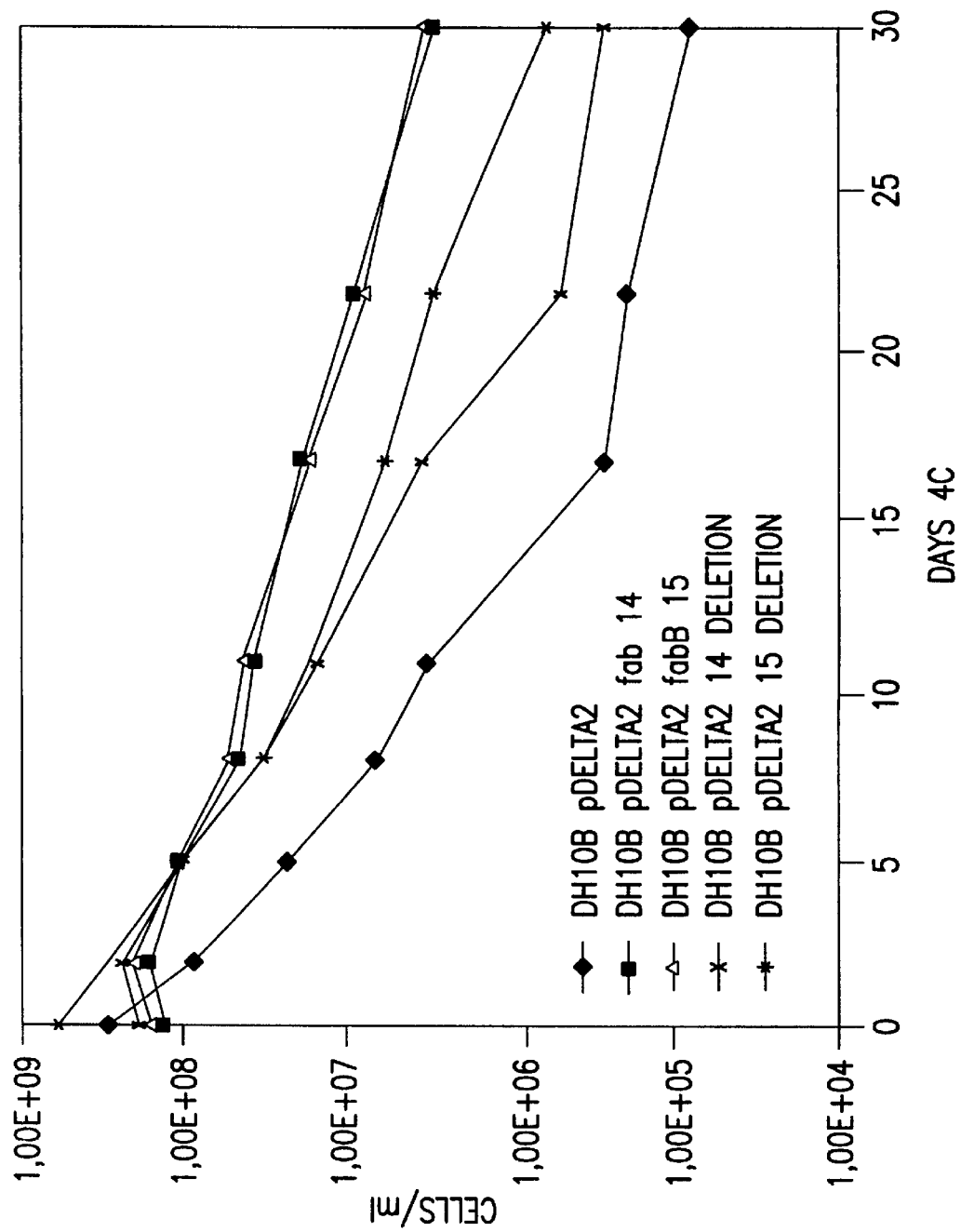
FIG. 17 shows the viability of DH10B cells containing either the pDELTA2, pDELTA2 fab14, pDELTA2 14 deletion, pDELTA2 fabB15 or pDELTA2 15 deletion plasmid after storage at 4° C. for up to 30 days.
Figure 18:
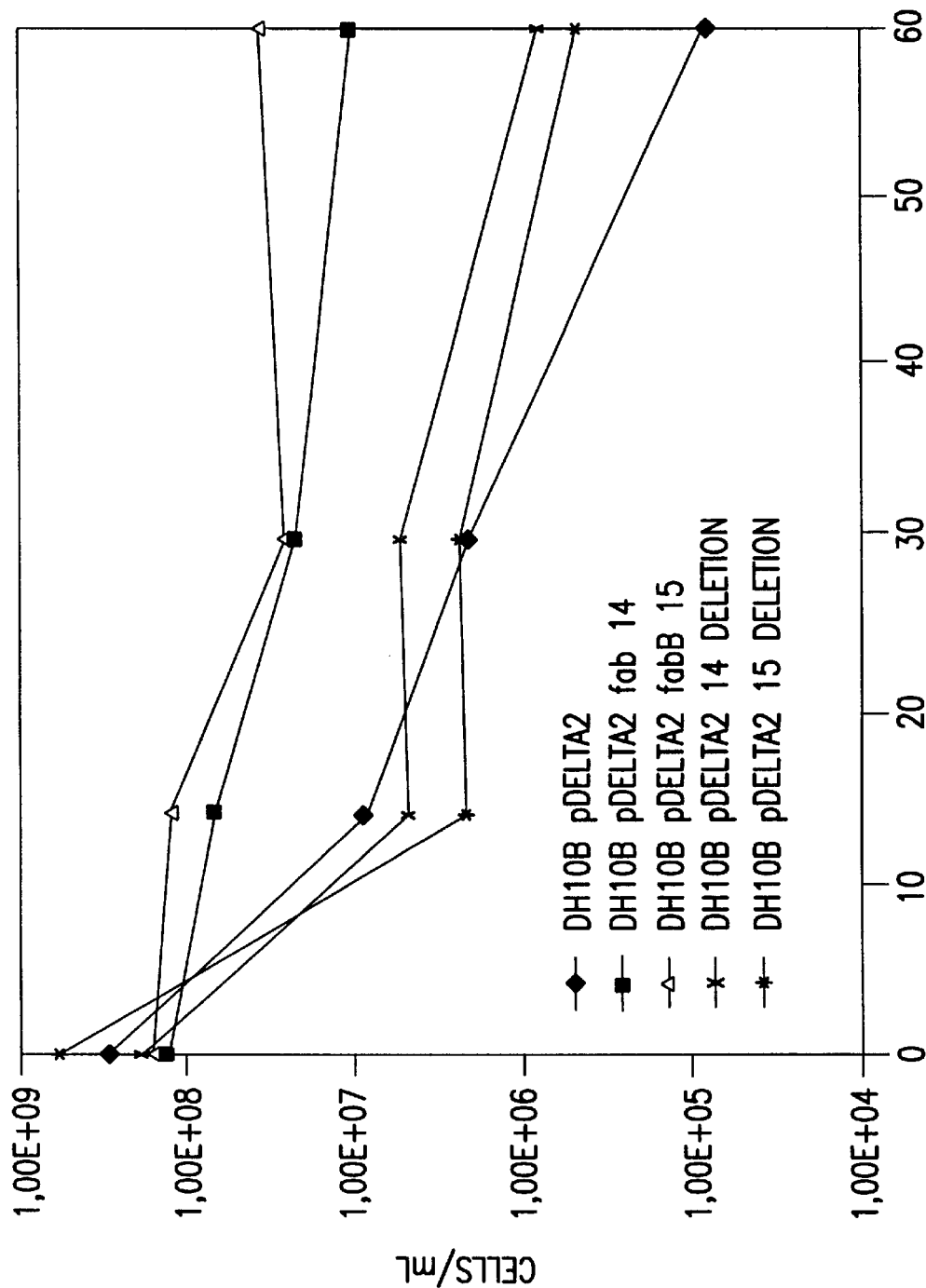
FIG. 18 shows the viability of DH10B cells containing either the pDELTA2, pDELTA2 fabB14, pDELTA2 14 deletion, pDELTA2 fab15 or pDELTA2 15 deletion plasmid after storage at −20° C. for up to 60 days.

The results are presented in FIGS. 17 and 18. FIG. 17 shows that the viable cell count of DH10B cells containing the pDELTA2 plasmid stored at 4° C. in CCMB80 buffer declines over a period of 30 days from $1\times10^8$ cells/ml to $1\times10^5$ cells/ml. The viable cell count of cells containing plasmid pDELTA2 fabB 14 or pDELTA2 fabB15 is approximately 100 fold higher than cells containing the pDELTA2 vector. These results indicate that a plasmid which contains a functional fabB gene significantly enhances the stability of DH10B cells stored at 4° C. DH10B cells containing deletion derivatives which interrupt the fabB coding sequence (plasmids pDELTA2 14 deletion and pDELTA2 15 deletion) have a substantially lower viable cell count than in DH10B cells containing an intact fabB coding sequence. These results indicate that disruption of the fabB coding sequence eliminates the ability of these plasmids to stabilize DH10B cells. The viable cell counts of DH10B pDELTA2 14 deletion and pDELTA15 deletion are slightly higher than the viable cell counts of DH10B pDELTA2 cells. These results may indicate a slight increase in the fabB gene product (from the intact fabB gene in the chromosome of strain DH10B) in cells which contain plasmids with interrupted fabB coding sequence possibly due to regulatory effects of these plasmids. FIG. 18 indicates that DH10B cells containing pDELTA2 plasmid stored at −20° C. for 60 days show a marked instability with a 3 log decrease in viable cell count. The presence of a functional fabB gene product (due to the presence of plasmids pDELTA2 fabB14 or pDELTA2 fabB15) results in a 100 fold increase in the viable cell count. Again, the presence of deletion derivatives which interrupt the fabB coding sequence results in a slightly higher viable cell count than in cells containing plasmid pDELTA2 but a much lower viable cell count than cells containing plasmids which encode a functional fabB gene product.

These results indicate that the presence of an intact fabB gene on a multicopy plasmid improves the stability of DH10B cells when the cells are stored at either 4° C. or −20° C.

EXAMPLE 15

Effect of FabB on Levels of Unsaturated Fatty Acids

One consequence of the cloning and overexpression of the fabB gene in *E. coli* is an increase in total amount of unsaturated fatty acids found in membrane phospholipids. This increase is a result of an increase in the cis vaccenate level (de Mendoza D. et al. J. Biol Chem 258: 2098–2101 (1983)). To evaluate whether the cloned fabB gene causes a similar increase in the cis-vaccenate level (and thus an increase in the total amount of unsaturated fatty acids) in DH5α and DH10B cells, pCP13, cosmid clone 1, pDELTA2 and pDELTA2 fabB15 were transformed into competent cells of DH5α and DH10B and the cells were grown for an analysis of the fatty acids present in the cell membrane. Cells were also analyzed for stability at −20° C. in CCMB80 buffer. Transformants were selected at 30° C. on LB plates containing 50 μg/ml kanamycin (for pCP13 and cosmid clone 1) or 100 μg/ml ampicillin (for pDELTA2 and pDELTA2 fabB15). Colonies from these plates were inoculated into 2 ml of medium. For DH5α pCP13 and DH5α cosmid clone 1 the cells were inoculated into SOB medium containing 50 μg/ml kanamycin. For DH5α pDELTA2 and DH5α pDELTA2 fabB15 the cells were inoculated into SOB medium containing 100 μg/ml ampicillin. For DH10B pCP13 and DH10B cosmid clone 1 the cells were inoculated into 15/10 medium containing 50 μg/ml kanamycin. For DH10B pDELTA2 and DH10B pDELTA2 fabB15 the cells were inoculated into 15/10 medium containing 100 μg/ml ampicillin. The cells were grown at 30° C. for 16 hours. 250 ul of the cultures were inoculated into 60 ml of the same medium and the cultures were grown at 30° C. 275 rpm. The optical density was monitored at 550 nm and when the cultures reached an optical density of approximately 0.3 (range 0.253–0.312) the cells were collected by centrifugation. Specifically, 40 ml of the cells were collected by centrifugation for 10 min at 4° C. 2500 rpm in an IEC HN SII centrifuge. The cell pellets were resuspended in 3.2 ml of cold CCMB80 and the cells were placed on ice for 20 min. 250 ul of the cells were vialed in NUNC cryovials and the vials were frozen in a dry ice ethanol bath for 5 min. The cells were stored in a −20° C. freezer for the stability study. At intervals 2vials were removed from the freezer and the cells were assayed for the viable cell count. The remainder of the cells (15–20 ml) were collected by centrifugation, washed once in 10 mM Tris HCl pH7.5 and the cell pellets were stored at −20° C. The lipids were extracted from the cell pellets and were analyzed for fatty acids.

The cell pellet was washed and resuspended in distilled water and the solution was transferred to a glass tube. Two volumes of methanol and one volume of chloroform were added to the glass tube for each volume of cell solution. After mixing and centrifuging, the supernatant was transferred to a new glass tube. One volume of distilled water and one volume of chloroform were added to the tube and a two phase solution was obtained. The organic phase was transferred to a new glass tube and the organic solution was dried by blowing nitrogen gas onto the surface of the solution. 2 ml of ethanol was then added to each tube and the solution was again dried with nitrogen. The ethanol wash step was repeated. 2 m1 of 0.5M sodium methoxide (Aldrich) was added to each tube and the tubes were kept at room temperature for 1 hour. 0.1 ml of glacial acetic acid and 5 ml of distilled water were added to each tube. The solution was extracted 2 times with 5 ml hexane. The solution was then dried and redissolved in 200 ul of carbon disulfide.

For GC analysis, a Hewlett-Packard 5890 Series II gas chromatograph equipped with a capillary inlet system and HP 7673 automatic sampler was used (Hewlett-Packard, Palo Alto, Calif.). The column was a 30 m×0.32 u m I.D. fused silica capillary column coated with demethylpolysiloxane with a film thickness of 1.0 u (Alltech, Deerfield, Ill.). Ultra high purity helium at a flow rate of 1 ml/min was used as the carrier gas. A split-injection (50:1) mode was used, with the injector set at 285° C. The oven temperature was set at 190° C. After each analysis, the oven temperature was increased by 50° C./min to 285° C. and held for 10 min. The FID detector temperature was 285° C.

Table 4 shows the effects of the presence of fabB clones on the level of unsaturated fatty acids in DH5α and DH10B.

TABLE 4

| # | Samples | % Survival −20° C. 1 Mo | % Survival −20° C. 2 Mo | Fatty Acid Composition C14:0 | C16:0 | C16:1 | C17:0 | C18:0 | C18:1 | C19:0 |
|---|---|---|---|---|---|---|---|---|---|---|
| 1 | DH5α pCP13 | 6 | 2 | 2 | 41.5 | 32.5 | 3.8 | 3.2 | 15.5 | 1.5 |
| 2 | DH5α clone 1 | 28 | 9 | 1.8 | 22.2 | 25.5 | 4.5 | 3.6 | 41 | 1.4 |
| 3 | DH5α pDELTA2 | 7 | 1 | 0.3 | 43.2 | 37.3 | 2.4 | 1.4 | 12.2 | 3.2 |
| 4 | DH5α pDELTA fabB15 | 28 | 12 | 0.2 | 4.8 | 22 | 0.3 | 3.4 | 69.2 | 0.1 |
| 5 | DH10B pCP13 | 7 | 0.7 | 0.15 | 34.6 | 30.4 | 4.2 | 0.4 | 29.9 | 0.3 |
| 6 | DH10B clone 1 | 6 | 4 | 1.6 | 28.5 | 26.2 | 4.1 | 0.4 | 40.6 | 0.05 |
| 7 | DH10B pDELTA2 | 4 | 0.4 | 1.6 | 35.9 | 27.4 | 5.4 | 0.3 | 29.3 | 0.1 |
| 8 | DH10B pDELTA fabB15 | 59 | 29 | 0.3 | 14.2 | 17.6 | 3.5 | 1.9 | 62.4 | 0.1 |

Figure 19:
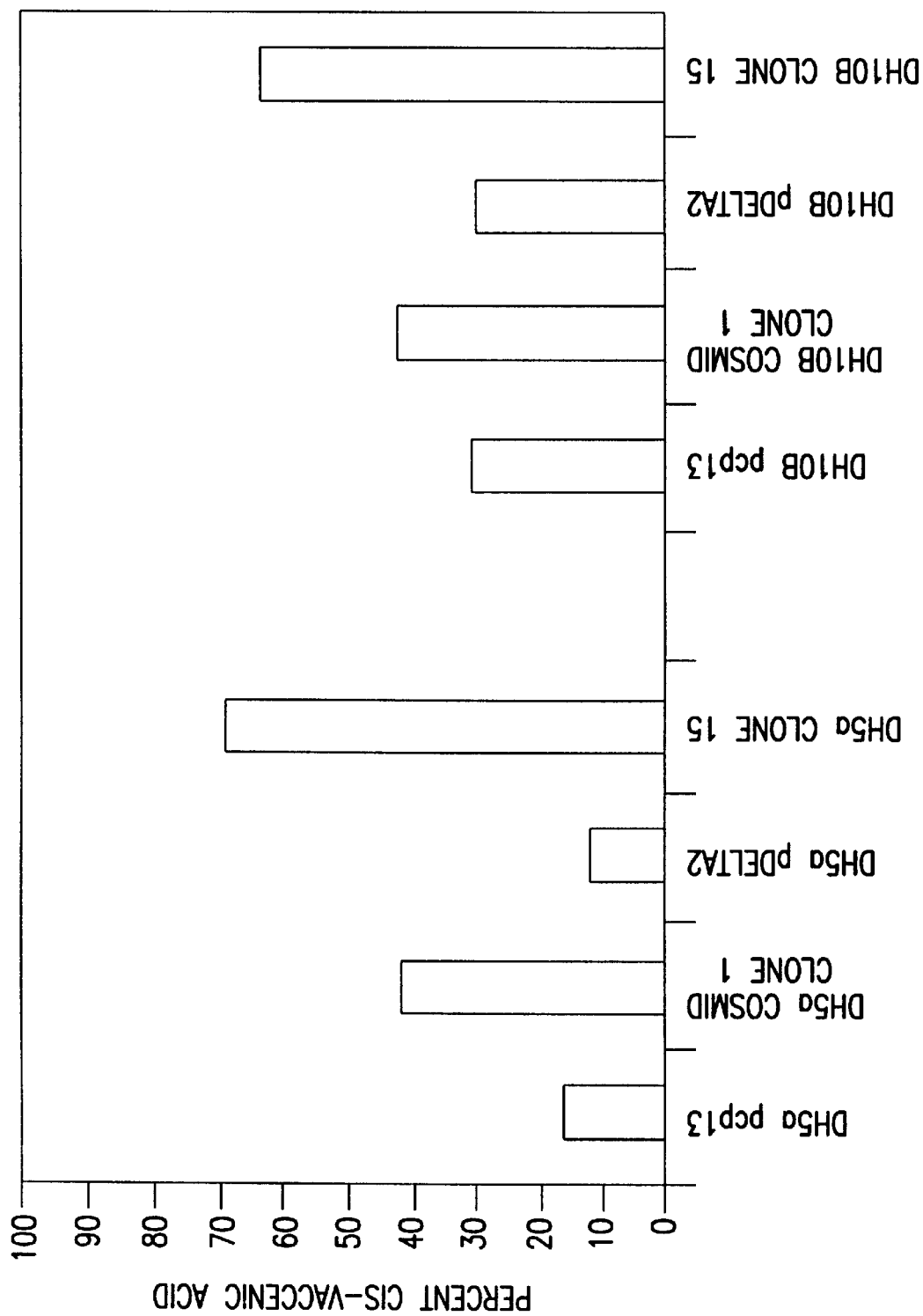
FIG. 19 shows the effect of the presence of various fabB clones in strains DH5α and DH10B on percent cis vaccenic acid levels.
Figure 20:
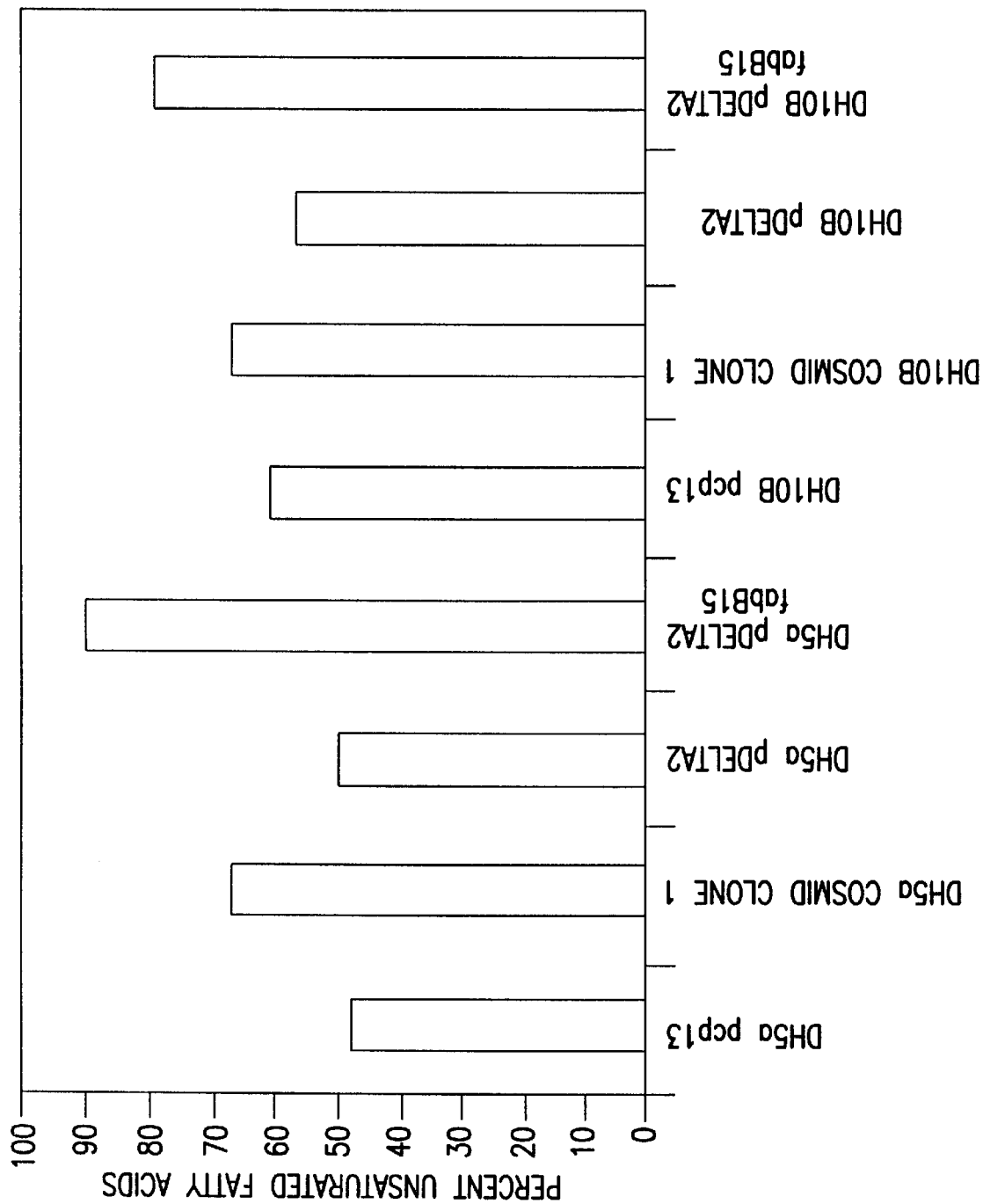
FIG. 20 shows the effect of the presence of various fabB clones in strains DH5α and DH10B on percent unsaturated fatty acids levels.

In Table 4, C14:0 refers to myrsitic acid, C16:0 refers to palmitic acid, C16:1 refers to palmitoleic acid, C17:0 refers to margaric acid, C18:0 refers to stearic acid, C18:1 refers to cis-vaccenic acid, and C19:0 refers to nondecylic acid. As seen in Table 4, and FIG. 19, the presence of cosmid clone 1 in strain DH5α increases the cis vaccenate level from 15.5% in strain DH5α pCP13 to 41% in DH5α cosmid clone 1. The presence of plasmid pDELTA2 fabB15 increases the cis vaccenate level from 12.2% in DH5α pDELTA2 to 69.2% in DH5α pDELTA2 fabB15. A similar increase in the cis vaccenate level is seen in strain DH10B. The cis vaccenate level increases from 29.9% in strain DH10B pCP13 to 40.6% in strain DH10B cosmid clone 1 and from 29.3% in strain DH10B pDELTA2 to 62.4% in strain DH10B pDELTA2 fabB15. When the level of total unsaturated lipids (both C18:1 and C16:1) are calculated, the presence of a functional fabB gene on a plasmid increases the unsaturated fatty acid level from 48–49% in strains DH5α pCP13 and DH5α pDELTA2 to 66.5% in DH5α cosmid clone 1 and to 91% in strain DH5α pDELTA2 fab15 (FIG. 20). As expected, the higher copy number plasmid pDELTA2 fabB15 increases the unsaturated lipid level more than the lower copy number cosmid clone 1. In strain DH10B the presence of a functional fabB gene on a plasmid increases the unsaturated fatty acid level from 56–60% in strains DH10B pCP13 and DH10B pDELTA2 to 67% in strain DH10B cosmid clone 1 and to 80% in DH10B pDELTA2 fabB15 (FIG. 20). Again, the higher copy number plasmid pDELTA2 fabB15 increases the unsaturated lipid level more than the lower copy number cosmid clone 1.

Figure 21:
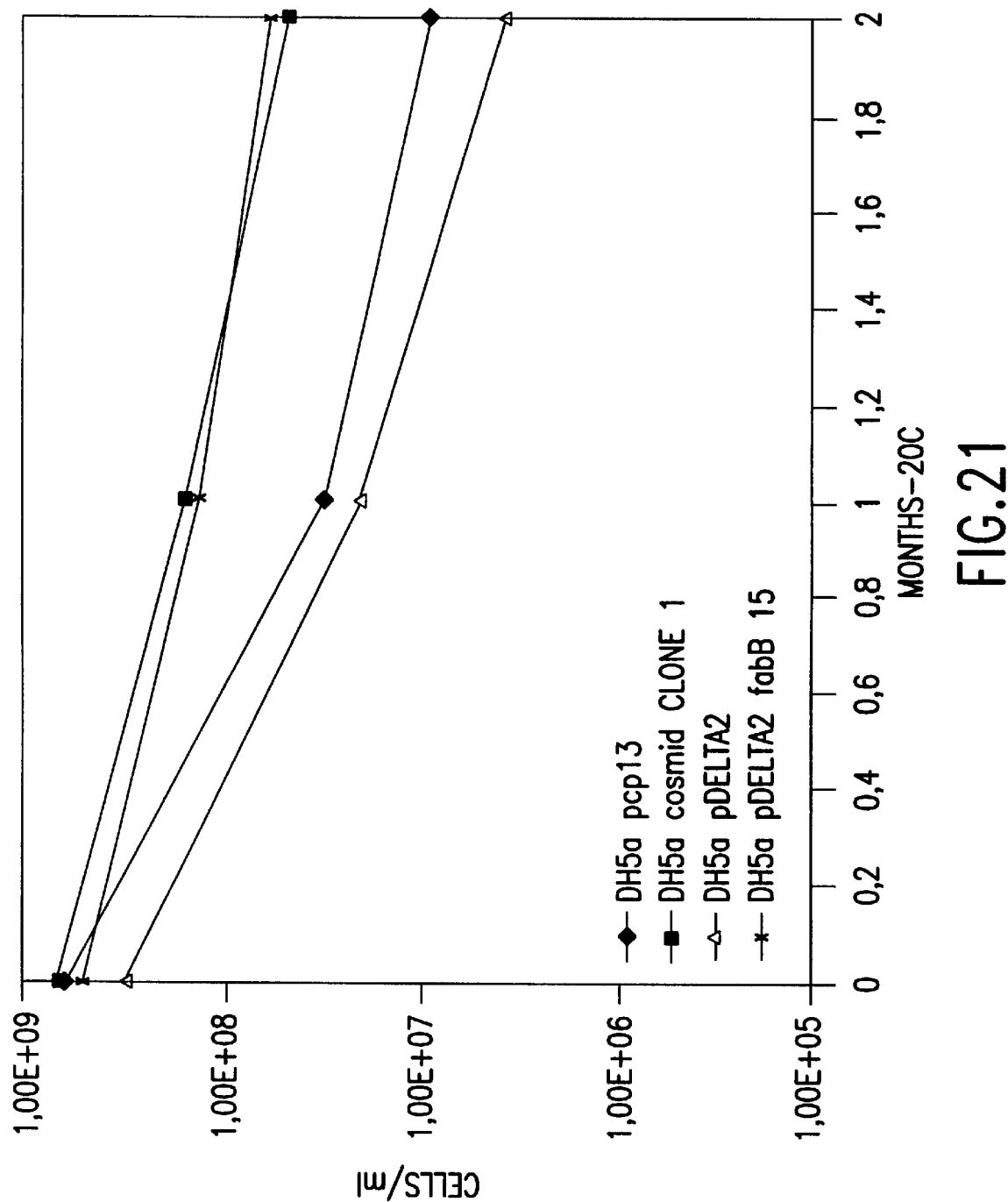
FIG. 21 shows the viability of DH5α cells containing either the pCP13, cosmid clone 1, pDELTA2, or pDELTA2 fab15 plasmid after storage at −20° C. for up to 2 months.
Figure 22:
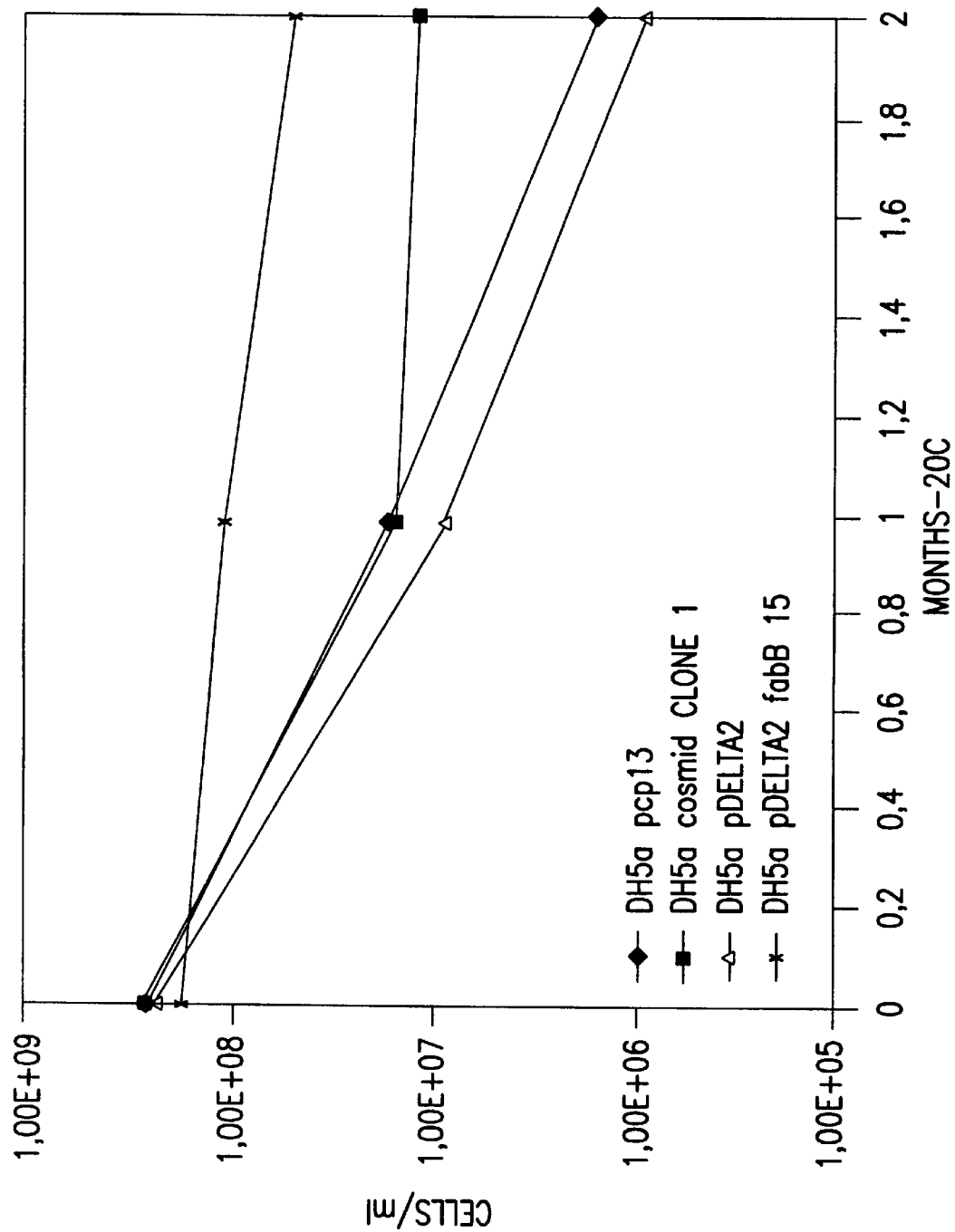
FIG. 22 shows the viability of DH10B cells containing either the pCP13, cosmid clone 1, pDELTA2, or pDELTA2 fabB15 plasmid after storage at −20° C. for up to 2 months.

The results of the stability study can be found in FIGS. 21 and 22. As seen in FIG. 21, the DH5α cells containing pCP13 or pDELTA2 are unstable at −20° C. and the viable cell count decreases from 3–5 ×$10^8$ cells/ml to 3.9–10×$10^6$ cells/ml over a period of 2 months. DH5α cells containing cosmid clone 1 or pDELTA2 fabB 15 are more stable than the control cells and have 5–10 fold more viable cells/ml compared to cells containing pCP13 or pDELTA2. Similarly DH10B cells containing pCP13 or pDELTA2 are also unstable at −20° C. decreasing from 2–3×$10^8$ cells/ml to approximately 1.0×$10^6$ cells/ml over the same period of time at −20° C. (FIG. 22). DH10B cells containing cosmid clone 1 or pDELTA2 fabB 15 are more stable with 10–40 fold higher viable cell counts than found in control cells.

Figure 23:
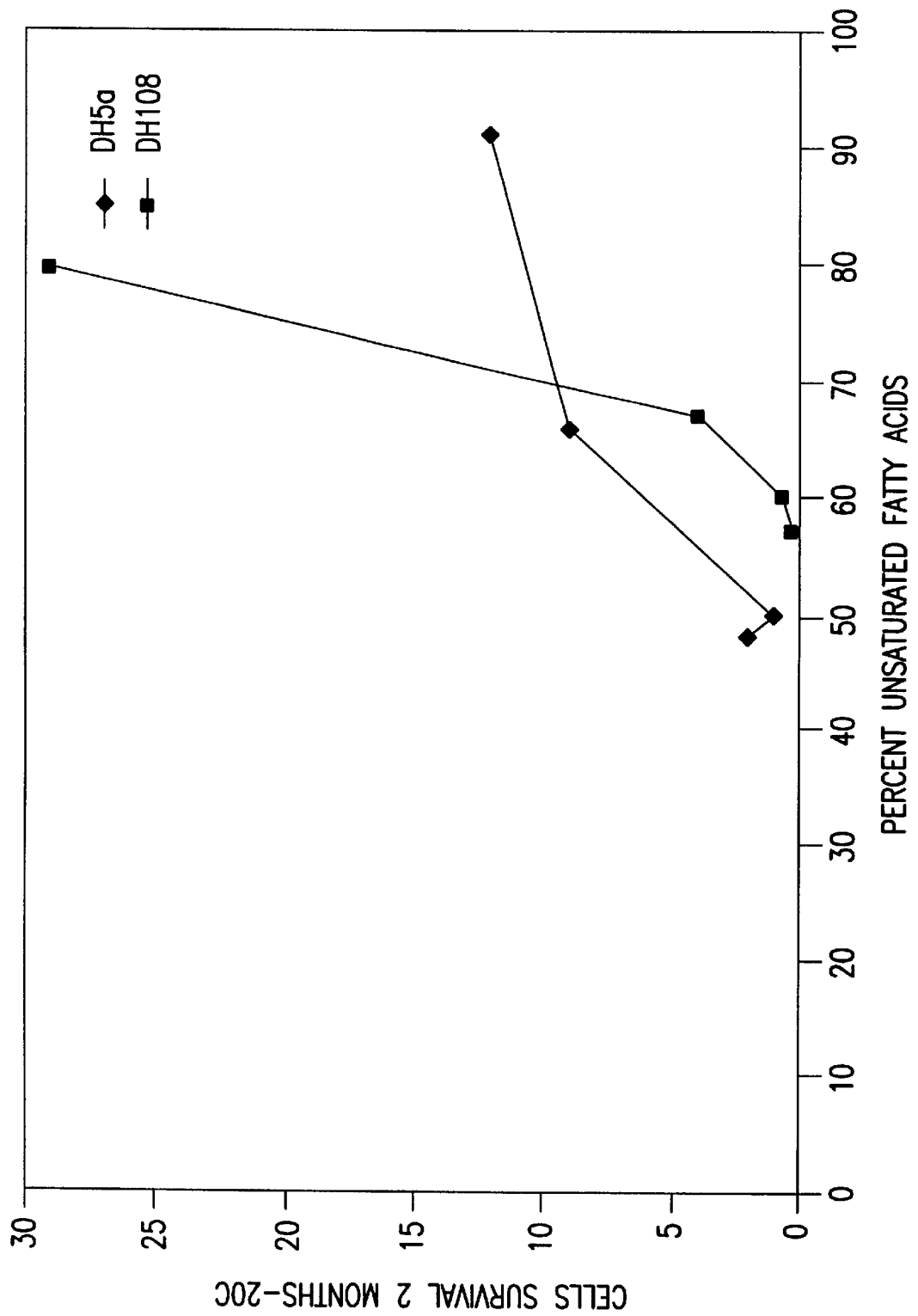
FIG. 23 shows the correlation that exists between the survival of DH5α and DH10B cells at −20° C. for two months and the amount of unsaturated fatty acids found in the cell membrane.

As indicated in FIG. 23, a correlation exists between the survival of the DH5α and DH10B cells at −20° C. and the amount of unsaturated fatty acids found in the cell membrane. When the results are plotted as cell survival at −20° C. on the y axis and percent of total lipids as unsaturated fatty acids on the x axis, the results indicate that the higher the value of total unsaturated lipids in the cell membrane, the greater the survival rate of the cells at −20° C. (FIG. 23).

(Ulrich, A. K. et al., J. Bact 154: 221–230 (1983)). Specifically, CY322, DH10B and SB3499B master seeds stored at −70° C. were used as a source of the cells used for this experiment. The strains were streaked on LB plates and the plates were incubated at 23° C., 30° C., 37° C., and 42° C. The cells from these plates were used to inoculate 1.5 ml broth cultures. For DH10B and SB3499B the cells were inoculated into 15/10 medium. For CY322 the cells were inoculated into SOB medium. The cultures were grown at 23° C., 30° C., 37° C., and 42° C. for 16 hours. 0.3 ml of the DH10B and SB3499B cells were inoculated into 60 ml of 15/10 medium and the cultures were grown at the appropriate growth temperature 275 rpm and the optical density was monitored at 550 nm. 0.2 ml of the CY322 cells were inoculated into 25 ml of SOB medium and the cultures were shaken at the appropriate growth temperature. When the optical density of the CY322 cells reached 0.25 (range 0.24–0.262) the cells were collected by centrifugation at 4° C. for 10 min 2500 rpm in an IEC HN SII centrifuge. The cell pellets were washed once with 10 mM Tris HCl pH7.5 and the cell pellets were stored at −20° C. The lipids were extracted and analyzed by GC as presented in Example 17. For the DH10B and SB3499B cells, the optical density was monitored and when the OD reached approximately 0.3 (range 0.24–0.33, 40 ml of the cells were collected by centifugation and the cell pellets were resuspended in 0.32 ml of cold CCMB80. The cells were allowed to remain on ice for 20 min and 250 ul was vialed in NUNC cryovials. The vials were frozen in a dry ice ethanol bath and were stored at −20° C. for the stability study. 15–20 ml of the cells were also centrifuged and the cell pellets were washed once in 10 mM Tris pH7.5. The cell pellets were stored at −20° C. and were then extracted for analysis as in Example 17.

Figure 24:
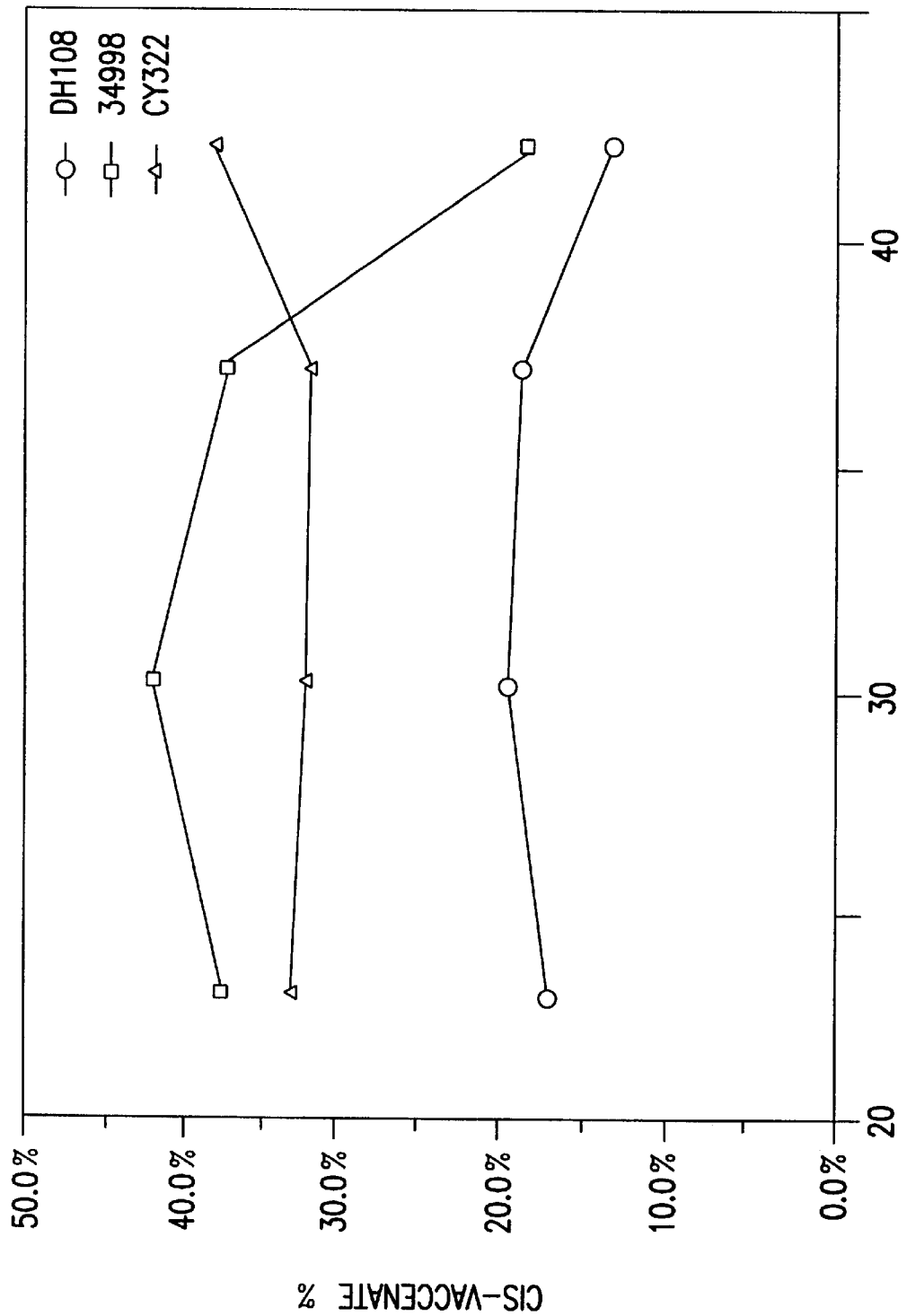
FIG. 24 shows the correlation that exists between the growth temperature of DH10B, SB3499B, and CY322 cells grown at 23° C., 30° C., 37° C., or 42° C. for 16 hours, and the amount of cis vaccenate in the cells.

The results of the lipid analysis are found in Table 5 and FIG. 24.

TABLE 5

| | | | Fatty Acid Composition | | | | | |
|---|---|---|---|---|---|---|---|---|
| # | Sample | Growth Temp. | C14:0 | C16:0 | C16:1 | C17:0 | C18:0 | C18:1 |
| 1 | DH10B | 23° C. | 5.6% | 41.0% | 31.8% | 2.1% | 2.1% | 17.4% |
| 3 | DH10B | 30° C. | 4.3% | 39.4% | 32% | 2.6% | 1.3% | 20.3% |
| 5 | DH10B | 37° C. | 3.3% | 40.3% | 29.8% | 3.7% | 3.3% | 19.6% |
| 9 | DH10B | 42° C. | 4.5% | 49.2% | 27.5% | 2.5% | 2.3% | 14.0% |
| 2 | SB3499B | 23° C. | 0.8% | 24.2% | 34.4% | 2.3% | 0.8% | 37.5% |
| 4 | SB3499B | 30° C. | 1.3% | 24.4% | 27.9% | 3.0% | 1.7% | 42.1% |
| 6 | SB3499B | 37° C. | 1.4% | 29.2% | 27.5% | 3.7% | 0.6% | 37.6% |
| 10 | SB3499B | 42° C. | 2.9% | 42.8% | 28.8% | 3.2% | 2.9% | 19.4% |
| 11 | CY322 | 23° C. | 2.4% | 29.6% | 28.3% | 1.6% | 4.9% | 33.2% |
| 12 | CY322 | 30° C. | 2.6% | 32.4% | 22.5% | 3.9% | 6.0% | 32.6% |
| 13 | CY322 | 37° C. | 3.2% | 33% | 21.4% | 6.1% | 4.1% | 32.3% |
| 14 | CY322 | 42° C. | 1.6% | 37.6% | 14.6% | 1.8% | 5.7% | 38.7% |

EXAMPLE 16

Increased Survival of SB3499B Cells

To determine if the increased survival of SB3499B cells stored at −20° C. was due to an increased level of unsaturated fatty acids in the cell membrane, DH10B and SB3499B cells were grown at several different temperatures and the lipids were analyzed as in Example 15. In addition, strain CY322 containing a mutation in fabF was also included in this study. This particular fabF mutation results in the overproduction of cis vaccenate at all growth temperatures In Table 5, C14:0 refers to myrsitic acid, C16:0 refers to palmitic acid, C16:1 refers to palmitoleic acid, C17:0 refers to margaric acid, C18:0 refers to stearic acid, C18:1 refers to vaccenic acid, and C19:0 refers to nondecylic acid.

FIG. 24 indicates that cells of SB3499B have a higher level of cis vaccenate (37–42%) compared to cells of DH10B (17–20%). The higher levels of cis vaccenate are found in SB3499B cells grown at either 23° C., 30° C., or 37° C. However, if the SB3499B cells are grown at 42° C. the level of cis vaccenate is not appreciably greater than in DH10B cells grown at 42° C. In addition, the cells of CY322 grown at 23° C., 30° C., 37° C., or 42° C. have levels of cis vaccenate which are greater than those levels found in DH10B and which do not appreciably vary with the growth temperature. This finding is consistent with the known phenotype of E. coli strains which have the fabF mutation (such as CY322), specifically the overproduction of cis vaccenate regardless of growth temperature.

Figure 25:
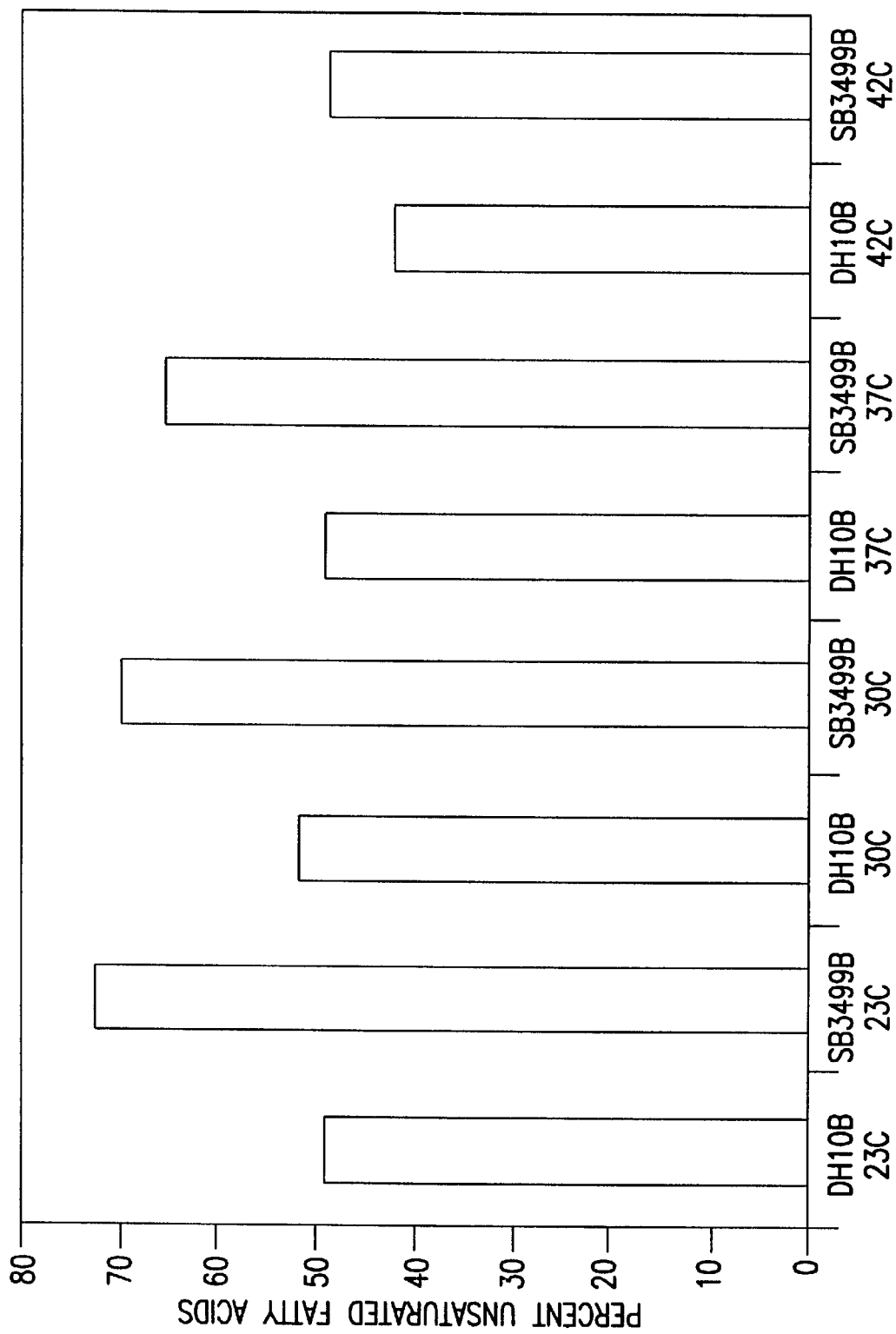
FIG. 25 shows the effect of varying growth temperature on the levels of unsaturated fatty acids in the cell membrane of DH10B, SB3499B, and CY322 cells grown at 23° C., 30° C., 37° C., or 42° C.

FIG. 25 also indicates that, at 23° C., 30° C., and 37° C., the total level of unsaturated lipids (C16:1 and C18:1) is greater in SB3499B cells than in DH10B cells. The levels range from 65% to 71% in SB3499B and from 49% to 52% in DH10B. On the other hand, when these 2 strains are grown at 42° C., the levels of unsaturated lipids is essentially the same in both strains (41% in DH10B and 48% for SB3499B. These results indicate that SB3499B, at most growth temperatures examined, overproduces cis vaccenate compared to cells of DH10B. As a result, at these same growth temperatures, the levels of unsaturated lipids in the phospholipid are higher in SB3499B than in DH10B (FIG. 25).

Figure 26:
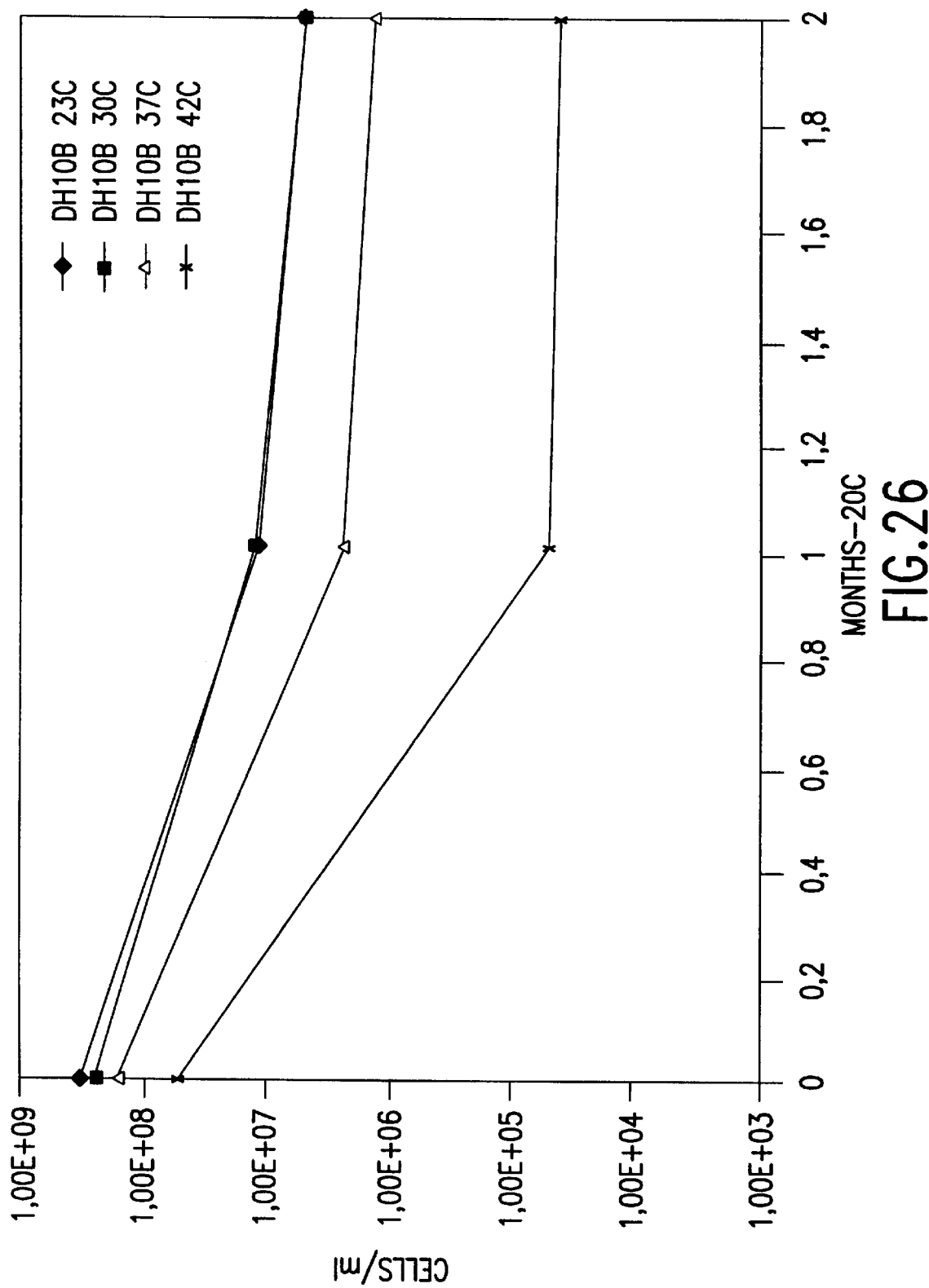
FIG. 26 shows the viability of DH10B cells grown at 23° C., 30° C., 37° C., or 42° C. after storage at −20° C. for up to 2 months.
Figure 27:
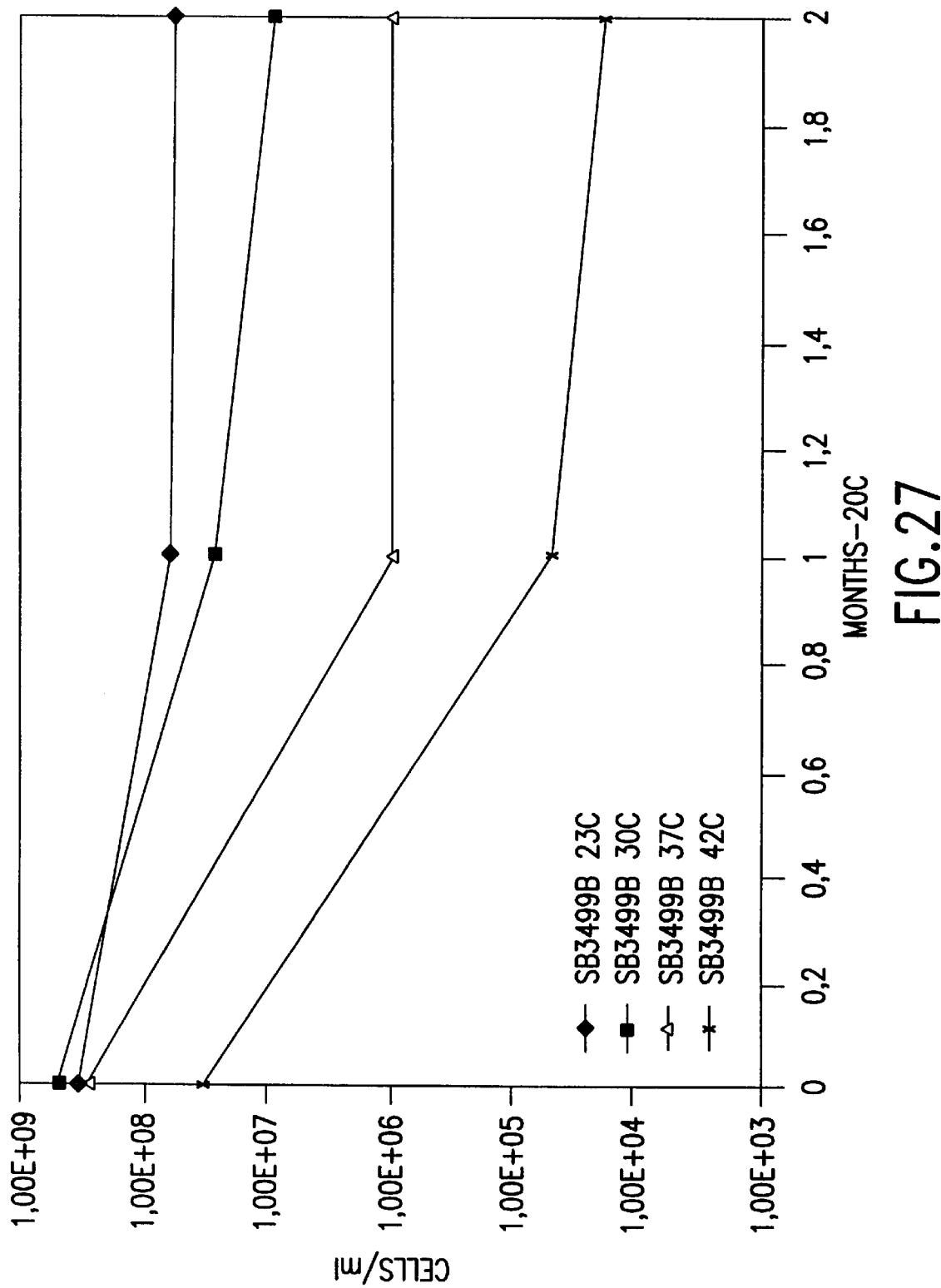
FIG. 27 shows the viability of SB3499B cells grown at 23° C., 30° C., 37° C., or 42° C. after storage at −20° C. for up to 2 months.
Figure 28:
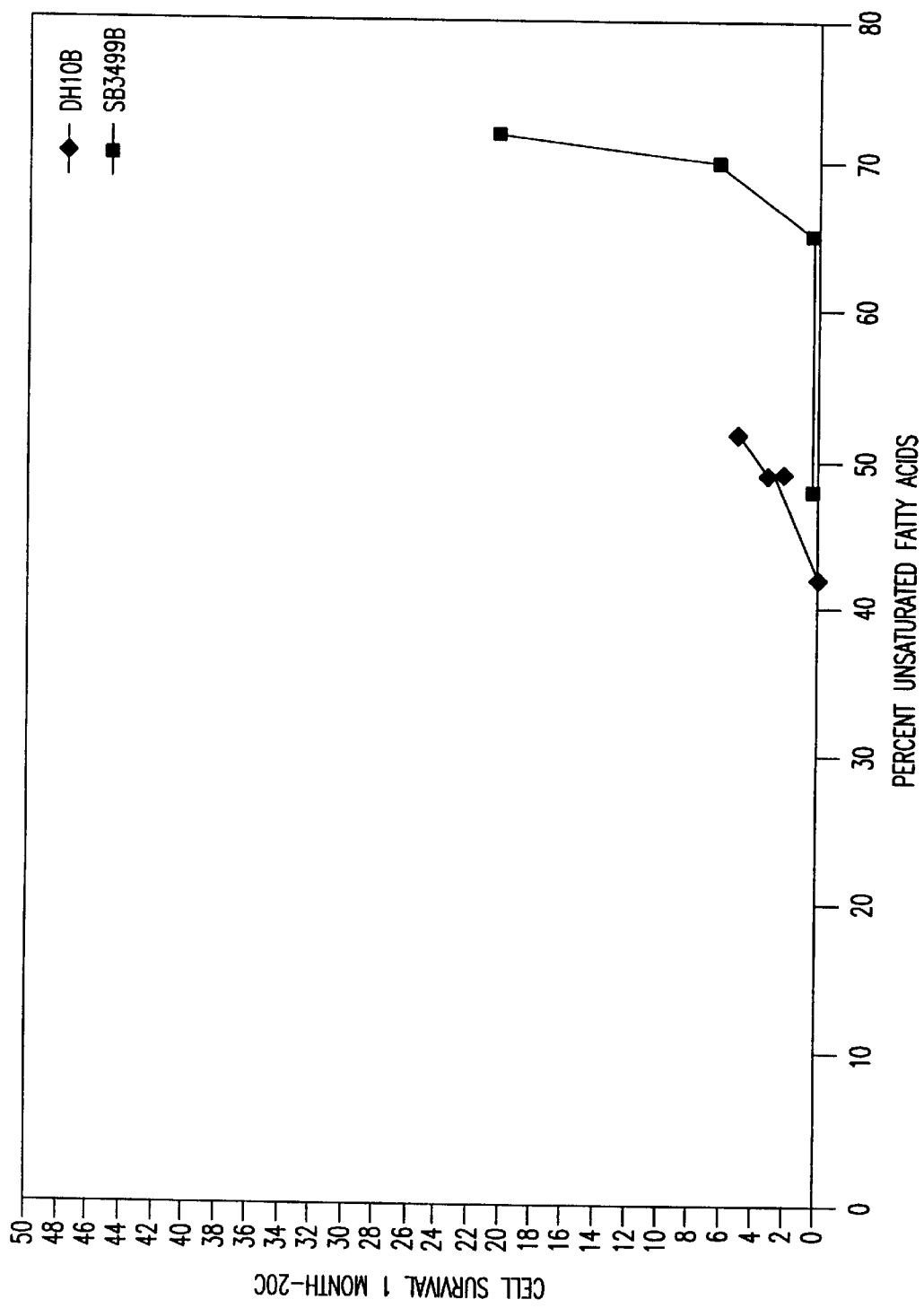
FIG. 28 shows the corelation between the total unsaturated fatty acids of the cell membrane and cell survival at −20° C. for strains DH10B and SB3499B.

The results of the −20° C. stability study are presented in FIGS. 26 and 27. The DH10B cells are quite unstable when stored at −20° C. but appear more unstable when cells are grown at 37° C. or 42° C. DH10B cells grown at 23° C. or 30° C. and stored at −20° C. lose approximately 90% of the viable cells after one month at −20° C. whereas DH10B cells grown at 37° C. or 42° C. lose approximately 99% of the viable cells. SB3499B cells again demonstrate enhanced survival compared to DH10B cells but the effect depends on the growth temperature. The SB3499B cells grown at 23° C. and stored at −20° C. for one month have a 6 fold higher viable cell count compared to DH10B cells. However, the improvement in the viable cell count of SB3499B cells relative to DH10B cells becomes progressively less pronounced as the growth temperature increases. SB3499B cells grown at 37° C. or 42° C. are no more stable at −20° C. than are the DH10B cells. The correlation between total unsaturated fatty acids in the cell membrane and cell survival at −20° C. can be observed when the cell survival at −20° C. is plotted against the total unsaturated fatty acid content of the cell membrane. This data is shown in FIG. 28. The data indicates a correlation in that for both strains SB3499B and DH10B, an increase in the total unsaturated fatty acid composition of the cell membrane results in an enhanced cell survival at −20° C.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the inventions pertains and as may be applied to the essential features hereinbefore set forth and as follows in the scope of the appended claims.

What is claimed is:

1. A method for obtaining enhanced viability of a bacterial culture subjected to storage at a temperature of from about +4° C. to about −80° C. which comprises:
  (a) modifying bacteria of said culture by introducing into said bacteria one or more genes that encode one or more gene products that increases the percentage of unsaturated fatty acids in the membrane of said bacterium relative to total fatty acids therein; wherein said modified bacteria express said one or more encoded gene products; and
  (b) subjecting said bacterial culture to said storage, wherein said one or more gene products causes said bacteria to exhibit enhanced viability relative to that exhibited by said bacteria prior to said modification (a).

2. A method for enhancing the transformation ability of a bacterial culture which comprises:
  (a) modifying bacteria of said culture by introducing into said bacteria one or more genes that encode one or more gene products that increases the percentage of unsaturated fatty acids in the membrane of said bacterium relative to total fatty acids therein; wherein said modified bacteria express said one or more encoded gene products; and
  (b) subjecting said bacterial culture to transformation, wherein said one or more gene products causes said bacteria to exhibit enhanced transformation ability relative to that exhibited by said bacteria prior to said modification (a).

3. The method of claims 1 or 2, wherein said modification (a) comprises enhancing expression of one or more of said encoded genes.

4. The method of claim 3, wherein said enhanced expression comprises increasing copy number of said genes.

5. The method of claim 3, wherein said enhanced expression comprises increasing transcription or translation of said genes.

6. The method of claims 1 or 2, wherein said bacterium is a gram negative bacterium.

7. The method of claim 6, wherein said bacterium is of the genus *Escherchia*.

8. The method of claim 7, wherein said bacterium is *E. coli*.

9. The method of claims 1 or 2, wherein said one or more gene products increases the percentage of an unsaturated fatty acid selected from the group consisting of oleic acid, linoleic acid, palmitoleic acid, and cis-vaccenic acid in the membrane of said bacterium relative to total fatty acids therein.

10. The method of claim 9, wherein said unsaturated fatty acid is selected from the group consisting of cis-vaccenic acid and palmitoleic acid.

11. The method of claims 1 or 2, wherein said one or more gene products increases the total content of unsaturated fatty acid in the membrane of said modified bacterium.

12. The method of claims 1 or 2, wherein said low temperatures range from about −20° C. to about 4° C.

13. The method of claim 1, wherein said one or more genes are selected from the group consisting of a fabB gene, a fabF gene, a fabD gene, a fabG gene, a fabA gene, a fabI gene, a fabZ gene, a fadA gene, a fadB gene, a fadE gene, a fadL gene, a fadR gene, a farR gene, and a fatA gene.

14. The method of claim 1, wherein said one or more genes is a fabB gene.

15. The method of claim 2, wherein said one or more genes are selected from the group consisting of a fabB gene, a fabF gene, a fabD gene, a fabG gene, a fabA gene, a fabI gene, a fabZ gene, a fadA gene, a fadB gene, a fadE gene, a fadL gene, a fadR gene, a farR gene, and a fatA gene.

16. The method of claim 2, wherein said one or more genes is a fabB gene.

\* \* \* \* \*